United States Patent
Gluckman et al.

(10) Patent No.: US 11,744,508 B2
(45) Date of Patent: *Sep. 5, 2023

(54) BIOLOGICAL MARKER AND METHODS

(71) Applicant: The Penn State Research Foundation, University Park, PA (US)

(72) Inventors: Bruce J. Gluckman, State College, PA (US); Fatemeh Bahari, State College, PA (US); Steven J. Schiff, State College, PA (US)

(73) Assignee: The Penn State Research Foundation, University Park (PA)

( * ) Notice: Subject to any disclaimer, the term of this patent is extended or adjusted under 35 U.S.C. 154(b) by 51 days.

This patent is subject to a terminal disclaimer.

(21) Appl. No.: 17/468,398

(22) Filed: Sep. 7, 2021

(65) Prior Publication Data
US 2021/0401356 A1 Dec. 30, 2021

Related U.S. Application Data

(63) Continuation of application No. 16/396,316, filed on Apr. 26, 2019, now Pat. No. 11,141,097.
(Continued)

(51) Int. Cl.
*A61B 5/00* (2006.01)
*A61B 5/0205* (2006.01)
(Continued)

(52) U.S. Cl.
CPC .......... *A61B 5/4094* (2013.01); *A61B 5/0205* (2013.01); *A61B 5/316* (2021.01);
(Continued)

(58) Field of Classification Search
CPC ..... A61B 5/4094; A61B 5/316; A61B 5/0205; A61B 5/7275
See application file for complete search history.

(56) References Cited

U.S. PATENT DOCUMENTS 8,512,240 B1 * 8/2013 Zuckerman-Stark ....... A61B 5/7203
128/924
9,050,469 B1 * 6/2015 Osorio ............... A61B 5/316
(Continued)

FOREIGN PATENT DOCUMENTS

WO WO-2012118562 A1 * 9/2012 .......... A61K 31/137
WO WO-2018235076 A1 * 12/2018 ............. G16H 50/20

OTHER PUBLICATIONS

Altenmüller et al., "High-Grade Atrioventricular Block Triggered by Spontaneous and Stimulation-Induced Epileptic Activity in the Left Temporal Lobe," Epilepsia, 45(12):1640-44, Nov. 2004.
(Continued)

*Primary Examiner* — Eric D. Bertram
(74) *Attorney, Agent, or Firm* — Fish & Richardson P.C.

(57) ABSTRACT

Systems, methods, and other techniques for monitoring, including non-invasive monitoring, of biological markers based on the interaction, temporal association, or coincidence of brain activity and periphery activity in a mammal are provided. Systems and methods for generating a behavioral state-independent representation of cardiac activity and for identifying cardiac events and/or brain-periphery, e.g., brain-cardiac, temporal associations useful as biomarkers of disease such as, e.g., neurologic disease, in a mammal are also provided.

18 Claims, 24 Drawing Sheets

Related U.S. Application Data

(60) Provisional application No. 62/663,213, filed on Apr. 26, 2018.

(51) Int. Cl.
  *A61B 5/316* (2021.01)
  *A61B 5/352* (2021.01)
  *A61B 5/374* (2021.01)

(52) U.S. Cl.
  CPC .............. *A61B 5/352* (2021.01); *A61B 5/374* (2021.01); *A61B 5/7275* (2013.01)

(56) References Cited

U.S. PATENT DOCUMENTS

| | | | |
|---|---|---|---|
| 9,592,378 B2 | 3/2017 | Gluckman et al. | |
| 11,141,097 B2 | 10/2021 | Gluckman et al. | |
| 2006/0135877 A1* | 6/2006 | Giftakis | A61N 1/36521 600/513 |
| 2006/0224067 A1* | 10/2006 | Giftakis | A61B 5/4094 600/483 |
| 2007/0239054 A1* | 10/2007 | Giftakis | A61B 5/375 600/513 |
| 2007/0265536 A1* | 11/2007 | Giftakis | A61B 5/318 600/508 |
| 2007/0265677 A1* | 11/2007 | Giftakis | A61B 5/4094 607/45 |
| 2012/0296175 A1* | 11/2012 | Poh | A61B 5/02405 600/483 |
| 2015/0088024 A1* | 3/2015 | Sackellares | G06K 9/00523 600/544 |
| 2015/0282755 A1* | 10/2015 | Deriche | A61B 5/318 600/301 |
| 2018/0055394 A1* | 3/2018 | Sohrabpour | A61B 5/369 |
| 2019/0328306 A1 | 10/2019 | Gluckman et al. | |

OTHER PUBLICATIONS

Ansakorpi et al., "Heart Rate Dynamics in Refractory and Well Controlled Temporal Lobe Epilepsy," J. Neurol. Neurosurg. Psychiatry, 72(1):26-30, Jan. 2002.

Baharav et al., "Fluctuations in Autonomic Nervous Activity during Sleep Displayed by Power Spectrum Analysis of Heart Rate Variability," Neurology, 45(6):1183-87, Jun. 1995.

Bar-Klein et al., "Losartan Prevents Acquired Epilepsy via TGF-β Signaling Suppression," Ann. Neurol., 75(6):864-75, Jun. 2014.

Bar-Klein et al., "Imaging Blood-Brain Barrier Dysfunction as a Biomarker for Epileptogenesis," Brain, 140(6): 1692-1705, 2017.

Bar-Klein et al., "Isoflurane Prevents Acquired Epilepsy in Rat Models of Temporal Lobe Epilepsy," Ann. Neurol., 80(6):896-908, 2016.

Boudreau et al., "Circadian Variation of Heart Rate Variability Across Sleep Stages," Sleep, 36(12):1919-28, Dec. 2013.

Bryce and Sprague, "Revisiting Detrended Fluctuation Analysis," Sci. Rep., 2:315, 2012.

Choi et al., "Intrinsic Cardiac Nerve Activity and Paroxysmal Atrial Tachyarrhythmia in Ambulatory Dogs," Circulation, 121(24):2615-23, 2010.

DeGiorgio et al., "RMSSD, a Measure of Vagus-Mediated Heart Rate Variability, Is Associated with Risk Factors for SUDEP: The SUDEP-7 Inventory," Epilepsy Behav., 19(1):78-81, Sep. 2010.

Devinsky et al., "Bradycardia and Asystole Induced by Partial Seizures: A Case Report and Literature Review," Neurology, 48(6):1712-4, Jun. 1997.

Dichter, "Emerging Concepts in the Pathogenesis of Epilepsy and Epileptogenesis," Arch.Neurol., 66(4):443-7, Apr. 2009.

Doytchinova et al., "Simultaneous Noninvasive Recording of Skin Sympathetic Nerve Activity and Electrocardiogram," Heart Rhythm. 14(1):25-33, Jan. 2017.

Dütsch et al., "Impaired Baroreflex Function in Temporal Lobe Epilepsy," J. Neurol., 253(10):1300-8, Oct. 2006.

Engel et al., "High-Frequency Oscillations: What Is Normal and What Is Not?" Epilepsia, 50(4):598-604, Apr. 2009.

Engel et al.,"Epilepsy Biomarkers," Epilepsia, 54(Suppl4):61-9, 2013.

Esteller et al., "Line Length: An Efficient Feature for Seizure Onset Detection," in 2001 Conference Proceedings of the 23rd Annual International Conference of the IEEE Engineering in Medicine and Biology Society, IEEE, 1707-10, 2001.

Evrengül et al.., "Time and Frequency Domain Analyses of Heart Rate Variability in Patients with Epilepsy," Epilepsy Research, 63(2-3):131-9, Feb. 2005.

Frysinger et al., "Interictal Heart Rate Patterns in Partial Seizure Disorders," Neurology, 43(10):2136-9, 1993.

Fujiwara et al., "Epileptic Seizure Prediction Based on Multivariate Statistical Process Control of Heart Rate Variability Features," IEEE Transactions on Biomedical Engineering, 63(6):1321-2 Dec. 2015.

Govindan et al., "Detrended Fluctuation Analysis of Non-Stationary Cardiac Beat-to-Beat Interval of Sick Infants," EPL, 108(41:4005, Nov. 2014.

Hajek et al., "Influence of Vigilance State on Physiological Consequences of Seizures and Seizure-Induced Death in Mice," J. Neurophys., 115(5):2286-93, May 2016.

Hashimoto et al., "Heart rate variability features for epilepsy seizure prediction," in 2013 Asia-Pacific Signal and Information Processing Association Annual Summit and Conference 2013 (pp. 1-4). IEEE.

Hellwig et al., "Tremor-Correlated Cortical Activity in Essential Tremor," Lancet, 357(9255):519-23, Feb. 2001.

Hellwig et al., "Tremor-Correlated Cortical Activity Detected by Electroencephalography," Clin. NeurophysioL, 111(5):806-9, May 2000.

Herr et al., "Reduced Cardiac Output in Imported Plasmodium Falciparum Malaria," Malaria J., 10(1):160, Dec. 2011.

Hilz et al., "Decrease of Sympathetic Cardiovascular Modulation after Temporal Lobe Epilepsy Surgery," Brain 125(5):985-95, May 2002.

Jung et al., "Circadian Variations of Stellate Ganglion Nerve Activity in Ambulatory Dogs," Heart Rhythm, 3(1):78-85, 2006.

Kane et al. "A Revised Glossary of Terms Most Commonly Used by Clinical Electroencephalographers and Updated Proposal for the Report Format of the EEG Findings. Revision 2017," Clin. Neurophysiol. Pract., 2:170-85, Sep. 2017.

Kanemaru et al., "Jerky Spontaneous Movements at Term Age in Preterm Infants Who Later Developed Cerebral Palsy," Early Hum. Dev., 90(8):387-92, Aug. 2014.

Kheiri et al . . . "Non-Linear Classification of Heart Rate Parameters as a Biomarker for Epileptogenesis," Epilepsy Res., 100(1-2): 59-66, 2012.

Lathers et al., "Synchronization of Cardiac Autonomic Neural Discharge with Epileptogenic Activity: The Lockstep Phenomenon," Electroencephalography Clin. Neurophysiol., 67(3):247-59, Sep. 1987.

Leutmezer et al., "Electrocardiographic Changes at the Onset of Epileptic Seizures," Epilepsia, 44(3):348-54, Mar. 2003.

Massé et al., "Miniaturized Wireless ECG Monitor for Real-Time Detection of Epileptic Seizures," ACM Transactions on Embedded Computing Systems, 12(4):102, Jun. 2013.

Mockenhaupt et al., "Manifestation and Outcome of Severe Malaria in Children in Northern Ghana," Am. J. Trop. Med. Hyg., 71(2):167-72, Aug. 2004.

Moridani et al., "Heart Rate Variability as a Biomarker for Epilepsy Seizure Prediction," Bratislava Med. J., 118(1):3-8, 2017.

Ogawa et al., "Left Stellate Ganglion and Vagal Nerve Activity and Cardiac Arrhythmias in Ambulatory Dogs With Pacing-Induced Congestive Heart Failure," J. Am. Coll. Cardiol., 50(4):335-43, Jul. 2007.

Oppenheimer et al., "Insular Cortex Stimulation Produces Lethal Cardiac-Arrhythmias—a Mechanism of Sudden-Death," Brain Res., 550:115-21, May 1991.

Oppenheimer et al., "Cardiac Chronotropic Organization of the Rat Insular Cortex," Brain Res., 533(1):66-72, Nov. 1990.

Pavei et al, "Early Seizure Detection Based on Cardiac Autonomic Regulation Dynamics," Front. Physiol., 8:765, Oct. 2017.

(56) References Cited

OTHER PUBLICATIONS

Peng et al., "Fractal Mechanisms and Heart Rate Dynamics: long range correlations and their breakdown with disease," J. Electrocardiol., 28:59-65, Jan. 1995.

Pitkänen et al., "Development of Epilepsy after Ischaemic Stroke" The Lancet Neurol., 15(2):185-97, Feb. 2016.

Pitkänen et al., Advances in the Development of Biomarkers for The Lancet Neurol., 15(8):843-56, Jul. 2016.

Ronkainen et al., "Suppressed Circadian Heart Rate Dynamics in Temporal Lobe Epilepsy." J. Neurol. Neurosurg. Psychiatry, 76(10):1382-6, Sep. 2005.

Rosenblueth, and Simeone, "The Interrelations of Vagal and Accelerator Effects on the Cardiac Rate." Am. J. Physiol., 110(1):42-55, Jun. 1934.

Schraeder and Lathers, "Cardiac Neural Discharge and Epileptogenic Activity in the Cat: An Animal Model for Unexplained Death." Life Sci., 32(12):1371-82, Mar. 1983.

Schuele et al., "Video-Electrographic and Clinical Features in Patients with Ictal Asystole." Neurology, 69(5):434-41, Jul. 2007.

Sedigh-Sarvestani et al.., "Rapid Eye Movement Sleep and Hippocampal Theta Oscillations Precede Seizure Onset in the Tetanus Toxin Model of Temporal Lobe Epilepsy." J. Neurosci., 34(4):1105-14, Jan. 2014.

Sevcencu et al., "Changes in Vagus Nerve Activity Associated with Ictal Tachycardia in Pigs." Epilepsy Res., 128: 52-60, Dec. 2016.

Ssentongo et al., "A Murine Model to Study Epilepsy and SUDEP Induced by Malaria Infection." Sci. Rep., 7:43652, Mar. 2017.

Sunderam et al., "Improved Sleep-Wake and Behavior Discrimination Using MEMS Accelerometers." J. Neurosci. Methods, 163(2): 373-83, Jul. 2007.

Tan et al., "Neural Mechanisms of Paroxysmal Atrial Fibrillation and Paroxysmal Atrial Tachycardia in Ambulatory Canines." Circulation, 118(9):916-25, Aug. 2008.

Tasker and Vitali, "Continuous Infusion, General Anesthesia and Other Intensive Care Treatment for Uncontrolled Status Epilepticus." Cur. Opin. Pediatr., 26(6):682-9, Dec. 2014.

Uradu et al., "Skin Sympathetic Nerve Activity Precedes the Onset and Termination of Paroxysmal Atrial Tachycardia and Fibrillation," Heart Rhythm, 14(7):964-71, Jul. 2017.

Van der Lende et al., "Cardiac Arrhythmias during or after Epileptic Seizures," J. Neurol. Neurosu. Pyschiatry, 87(1):69-74, Jan. 2016.

Van Elmpt et al., "A Model of Heart Rate Changes to Detect Seizures in Severe Epilepsy," Seizure 15(6):366-75, Sep. 2006.

Warner and Cox, "A Mathematical Model of Heart Rate Control by Sympathetic and Vagus Efferent Information," Simulation. 3(1):63-71. Jul. 1964.

Yacoub et al., "Cardiac Function and Hemodynamics in Kenyan Children with Severe Malaria." Crit. Care Med., 38(3):940-5, Mar. 2010.

Zafeiriou et al., "Characteristics and Prognosis of Epilepsy in Children with Cerebral Palsy." J. Child Neurol., 14(5):289-94, May 1999.

* cited by examiner

| Cohort | Number Chronically Recorded | Total Number Recorded with Epilepsy | Epilepsy Rate of recorded | Seizure Latency Range Post-Infection (Days) |
|---|---|---|---|---|
| SW-PbNK65 | 6 (17) | 4 (13) | 0.67±0.2 (0.76±0.1) | 39-115 (29-139) |
| SW-PbANKA | 1 (10) | 1 (7) | 1 (0.7±0.14) | 94 (22-105) |
| C57BL/6-PbANKA | 4 (12) | 3 (9) | 0.75±0.2 (0.75±0.12) | 39-92 (38-95) |
| CBA-PbANKA | 2 (4) | 1 (3) | 0.5±0.5 (0.75±0.22) | 99 (54-116) |

FIG. 15

BIOLOGICAL MARKER AND METHODS

CROSS-REFERENCE TO RELATED APPLICATIONS

This application is a continuation of U.S. application Ser. No. 16/396,316 (now U.S. Pat. No. 11,141,097), filed Apr. 26, 2019 titled "BIOLOGICAL MARKER AND METHODS", which claims priority to and the benefit of U.S. Provisional Application Ser. No. 62/663,213, filed Apr. 26, 2018 titled "BIOLOGICAL MARKER AND METHODS". The disclosure of the prior applications is considered part of (and is incorporated by reference in) the disclosure of this application.

STATEMENT AS TO FEDERALLY SPONSORED RESEARCH

This invention was made with government support under Grant No. EB019804 awarded by the National Institute of Health. The Government has certain rights in the invention.

TECHNICAL FIELD

This invention relates to biological markers, and more particularly to methods and systems, including no-invasive methods and systems, for monitoring biological markers for neurologic diseases and methods and systems for determining brain-periphery temporal associations useful as biomarkers. This invention also relates to a behavioral state-independent representation of cardiac activity, and more particularly to systems and methods for generating the behavioral state-independent representation of cardiac activity, and use of the behavioral state-independent representation of cardiac activity in methods of identifying cardiac events and brain-periphery, e.g., brain-cardiac, temporal associations useful as biomarkers.

BACKGROUND

Biological markers, or biomarkers, can provide objective, measurable, and reproducible indications of physiological state, including disease development, progression, phenotype, prognosis, interventional outcomes, and other factors. For many neurologic diseases, such as acquired epilepsies, science has not yet produced reliable biomarkers. Measurement and observation of known brain biomarkers for some neurologic diseases with known biomarkers is often invasive and costly. Many neurologic diseases develop over long periods of time, yet methods and systems for long term monitoring of neurologic disease biomarkers remains impractical or unreliable.

Cardiac measurements have been investigated as potential biomarkers of neurologic diseases. However, the behavioral-state dependence of available cardiac measurements limits the applicability of such measurements. Some available cardiac measurements require limited-time monitoring, limited behavioral state monitoring, and have low resolution (averaging across multiple heartbeats).

SUMMARY

This document provides methods, including, in some implementations, non-invasive methods, and systems for monitoring biological markers of neurologic diseases in a mammal. In some implementations, the methods and systems are based on the interaction, temporal association, or coincidence of brain activity and periphery activity in a mammal.

This document also provides a behavioral state-independent representation of cardiac activity that can be used in systems and methods for identifying cardiac events and brain-periphery, e.g., brain-cardiac, temporal associations useful as biomarkers of neurologic disease in a mammal. This document also provides methods and systems for generating a behavioral state-independent representation of cardiac activity.

Some exemplary methods described herein include computer-implemented methods for generating a behavioral state-independent representation of cardiac activity, computer-implemented methods for determining a brain-periphery temporal association between target brain activity and target periphery activity, methods for identifying statistically significant cardiac events in a mammal, methods for estimating the risk of occurrence of a physiological event, methods for preventing physiological events, methods for evaluating the effectiveness of an intervention measure, and methods for detecting brain-periphery coincidence in a mammal.

Some exemplary systems and devices useful in implementing one or more of these methods and other methods include computer systems, computer-readable media, physiological sensing systems, and physiological event warning systems.

The subject matter disclosed herein includes computer-implemented methods. The methods can be performed by systems of one or more computers in one or more locations. In some aspects, the systems have one or more processors and one or more computer-readable media encoded with instructions that, when executed by the one or more processors, cause the processors to perform the method. Some aspects include just the computer-readable media encoded with instructions that cause performance of the method when executed.

In one aspect, a method is provided for characterizing heart fluctuations, comprising: receiving, by at least one device, physiological data that describes cardiac activity of a mammal over a period of time, wherein the at least one device comprises a computer-processor and computer-memory; identifying, by the at least one device, two or more reference points in the physiological data; determining, by the at least one device, one or more intervals wherein each interval is an interval between a unique set of two of the reference points; processing, by the at least one device, the one or more intervals to generate one or more cardiac activity feature representations, wherein a distribution of the cardiac activity feature representations of the mammal over the period of time is independent of the mammal's behavioral state during the period of time, wherein processing the one or more intervals comprises determining for each interval a discrete estimate of the logarithmic derivative of the one or more intervals at a selected reference time, proportional to the difference in the interval before and after each selected reference time determined over a first time window, normalized by the average interval over a second time window, and wherein processing the one or more intervals comprises determining dlnRR at any time, T, using first window length $\tau_1$ and second window length $\tau_2$, according to the equation:

$$dlnRR(T)_{\tau_1,\tau_2} \stackrel{def}{=} \frac{1}{\tau_1} \frac{\overline{RRI}_{\tau_1}(T+\tau_1/2) - \overline{RRI}_{\tau_1}(T-\tau_1/2)}{\overline{RRI}_{\tau_2}(T)} \text{ wherein}$$

-continued $$\overline{RRI}_{\tau_1}(T) = \frac{\tau_1}{N_{RR,\tau_1}(T)}$$

$$\overline{RRI}_{\tau_2}(T) = \frac{\tau_2}{N_{RR,\tau_2}(T)}$$

$N_{RR,\tau_i}(T) \stackrel{def}{=}$ fractional number of intervals $\in [T - \tau_i/2, T + \tau_i/2]$, and wherein the fractional number of intervals include partial intervals that remain inside the first or second time windows; and providing, by the at least one device, an indication of the cardiac activity feature representations of the mammal over the period of time.

This and other implementations can optionally further include one or more of the following features. The method can further comprise processing, by the at least one device, the cardiac activity feature representations to generate an estimated distribution of the cardiac activity feature representations of the mammal over the period of time; providing, by the at least one device, an indication of the distribution of the cardiac activity feature representations of the mammal over the period of time; identifying, by the at least one device, a threshold range within the distribution based on the distribution; providing, by the at least one device, an indication of the threshold range; identifying, by the at least one device, one or more cardiac activity feature representations that are outside of a predetermined range in the distribution to generate a set of one or more target cardiac activity feature representations; and providing, by the at least one device, an indication of the one or more target cardiac activity feature representations outside of the predetermined range in the distribution. Each of the one or more target cardiac activity feature representations can describe a single heartbeat of the mammal. The physiological data can be ECG data and the reference points can correspond to one or more morphological feature representations of an ECG of the mammal. The morphological feature representations can be selected from a T-wave peak, a P-wave peak, a R-wave peak, an onset of a P-wave, an onset of Q, and an end of a T-wave. At least one of the two or more reference points can be representative of at least one feature of a QRS complex or at least one feature within a QRS complex of the mammal. The reference points can be R wave peaks. The one or more intervals can include at least one RR interval. $\tau_1$ can be greater than or equal to 100 ms. $\tau_1$ can be greater than or equal to 1 second. $\tau_1$ can be about 0.5 seconds and $\tau_2$ can be about 1 second. $\tau_1$ can be from about 10 to about 20 seconds and $\tau_2$ can be about 30 seconds. The mammal can be human, mouse, or rat.

In another aspect, a method is provided for estimating the risk of occurrence of a physiological event in a mammal prior to the occurrence of the physiological event, comprising: obtaining brain activity data that describes brain activity of the mammal over a first period of time; obtaining peripheral activity data that describes peripheral activity of the mammal over a second period of time; receiving, by at least one device, brain data from a brain activity measurement device that describes brain activity of a mammal over the first period of time; receiving, by the at least one device, periphery data from a peripheral activity measurement device that describes peripheral activity of a mammal over the second period of time; generating, by the at least one device, one or more brain feature representations based on the brain data; generating, by the at least one device, one or more periphery feature representations based on the periphery data; generating, by the at least one device, one or more brain statistical distributions of the one or more brain feature representations; generating, by the at least one device, one or more periphery statistical distributions of the one or more periphery feature representations; identifying, by the at least one device, one or more brain feature representations that fall outside of a predetermined range in the brain statistical distribution to generate a set of one or more target brain feature representations; identifying, by the at least one device, one or more periphery feature representations that fall outside of a predetermined range in the periphery statistical distribution to generate a set of one or more target periphery feature representations; determining, by the at least one device, a brain-periphery temporal association between the one or more target brain feature representations and the one or more target periphery feature representations; determining, by the at least one device, an estimate of risk of a future physiological event based on the brain-periphery temporal association; and providing, by the at least one device, an indication of the estimate of risk of the future physiological event.

This and other implementations can optionally further include one or more of the following features. The periphery data can be ECG data; receiving the periphery data can comprise receiving, by at least one device, physiological data that describes cardiac activity of a mammal over a period of time; identifying, by the at least one device, two or more reference points in the physiological data; determining, by the at least one device, one or more intervals wherein each interval is an interval between a unique set of two of the reference points; processing, by the at least one device, the one or more intervals to generate one or more cardiac activity feature representations, wherein a distribution of the cardiac activity feature representations of the mammal over the period of time is independent of the mammal's behavioral state during the period of time, wherein processing the one or more intervals comprises determining for each interval a discrete estimate of the logarithmic derivative of the one or more intervals at a selected reference time, proportional to the difference in the interval before and after each selected reference time determined over a first time window, normalized by the average interval over a second time window, and wherein processing the one or more intervals comprises determining dlnRR at any time, T, using first window length $\tau_1$ and second window length $\tau_2$, according to the equation:

$$dlnRR(T)_{\tau_1,\tau_2} \stackrel{def}{=} \frac{1}{\tau_1} \frac{\overline{RRI}_{\tau_1}(T + \tau_1/2) - \overline{RRI}_{\tau_1}(T - \tau_1/2)}{\overline{RRI}_{\tau_2}(T)} \text{ wherein}$$

$$\overline{RRI}_{\tau_1}(T) = \frac{\tau_1}{N_{RR,\tau_1}(T)}$$

$$\overline{RRI}_{\tau_2}(T) = \frac{\tau_2}{N_{RR,\tau_2}(T)}$$

$N_{RR,\tau_i}(T) \stackrel{def}{=}$ fractional number of intervals $\in [T - \tau_i/2, T + \tau_i/2]$, and wherein the fractional number of intervals include partial intervals that remain inside the first or second time windows. The brain activity data can be EEG data and the EEG data can be EEG line length data. The periphery data can be ECG data; receiving the periphery data can comprise receiving, by at least one device, physiological data that describes cardiac activity of a mammal over a period of time; identifying, by the at least one device, two or more reference points in the physiological data; determining, by the at least one device, one or more intervals wherein each interval is an interval between a unique set of two of the reference points; processing, by the at least one device, the one or more intervals to generate one or more cardiac activity feature representations, wherein a distribution of the cardiac activity feature representations of the mammal over the period of time is independent of the mammal's behavioral state during the period of time, wherein processing the one or more intervals comprises determining for each interval a discrete estimate of the logarithmic derivative of the one or more intervals at a selected reference time, proportional to the difference in the interval before and after each selected reference time determined over a first time window, normalized by the average interval over a second time window, and wherein processing the one or more intervals comprises determining dlnRR at any time, T, using first window length $\tau_1$ and second window length $\tau_2$, according to the equation:

$$dlnRR(T)_{\tau_1,\tau_2} \stackrel{def}{=} \frac{1}{\tau_1} \frac{\overline{RRI}_{\tau_1}(T+\tau_1/2) - \overline{RRI}_{\tau_1}(T-\tau_1/2)}{\overline{RRI}_{\tau_2}(T)} \text{ wherein}$$

$$\overline{RRI}_{\tau_1}(T) = \frac{\tau_1}{N_{RR,\tau_1}(T)}$$

$$\overline{RRI}_{\tau_2}(T) = \frac{\tau_2}{N_{RR,\tau_2}(T)}$$

$$N_{RR,\tau_i}(T) \stackrel{def}{=} \text{fractional number of intervals} \in [T - \tau_i/2, T + \tau_i/2],$$

and wherein the fractional number of intervals include partial intervals that remain inside the first or second time windows; and providing, by the at least one device, an indication of the cardiac activity feature representations of the mammal over the period of time; and the physiological event can be selected from the onset of acquired epilepsy, a seizure, and sudden unexpected death in epilepsy (SUDEP). The mammal can be human, mouse, or rat.

In one aspect, a computer-implemented method is provided, comprising receiving, by a system of one or more computers, physiological data that describes cardiac activity of a mammal over a period of time; identifying, by the system, two or more reference points in the physiological data; determining, by the system, one or more intervals wherein each interval is an interval between a unique set of two of the reference points; processing, by the system, the one or more intervals to generate one or more cardiac activity feature representations, wherein a distribution of the cardiac activity feature representations of the mammal over the period of time is independent of the mammal's behavioral state during the period of time; and providing, by the system, an indication of the cardiac activity feature representations of the mammal over the period of time.

In another aspect, one or more non-transitory computer-readable media are provided, encoded with instructions that, when executed by one or more processors of a system, cause the one or more processors to perform operations comprising receiving, by a system of one or more computers, physiological data that describes cardiac activity of a mammal over a period of time; identifying, by the system, two or more reference points in the physiological data; determining, by the system, one or more intervals wherein each interval is an interval between a unique set of two of the reference points; processing, by the system, the one or more intervals to generate one or more cardiac activity feature representations, wherein a distribution of the cardiac activity feature representations of the mammal over the period of time is independent of the mammal's behavioral state during the period of time; and providing, by the system, an indication of the cardiac activity feature representations of the mammal over the period of time.

These and other implementations can optionally further include one or more of the following features.

The method or operations can further comprise processing, by the system, the cardiac activity feature representations to generate an estimated distribution of the cardiac activity feature representations of the mammal over the period of time; and providing, by the system, an indication of the distribution of the cardiac activity feature representations of the mammal over the period of time. The method or operations can further comprise identifying, by the system, a threshold range within the distribution based on the distribution; and providing, by the system, an indication of the threshold range. The method or operations can further comprise identifying, by the system, one or more cardiac activity feature representations that are outside of a predetermined range in the distribution to generate a set of one or more target cardiac activity feature representations; and providing, by the system, an indication of the one or more target cardiac activity feature representations outside of the predetermined range in the distribution. The method or operations can further comprise quantifying, by the system, the magnitude of the one or more target cardiac activity feature representations; and providing, by the system, an indication of the magnitude of the one or more target cardiac activity feature representations. The method or operations can further comprise quantifying, by the system, the frequency of the one or more target cardiac activity feature representations; and providing, by the system, an indication of the frequency of the one or more target cardiac activity feature representations. The method or operations can further comprise providing, by the system, a plot of the magnitude of the one or more target cardiac activity feature representations over the period of time. The method or operations can further comprise providing, by the system, a plot of the frequency of the one or more target cardiac activity feature representations over the period of time.

The predetermined range can be based on the threshold range. The predetermined range can be the threshold range.

Each of the one or more target cardiac activity feature representations can describe a single heartbeat of the mammal. The physiological data can be representative of an electrophysiologic pattern of the cardiac function of the mammal. The physiological data can be selected from electrocardiogram (ECG) data, blood pressure data, and photoplethysmography (PPG) data. The physiological data can be ECG data and wherein the reference points correspond to one or more morphological feature representations of an ECG of the mammal. The morphological feature representations can be selected from a T-wave peak, a P-wave peak, a R-wave peak, an onset of a P-wave, an onset of Q, and an end of a T-wave.

In some implementations, at least one of the two or more reference points can be representative of at least one feature of a QRS complex or at least one feature within a QRS complex of the mammal. In some implementations, the reference points can be R wave peaks. In some implementations, the one or more intervals include at least one RR interval.

In some implementations, the one or more intervals can be selected from an interval between two successive reference points and an interval between two successive like reference points. In some implementations, the period of time can range from about 15 minutes to about 200 days.

In some implementations, processing the one or more intervals can comprise determining for each interval a discrete estimate of the logarithmic derivative of the one or more intervals at a selected reference time, proportional to the difference in the interval before and after each selected reference time determined over a first time window, normalized by the average interval over a second time window. In some implementations, the first time window can be at least 100 ms. In some implementations, the first time window is at least 1 second. In some implementations, the first time window is selected from a window of from about 100 ms to about 500 ms and a window of from about 750 ms to about 5000 ms. In some implementations, the second time window is greater than first time window. In some implementations, the second time window is twice the length of the first time window. In some implementations, the first and second time windows are sliding time windows.

In some implementations, the mammal is human. In some implementations, mouse. In some implementations, the mammal is rat.

In another aspect, a computing system is provided, comprising one or more processors; and one or more computer-readable media as described herein.

In another aspect, a system is provided, comprising one or more electrodes for recording electrocardiographic (ECG) signals from a mammal; and a computing system as described herein.

In another aspect, a method is provided for identifying statistically significant cardiac events in a mammal over a period of time, wherein the cardiac events are independent of the mammal's behavioral state during the period of time, the method comprising obtaining physiological data that describes cardiac activity of the mammal over a period of time; receiving, by a system of one or more computers, the physiological data that describes cardiac activity of a mammal over a period of time; identifying, by the system, two or more reference points in the representation of cardiac activity; determining, by the system, one or more intervals wherein each interval is an interval between a unique set of two of the reference points; processing, by the system, the one or more intervals to generate one or more cardiac activity feature representations, wherein a distribution of the cardiac activity feature representations of the mammal over the period of time is independent of the mammal's behavioral state during the period of time; processing, by the system, the cardiac activity feature representations to generate an estimated distribution of the cardiac activity feature representations of the mammal over the period of time; identifying, by the system, one or more cardiac activity feature representations that are outside of a predetermined range in the distribution to generate a set of one or more target cardiac activity feature representations; and providing, by the system, an indication of the one or more target cardiac activity feature representations outside of the predetermined range in the distribution.

In some implementations, the method further includes quantifying, by the system, the magnitude of the one or more target intervals. In some implementations, processing the one or more intervals includes determining for each of one or more selected reference times a discrete estimate of the logarithmic derivative of the one or more intervals at the selected reference time, proportional to the difference in the interval before and after each selected reference time determined over a first time window, normalized by the average interval over a second time window.

In some implementations of the method, the physiological data is selected from electrocardiogram (ECG) data, blood pressure data, and photoplethysmography (PPG) data. In some implementations, the physiological data was obtained one or more physiologic sensors that are integrated with or communicatively coupled to a smartphone, a tablet computer, a watch body, a watch band, or a wearable patch.

In another aspect, a computer-implemented method, comprising receiving, by a system of one or more computers, brain data from a brain activity measurement device that describes brain activity of a mammal over a first period of time; receiving, by the system, periphery data from a peripheral activity measurement device that describes peripheral activity of a mammal over a second period of time; generating, by the system, one or more brain feature representations based on the brain data; generating, by the system, one or more periphery feature representations based on the periphery data; generating, by the system, one or more brain statistical distributions of the one or more brain features; generating, by the system, one or more periphery statistical distributions of the one or more periphery feature representations; identifying, by the system, one or more brain feature representations that fall outside of a predetermined range in the brain statistical distribution to generate a set of one or more target brain feature representations; identifying, by the system, one or more periphery feature representations that fall outside of a predetermined range in the periphery statistical distribution to generate a set of one or more target periphery feature representations; determining, by the system, a brain-periphery temporal association between the one or more target brain feature representations and the one or more target periphery feature representations; and providing, by the system, an indication of the temporal association.

In another aspect, one or more non-transitory computer-readable media encoded with instructions that, when executed by one or more processors of a system, cause the one or more processors to perform operations comprising receiving, by a system of one or more computers, brain data from a brain activity measurement device that describes brain activity of a mammal over a first period of time; receiving, by the system, periphery data from a peripheral activity measurement device that describes peripheral activity of a mammal over a second period of time; generating, by the system, one or more brain feature representations based on the brain data; generating, by the system, one or more periphery feature representations based on the periphery data; generating, by the system, one or more brain statistical distributions of the one or more brain features; generating, by the system, one or more periphery statistical distributions of the one or more periphery feature representations; identifying, by the system, one or more brain feature representations that fall outside of a predetermined range in the brain statistical distribution to generate a set of one or more target brain feature representations; identifying, by the system, one or more periphery feature representations that fall outside of a predetermined range in the periphery statistical distribution to generate a set of one or more target periphery feature representations; determining, by the system, a brain-periphery temporal association between the one or more target brain feature representations and the one or more target periphery feature representations; and providing, by the system, an indication of the temporal association.

These and other implementations can optionally further include one or more of the following features.

The method or operations can further comprise determining, by the system, a quantification of the brain-periphery temporal association; and providing, by the system, an indication of the quantification of the brain-periphery temporal association. The method or operations can further comprise determining a brain-periphery coincidence rate of one or more target brain feature representations and one or more target periphery feature representations; and providing, by the system, and indication of the brain-periphery coincidence.

In some implementations, determining the temporal association can comprise comparing all brain feature-periphery feature pairs of one or more target brain feature representations and one or more target periphery feature representations. In some implementations, comparing all brain feature-periphery feature pairs can comprise comparing brain feature-periphery feature pairs within a predetermined time window. In some implementations, the predetermined time window can be from about 10 ms to about 2 seconds.

In some implementations, determining the temporal association comprises selecting one or more target brain feature representations; identifying a predetermined target time window around each of the selected brain feature representations; and determining the incidence of one or more target periphery feature representations within each predetermined time window. In some implementations, the predetermined time window can be from about 10 ms to about 2 seconds.

The method or operations can further comprise receiving, by the system, data from a physiological measurement device confirming the occurrence of a physiological event. The method or operations can further comprise determining, by the system, an association between the physiological event and the brain-periphery temporal association. The method or operations can further comprise providing, by the system, a quantification of the association between the physiological event and the brain-periphery temporal association. The method or operations can further comprise determining, by the system, a modified predetermined range for the brain statistical distribution based on at least one of the quantification of the brain-periphery temporal association and the quantification of the association between the physiological event and the brain-periphery temporal association. The method or operations can further comprise determining, by the system, a modified predetermined range for the periphery statistical distribution based on at least one of the quantification of the brain-periphery temporal association and the quantification of the association between the physiological event and the brain-periphery temporal association.

The method or operations can further comprise receiving, by a system of one or more computers, brain data from a brain activity measurement device that describes brain activity of a mammal over a first period of time; receiving, by the system, periphery data from a peripheral activity measurement device that describes peripheral activity of a mammal over a second period of time; identifying, by the system, one or more brain feature representations within the brain data; identifying, by the system, one or more periphery feature representations within the periphery data; generating, by the system, one or more brain statistical distributions of the one or more brain feature representations; generating, by the system, one or more periphery statistical distributions of the one or more periphery feature representations; identifying, by the system, one or more brain feature representations that fall outside of the modified predetermined range in the brain statistical distribution to generate a set of one or more target brain feature representations; identifying, by the system, one or more periphery feature representations that fall outside of the modified predetermined range in the periphery statistical distribution to generate a set of one or more target periphery feature representations; determining, by the system, a brain-periphery temporal association between the one or more target brain feature representations and the one or more target periphery feature representations; and providing, by the system, an indication of the temporal association.

In some implementations, the one or more periphery statistical distribution can be independent of behavioral state.

The method or operations can further comprise providing, by the system, an estimate of risk of a future physiological event based on the brain-periphery temporal association. The method or operations can further comprise providing, by the system, an estimate of risk of a future physiological event based on the quantification of the brain-periphery temporal association. The method or operations can further comprise providing, by the system, a plot of the magnitude of the brain-periphery temporal association over the period of time. The method or operations can further comprise providing, by the system, a plot of the frequency of the brain-periphery temporal association over the period of time. The method or operations can further comprise providing, by the system, an estimate of risk of a future physiological event based on a trend in the magnitude of brain-periphery temporal association. The method or operations can further comprise providing, by the system, an estimate of risk of a future physiological event based on a trend in the frequency of the brain-periphery temporal association. The method or operations can further comprise providing, by the system, an estimate of the magnitude of a future physiological event based on the trend in the brain-periphery temporal association.

In some implementations, the brain activity data can be selected from electroencephalography (EEG) data and electrocorticography (ECoG) data. In some implementations, the brain activity data is EEG data and the EEG data is EEG line length data. In some implementations, the periphery activity data can be selected from cardiac data, muscle movement data, nerve activity data, pupil dilation data, and body movement data. In some implementations, the periphery data is cardiac data and the cardiac data is selected from electrocardiogram (ECG) data, blood pressure data, and photoplethysmography (PPG) data. In some implementations, the periphery data is ECG data and wherein receiving the periphery data comprises a computer-implemented method described herein, such as receiving, by a system of one or more computers, physiological data that describes cardiac activity of a mammal over a period of time; identifying, by the system, two or more reference points in the physiological data; determining, by the system, one or more intervals wherein each interval is an interval between a unique set of two of the reference points; processing, by the system, the one or more intervals to generate one or more cardiac activity feature representations, wherein a distribution of the cardiac activity feature representations of the mammal over the period of time is independent of the mammal's behavioral state during the period of time; and providing, by the system, an indication of the cardiac activity feature representations of the mammal over the period of time.

In some implementations, the periphery data is muscle movement data and the muscle movement data is selected from electromyography (EMG) data, and limb or hand acceleration data. In some implementations, the periphery data is EMG data and the EMG data is stomach EMG data. In some implementations, the periphery data is nerve activity data and the nerve activity data is selected from nerve conduction data, and vagal nerve activity data. In some implementations, the periphery data is body movement data and the body movement data is selected from hand acceleration data, limb acceleration data, and perspiration data.

In some implementations, the physiological event is selected from the onset of acquired epilepsy, an epileptic seizure, sudden unexpected death in epilepsy (SUDEP), hydrocephalous, sepsis, and onset of cerebral palsy.

In another aspect, a computing system is provided, comprising one or more processors; and one or more computer-readable media as described herein. In another aspect, a system is provided comprising a device for recording brain activity data from a mammal; a device for recording peripheral activity from a mammal; and a computing system described herein.

In another aspect, a method for estimating the risk of occurrence of a physiological event in a mammal prior to the occurrence of the physiological event, comprising obtaining brain activity data that describes brain activity of the mammal over a first period of time; obtaining peripheral activity data that describes peripheral activity of the mammal over a second period of time; receiving, by a system of one or more computers, brain data from a brain activity measurement device that describes brain activity of a mammal over the first period of time; receiving, by the system, periphery data from a peripheral activity measurement device that describes peripheral activity of a mammal over the second period of time; generating, by the system, one or more brain feature representations based on the brain data; generating, by the system, one or more periphery feature representations based on the periphery data; generating, by the system, one or more brain statistical distributions of the one or more brain feature representations; generating, by the system, one or more periphery statistical distributions of the one or more periphery feature representations; identifying, by the system, one or more brain feature representations that fall outside of a predetermined range in the brain statistical distribution to generate a set of one or more target brain feature representations; identifying, by the system, one or more periphery feature representations that fall outside of a predetermined range in the periphery statistical distribution to generate a set of one or more target periphery feature representations; determining, by the system, a brain-periphery temporal association between the one or more target brain feature representations and the one or more target periphery feature representations; determining, by the system, an estimate of risk of a future physiological event based on the brain-periphery temporal association; and providing, by the system, an indication of the estimate of risk of the future physiological event.

The method can further comprise determining, by the system, a quantification of the brain-periphery temporal association; wherein providing the estimate of risk of a future physiological event is based on the quantification of the brain-periphery temporal association. The method can further comprise determining, by the system, an estimate of the timing of a future physiological event based on the brain-periphery temporal association; and providing an indication of the estimate of the timing of the future physiological event. The method can further comprise determining, by the system, an estimate of the timing of a future physiological event based on the quantification of the brain-periphery temporal association; and providing an indication of the estimate of the timing of the future physiological event.

In some implementations, the periphery statistical distribution is independent of behavioral state. In some implementations, the brain activity data is electroencephalography (EEG) data. In some implementations, the brain activity data is EEG data and the EEG data is EEG line length data.

In some implementations, the periphery activity data is selected from cardiac data, muscle movement data, nerve activity data, pupil dilation data, and body movement data. In some implementations, the periphery data is cardiac data and the cardiac data is selected from electrocardiogram (ECG) data, blood pressure data, and photoplethysmography (PPG) data. In some implementations, the periphery data is muscle movement data and the muscle movement data is selected from electromyography (EMG) data and limb or hand acceleration data. In some implementations, the periphery data is EMG data and the EMG data is stomach EMG data. In some implementations, the periphery data is nerve activity data and the nerve activity data is selected from nerve conduction data, and vagal nerve activity data. In some implementations, the periphery data is body movement data and the body movement data is selected from hand acceleration data, limb acceleration data, and perspiration data.

In some implementations, the physiological event is selected from the onset of acquired epilepsy, an epileptic seizure, sudden unexpected death in epilepsy (SUDEP), hydrocephalous, sepsis, and onset of cerebral palsy.

In some implementations, the periphery data is ECG data; receiving the periphery data comprises a method described herein; and the physiological event is selected from the onset of acquired epilepsy, an epileptic seizure, and sudden unexpected death in epilepsy (SUDEP).

In some implementations, the peripheral activity data was obtained from a peripheral activity measurement device that is integrated with or communicatively coupled to a smartphone, a tablet computer, a watch body, a watch band, or a wearable patch.

The method can further comprise displaying, on a display device, an output indicative of the estimate of risk of the physiological event. The method can further comprise displaying, on a display device, an output indicative of the estimate of risk of the physiological event.

In another aspect, a seizure advisory system is provided, comprising one or more electrodes for recording electroencephalographic (EEG) signals from a mammal; one or more devices for recording cardiac data from a mammal; and a computing system comprising one or more processors; and one or more computer-readable media encoded with instructions that, when executed by the one or more processors, cause the one or more processors to perform operations comprising: receiving, by the system, EEG data from the mammal over a first period of time; receiving, by the system, cardiac data from the mammal over a second period of time; generating, by the system, one or more EEG feature representations based on the EEG data; generating, by the system, one or more cardiac feature representations based on the cardiac data; generating, by the system, one or more EEG statistical distributions of the one or more EEG feature representations; generating, by the system, one or more cardiac statistical distributions of the one or more cardiac feature representations according methods described herein; identifying, by the system, one or more EEG feature representations that fall outside of a predetermined range in the EEG statistical distribution to generate a set of one or more target EEG feature representations; identifying, by the system, one or more cardiac feature representations that fall outside of a predetermined range in the cardiac statistical distribution to generate a set of one or more target cardiac feature representations; determining, by the system, a brain-cardiac temporal association between the one or more EEG feature representations and the one or more cardiac feature representations; determining, by the system, an estimate of risk of a future seizure based on the brain-cardiac temporal association; and providing, by the system, an automatic warning based on the estimated risk of a future seizure.

In some implementations, the one or more computer-readable media cause the one or more processors to perform operations further comprising determining, by the system, a quantification of the brain-periphery temporal association, wherein providing the estimate of risk of a future physiological event is based on the quantification of the brain-periphery temporal association.

In some implementations, the one or more computer-readable media cause the one or more processors to perform operations further comprising determining, by the system, an estimate of the timing of a future physiological event based on the brain-periphery temporal association; and providing an automatic warning indicating the estimate of the timing of the future physiological event.

In some implementations, the one or more computer-readable media cause the one or more processors to perform operations further comprising determining, by the system, an estimate of the timing of a future physiological event based on the quantification of the brain-periphery temporal association; and providing an automatic warning indicating the estimate of the timing of the future physiological event.

In some implementations, the one or more cardiac statistical distributions are independent of behavioral state. In some implementations, the one or more devices for recording cardiac data comprise one or more electrodes for recording electrocardiographic (ECG) signals from a mammal; one or more blood pressure sensors, one or more optical sensors for recording photoplethysmography (PPG) data from a mammal. In some implementations, the EEG data is EEG line length data.

In some implementations, at least one of the EEG data and the cardiac data is obtained from one or more physiologic sensors that are integrated with or communicatively coupled to a smartphone, a tablet computer, a watch body, a watch band, or a wearable patch.

In another aspect, a method of preventing a physiological event is provided, comprising estimating the risk of occurrence of a physiological event in a mammal according to methods described herein; and applying at least one intervention measure that is commensurate with the prevention of the physiological event.

In some implementations, estimating the risk and applying the intervention measure are performed automatically. In some implementations, the physiological event is the onset of acquired epilepsy and the at least on intervention measure is an anti-epileptogenesis therapy. In some implementations, the physiological event is an epileptic seizure and the at least on intervention measure is an anti-epileptic drug (AED).

In another aspect, a method of evaluating the effectiveness of an intervention measure is provided, comprising estimating the risk of occurrence of a physiological event in a mammal according to methods described herein; applying at least one intervention measure that is commensurate with the prevention of the physiological event; and determining the effectiveness of the intervention measure.

In some implementations, estimating the risk and apply the intervention measure are performed automatically. In some implementations, the physiological event is the onset of acquired epilepsy and the at least on intervention measure is an anti-epileptogenesis therapy. In some implementations, the physiological event is an epileptic seizure and the at least on intervention measure is an anti-epileptic drug (AED).

In another aspect, a method for detecting a brain-periphery coincidence in a mammal is provided, comprising obtaining brain activity data that describes brain activity of the mammal over a period of time; obtaining peripheral activity data that describes peripheral activity of the mammal over a period of time; processing the peripheral activity data to generate independent peripheral activity data that is independent of behavioral state; and using a machine-learning model to detect presence of a brain-periphery coincidence in the mammal based on the brain activity data and the peripheral activity data.

In some implementations of the methods described herein, processing the one or more intervals comprises determining dlnRR at any time, T, using first window length $\tau_1$ and second window length $\tau_2$, according to the equation:

$$dlnRR(T)_{\tau_1,\tau_2} \stackrel{def}{=} \frac{1}{\tau_1} \frac{\overline{RRI}_{\tau_1}(T + \tau_1/2) - \overline{RRI}_{\tau_1}(T - \tau_1/2)}{\overline{RRI}_{\tau_2}(T)} \text{ wherein}$$

$$\overline{RRI}_{\tau_1}(T) = \frac{\tau_1}{N_{RR,\tau_1}(T)}$$

$$\overline{RRI}_{\tau_2}(T) = \frac{\tau_2}{N_{RR,\tau_2}(T)}$$

$$N_{RR,\tau_i}(T) \stackrel{def}{=} \text{fractional number of intervals} \in [T - \tau_i/2, T + \tau_i/2],$$

and wherein the fractional number of intervals include partial intervals that remain inside the first or second time windows. In some implementations, $\tau_1$ is greater than or equal to 100 ms. In some implementations, $\tau_1$ is greater than or equal to 1 second. In some implementations, $\tau_1$ is about 0.5 seconds and $\tau_2$ is about 1 second. In some implementations, $\tau_1$ is from about 10 to about 20 seconds and $\tau_2$ is about 30 seconds.

In another aspect, a computer-implemented method is provided, comprising receiving, by a system of one or more computers, brain data from a brain activity measurement device that describes brain activity of a mammal over a first period of time; receiving, by the system, periphery data from a peripheral activity measurement device that describes peripheral activity of a mammal over a second period of time; generating, by the system, one or more brain feature representations based on the brain data; generating, by the system, one or more periphery feature representations based on the periphery data; generating, by the system, one or more brain statistical distributions of the one or more brain features; generating, by the system, one or more periphery statistical distributions of the one or more periphery feature representations; identifying, by the system, one or more brain feature representations that fall outside of a predetermined range in the brain statistical distribution to generate a set of one or more target brain feature representations; identifying, by the system, one or more periphery feature representations that fall outside of a predetermined range in the periphery statistical distribution to generate a set of one or more target periphery feature representations; identifying, by the system, a probability of the one or more target periphery feature representations within a defined time window of one or more of the target brain feature representations to generate an estimated cumulative probability distribution; determining, by the system a brain-periphery temporal association between the one or more target brain feature representations and the one or more target periphery feature representations based on the estimated cumulative probability distribution; and providing, by the system, an indication of the temporal association.

In another aspect, a computer-implemented method is provided, comprising receiving, by a system of one or more computers, brain data from a brain activity measurement device that describes brain activity of a mammal over a first period of time; receiving, by the system, periphery data from a peripheral activity measurement device that describes peripheral activity of a mammal over a second period of time; generating, by the system, one or more brain feature representations based on the brain data; generating, by the system, one or more periphery feature representations based on the periphery data; generating, by the system, one or more brain statistical distributions of the one or more brain features; generating, by the system, one or more periphery statistical distributions of the one or more periphery feature representations; identifying, by the system, one or more brain feature representations that fall outside of a predetermined range in the brain statistical distribution to generate a set of one or more target brain feature representations; identifying, by the system, one or more periphery feature representations that fall outside of a predetermined range in the periphery statistical distribution to generate a set of one or more target periphery feature representations; identifying, by the system, a probability of the one or more target brain feature representations within a defined time window of one or more of the target periphery feature representations to generate an estimated cumulative probability distribution; determining, by the system a brain-periphery temporal association between the one or more target brain feature representations and the one or more target periphery feature representations based on the estimated cumulative probability distribution; and providing, by the system, an indication of the temporal association.

The systems and methods described herein provide several advantages. First, the systems and methods are non-invasive in comparison to traditional methods for observing brain biomarkers. This aspect also decreases the cost of the methods and systems described herein as compared to traditional methods.

Second, some implementations of the systems and methods described herein provide behavioral state-independent representations of disease biomarkers and therefore allow for long-term monitoring of physiological factors, or biomarkers, providing a more complete and meaningful view of disease state, phenotype, and prognosis than traditional methods. Because traditional methods lack the behavioral state-independence, such methods have traditionally been restricted to periods of relatively stationary behavior such as observed or imposed rest. The behavioral state-independence of some implementations of the systems and methods described herein therefore allow for patient observation in natural states and over longer periods of time. One advantage of observation over long periods of times and lack of restriction to stationary states means an ability to observe potentially rare events, or events that don't occur during the particular restricted states. Such monitoring can provide or illuminate a robust biomarker for all aspects of diseases, including development, prognosis, etc., and a more complete understanding of the disease, its progression, phenotype, and prognosis, etc. as compared to traditional methods and systems.

Third, some implementations provide for generation of a behavioral state-independent representation of cardiac activity with single heart beat resolution. While some implementations of the systems and methods described herein allow for long-term monitoring, the systems and methods can also provide for reduced monitoring and data needs due to the high single beat resolution.

Fourth, some implementations of the systems and methods described herein allow for early monitoring of a mammal, in some cases even prior to development of a disease. Such earlier monitoring of biomarkers as compared to traditional methods can allow for, in some cases, prevention or slowed progression of a disease or physiological event. Early monitoring can help identify patients at risk of developing certain neurologic diseases, introduce early and effective interventions to prevent or reduce disease progression or symptoms, and evaluate therapeutic efficacy of intervention measures.

Fifth, some implementations of the systems and methods described herein are tailorable to specific patients or patient populations, thereby allowing for more accurate and personal understanding of disease and implementation of preventative or palliative measures.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

For the terms "for example" and "such as," and grammatical equivalences thereof, the phrase "and without limitation" is understood to follow unless explicitly stated otherwise. As used herein, the term "about" is meant to account for variations due to experimental error. As used herein, the singular forms "a," "an," and "the" are used interchangeably and include plural referents unless the context clearly dictates otherwise.

As used herein, "brain activity" includes electrical activity of the brain and/or hemodynamic responses to electrical activity of the brain, and can be measured from electrical or magnetic signals, or from optical measurements. Electrical measurements of brain activity can include electrical potentials measured from scalp (such as classic scalp electroencephalography (EEG)), or from implanted electrodes below the scalp, within the cranium outside or within the dura, or from electrodes implanted within the parenchyma of the brain (depth electrodes). Electrical measurements can also be acquired from electrodes within the brain vasculature. Magnetic measurements can be made from electrical coils outside the head (standard magentoenephelography MEG), micro-coils or other magnetic sensors (including MEMs magnetic field sensors) outside, on or within the head. Optical measurements can include those based on hemodynamic responses to brain activity (such as functional near infra-red spectroscopy, fNIRs), dynamic light scattering, and the like.

As used herein, "periphery activity" includes activity of one or more body parts (e.g., organs, muscles, limbs, and the like) controlled by the central nervous system, and can include activity of the heart or respiration, muscle activity, limb motion, pupil dilation, activity of the stomach or intestinal walls, bladder or urethral or sphincter tone, and activity of the sympathetic or parasympathetic systems.

As used herein, "cardiac activity" includes descriptions of cycle-by-cycle function (e.g., pumping) of the heart, and can include the timing of each heartbeat or the details of each phase of each heartbeat. Cardiac activity can be measured directly from the heart, from the electrical signals emitted when different parts of the heart contract (electrocardiogram ECG), or from measures of blood in the circulatory system i.e. from optical measures (photoplethysmography) or changes in blood pressure.

As used herein, the term "distribution" is meant in the statistical sense to describe the probability of observing a variable, metric, or feature value. This is sometimes also referred to as the probability density function or probability distribution function. Distributions functions can describe the probability density of observing a specific value, or the total probability of values within a range. Distributions herein can include univariate and multivariate distributions. For univariate features (i.e. features with a single value), an exemplary distribution can include the cumulative distribution function (CDF), which is the probability over the range of values less than or equal to a value. Exemplary probability distribution can include the central limit theorem, which states that sums of randomly chosen variables will tend or approximate to a Gaussian-shaped or normal distribution. As one example, where the measured variable is a cardiac RR-interval for a mouse, the distribution can, in some implementations, be the ideal probability density of observing a particular value of RR interval from the mouse, and the total probability of observing an RR interval in a given range.

In such example, the cumulative distribution of RR-values would be the total probability of observing an RR-value less than or equal to a given RR-value. Some exemplary distributions utilized in some implementations herein include probability function of RR interval values, the probability of dlnRR, the probability of EEG line length, and the like. "Estimated distribution" includes a representation of the probability density distribution empirically estimated from data. One example of an estimated distribution in some implementations herein includes, for an RR interval from a mouse, a histogram of values of RR interval (number of values observed within specified ranges of RR-interval value) observed from the mouse in a finite time (e.g., over one hour, over one day, etc.), divided by the total number of RR-intervals observed in that time. Some exemplary estimated distributions utilized in some implementations herein include the distribution of dlnRR estimated from a time window of measurement (e.g., one hour, one day, etc.) and the distribution of EEG line length estimated from a time window of measurement (e.g., one hour, one day, etc.).

As used herein, the terms "behavioral independence," "independent of behavioral state," "state-independent," "state of vigilance independent," "independent of state of vigilance," are used interchangeably. These terms and similar terms and phrases indicate that the subject values and/or representations are essentially unaffected by the mammal's behavioral state, such as, e.g., whether the mammal is sleeping, stationary, exercising, anxious, etc. Statistically, these terms and similar terms and phrases indicate that the distributions of the subject values or representations (e.g., cardiac activity feature representations) are indistinguishable when separated by state. For example, a subject value or representation is state-independent when the value or representation associated with the 90th %, 95th %, and/or 99th % rank is essentially the same in a behaviorally conditioned group as compared to a behaviorally unconditioned group (e.g. sleeping mammal group versus average mammal group sleeping or doing one or more activities) within a given time period or number of measurements (e.g., across 1000 or more events, such as heartbeats). As further example, the means and variances of the subject values or representations remain the same in a behaviorally conditioned group as compared to a behaviorally unconditioned group.

As used herein, the term "statistically significant event" or "statistically significant cardiac event" includes events that are unexpected from random sampling of the distribution. An example of a statistically significant event, e.g. a cardiac event, is repeated observation of a cardiac event with a feature representation value (e.g., dlnRR) in the upper 1% of the distribution (i.e. with cumulative probability >99%) more frequently than 1% of the time.

As used herein, the term "coincidence" refers to events that occur together, and more specifically events that are observed to occur within a predefined range of time with respect to each other. In one exemplary implementation described herein, a coincidence can include the occurrence of a long RR interval between one and two seconds after a short brain discharge "Coincidence rate" refers to the probably per time or per single event that a coincidence between two events occur. In some exemplary implementations described herein, a coincidence rates can include the number of brain-heart event coincidences that occur per time period (e.g., per hour, per day, etc.).

Also herein, the recitations of numerical ranges by endpoints include all numbers subsumed within that range (e.g., 1 to 5 includes 1, 1.5, 2, 2.75, 3, 3.80. 4, 5, etc.). The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 15 is a table depicting chronic recording and analysis summary, according to the Examples described herein. Listed are the distribution of animals chronically recorded that met the criteria for analysis of brain-heart coincidences during epileptogenesis. Numbers in parentheses indicate total number of mice studied for development of epilepsy in cerebral malaria. For detailed description of model statistics, and mouse-parasite combinations see Ssentongo et al. 2017.[58] The epilepsy criteria were defined as observation of at least 2 seizures longer than 10 s and at least one seizure past day 26 post-infection. The subset of animals selected for further investigation of brain-heart interactions showed similar seizure rates and latencies to the larger cohorts studied for development of the post-cerebral malaria epilepsy model.

Like reference symbols in the various drawings indicate like elements.

DETAILED DESCRIPTION

This document provides systems, methods, and other techniques for non-invasive monitoring of biological markers in a mammal. In some implementations, methods and systems can be based on the interaction, temporal association, or coincidence of brain activity and periphery activity in a mammal. In some implementations, methods and systems can generate a behavioral state-independent representation of cardiac activity, including cardiac activity feature representations. In some implementations, a behavioral state-independent representation of cardiac activity and cardiac activity feature representations can be used in systems and methods for identifying cardiac events and/or brain-periphery, e.g., brain-cardiac, temporal associations useful as biomarkers of disease such as, e.g., neurologic disease, in a mammal. In some implementations, systems and methods for monitoring a biomarker can be used to generate an estimation of the risk of occurrence of a physiological event. In some implementations, systems and methods for monitoring a biomarker can be used for preventing physiological events such as through application of an intervention measure, and systems and methods for monitoring a biomarker can also be used for evaluating the effectiveness of an intervention measure. The mammal can be any mammal. In some implementations, the mammal can be selected from a human, a mouse, a rat, a non-human primate, a sheep, a pig, a dog, or a cat. Additional detail about these and other techniques is provided in the following description of FIGS. 1-6.

Figure 1:
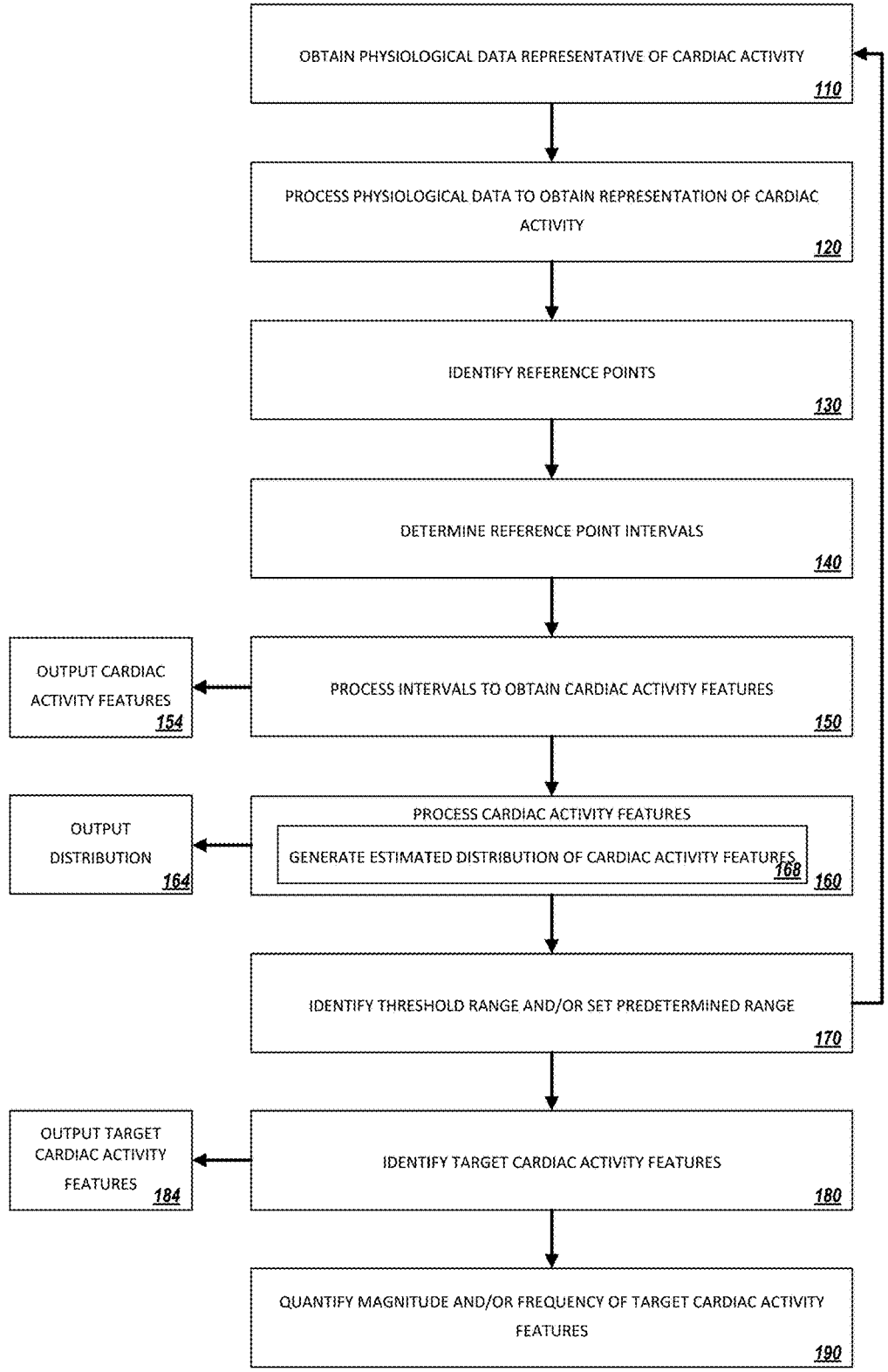
FIG. 1 is a flowchart of an example process for generating a behavioral state-independent representation of cardiac activity.

FIG. 1 is a flowchart of an example process 100 for generating a behavioral state-independent representation of cardiac activity. The process 100 can be performed by a computing system, e.g., system 210 of FIG. 2. At stage 110, the system obtains or receives physiological data representative of cardiac activity of a mammal over a period of time. The period of time can be chosen based on the particular disease or stage of disease being investigated, the particular cardiac events being investigated, the species of mammal, and the like. In some implementations, the period of time can be at least 5 minutes, at least 10 minutes, at least 15 minutes, at least one hour, or at least one day. In some implementations, the period of time can range from about 15 minutes to about 200 days or more. In some implementations, the period of time can range from about 15 minutes to about 5 days, from about 15 minutes to about 24 hours, from about 15 minutes to about 2 hours, from about 1 day to about 10 days, from about 10 days to about 40 days, or from about 1 hour to about 365 days. In some implementations, the period of time can be as long as necessary to observe development or understanding of a disease, or to predict an event or event type. In some implementations, such as for seizure prediction, the period of time can range from about 15 minutes to about 5 days, or from about 15 minutes to about 1 day. In some implementations, such as for estimation of the risk of developing acquired epilepsy (epileptogenesis), the period of time can range from about 1 hour to about 7 days, or from about 1 hour to about 200 days. In some implementations, such as for estimation of the risk of or an estimation of the timing of occurrence of a future physiological event, the period of time can range from about 1 hour to about 25 years. For example, in some implementations, such as for estimation of the risk of or an estimation of the timing of occurrence of a seizure in an epileptic individual, the period of time can range from about 1 hour to about 1 day. As another example, in some implementations, such as for estimation of the risk of or an estimation of the timing of occurrence of a first spontaneous seizure after a brain insult (i.e. onset of epilepsy), the period of time can range from about 1 week to about 25 years.

The physiological data can be representative of an electrophysiologic pattern of the cardiac function of the mammal. Exemplary electrophysiologic pattern of the cardiac function can include QRS complexes, heartbeats, and the like. The physiological data can, in some implementations, be selected from electrocardiogram (ECG) data, blood pressure data, and photoplethysmography (PPG) data. ECG data can include one or more channels that each represents the ECG signal for a respective lead of an ECG procedure, and data from each channel can be temporally aligned. The physiological data may span two or more cardiac cycles of the patient or mammal, and the two or more cardiac cycles can include one or more portions of a cardiac cycle of the patient or mammal. Obtaining or receiving the physiological data can, in some implementations, include processing the data to obtain a graphical or tabular representation of the data, such as, e.g., a graphical representation of an ECG of a mammal, a table of individual heartbeats and their associated temporal classifications, and the like.

At stage 130, the system identifies two or more reference points in the physiological data. In some implementations, each reference point corresponds to a unique reference time. In some implementations, the reference points can be input or selected by a user through, e.g., a graphical user interface and/or a user input interface of the system. In some implementations, the system identifies the reference points based on predetermined values, operations, and/or image recognition. In some implementations, the reference points can correspond to one or more data points representative of a known cardiac event, such as, e.g., an individual heartbeat, contraction of a heart ventricle, a change in blood pressure, and the like. In some implementations, the physiological data is ECG data and the reference points correspond to one or more morphological features of an ECG of the mammal. In some implementations, the physiological data is data other than ECG data and the reference points correspond to data points representative of one or more morphological features of an ECG of the mammal. The morphological features of the ECG of the mammal can include at least a T-wave peak, a P-wave peak, a R-wave peak, an onset of a P-wave, an onset of Q, and an end of a T-wave. In some implementations, the two or more reference points are representative of at least one feature of a QRS complex or at least one feature within a QRS complex of the mammal. In some implementations, the reference points are R wave peaks.

At stage 140, the system determines one or more intervals between reference points, wherein each interval is an interval between a unique set of two reference points. In some implementations, the intervals are selected from an interval between two successive reference points and an interval between two successive like reference points. "Like reference points" indicates that the reference points represent the same aspect or event in the physiologic data, such as, e.g., the same peak on two different ECG waveforms. In some implementations, the reference points are R-wave peaks and the one or more intervals include at least one RR interval. In some implementations, the one or more intervals include at least one PR interval. In some implementations, the one or more intervals include at least one QT interval.

At stage 150, the system processes the one or more intervals to generate one or more cardiac feature representations. In some implementations, the cardiac feature representations are intervals or derived from the intervals. In some implementations, the cardiac feature representations are representative of a cardiac event such as, e.g., a single heartbeat. Optionally, the process can include stage 154, wherein the system provides an indication, such as, e.g., a graphical or tabular output of the cardiac feature representations of the mammal over the period of time. In some implementations, the output can be a physical output, an image on a graphical user interface, an audible output, or the like.

In some implementations, processing the one or more intervals includes a univariate determination or a multivariate determination. In some implementations, processing the one or more intervals includes determining for each interval a discrete estimate of the logarithmic derivative of the one or more intervals at a selected reference time, proportional to the difference in the interval before and after each selected reference time calculated over a first time window, normalized by the average interval over a second time window. In some implementations, one or more selected reference times can include at least one selected reference time per RR interval. In some implementations, the first time window can be equivalent to about one to five times the typical RR interval of the mammal. The first time window can, in some implementations, be at least about 100 ms, at least about 200 ms, at least about 0.5 seconds, at least about 1 second, at least about 2 seconds, at least about 5 seconds, at least about 30 seconds, or at least about 100 seconds. In some implementations, the first time window can range from about 50 ms to about 5 seconds, from about 100 ms to about 3 seconds, from about 200 ms to about 3 seconds from about 0.3 seconds to about 0.8 seconds, from about 0.4 seconds to about 0.6 seconds, from about 1 second to about 100 seconds, from about 5 seconds to about 50 seconds, from about 8 seconds to about 30 seconds, from about 10 seconds to about 20 seconds, from about 10 seconds to about 16 seconds, from about 14 seconds, to about 20 seconds, or from about 9 seconds to about 21 seconds. In some implementations, the first time window can be about 100 ms, 0.4 seconds, about 0.5 seconds, about 0.6 seconds, about 1 second, about 9 seconds, about 10 seconds, about 11 seconds, about 15 seconds, about 19 seconds, about 20 seconds, or about 21 seconds. In some implementations, the first time window is selected from a window of from about 100 ms to about 500 ms and a window of from about 750 ms to about 5000 ms. In some implementations, the first second window is selected from a window of from about 200 ms to about 5000 ms and a window of from about 1500 ms to about 50,000 ms. In some implementations, the first time window can be chosen based on particular variables such as the particular species of mammal, the reference point type, the goal of the investigation, and the like. For example, in some implementations the first time window may correspond to a range of time that is the expected average heart beat rate of the particular species of mammal. In some implementations, the first time window can correspond to a range expected to contain two to three average heartbeats. In some implementations, the first time window can correspond to a range expected to contain a minimum of one average heartbeat (e.g., based on a mean heart rate). In some implementations, the second time window is greater than first time window. In some implementations, the second time window is twice the length of the first time window. In some implementations, the second time window can be an average respiratory period (e.g., mean or median time between breaths), which can, in some implementations be from about 6 to about 10 heartbeats. In some implementations, the second time window can be equivalent to about two to about ten times the typical RR interval of the mammal, or about five to about ten times the typical RR interval of the mammal. The second time window can, in some implementations, be at least about 200 ms, at least about 400 ms, at least about 1 second, at least about 2 seconds, at least about 4 seconds, at least about 10 seconds, at least about 30 seconds, or at least about 100 seconds. In some implementations, the first time window can range from about 100 ms to about 10 seconds, from about 200 ms to about 6 seconds, from about 0.5 seconds to about 6 seconds from about 0.3 seconds to about 1.5 seconds, from about 0.4 seconds to about 1.5 seconds, from about 0.8 seconds to about 1.2 seconds, from about 0.9 seconds to about 1.1 seconds, from about 5 seconds to about 50 seconds, from about 8 seconds to about 45 seconds, from about 10 seconds to about 40 seconds, from about 20 seconds to about 40 seconds, from about 30 seconds to about 40 seconds, from about 25 seconds to about 35 seconds, or from about 29 seconds to about 31 seconds. In some implementations, the second time window can be about 0.5 seconds, about 0.9 seconds, about 1 second, about 1.1 seconds, about 29 seconds, about 30 seconds, or about 31 seconds. In some implementations, the first and second time windows are sliding time windows.

In some implementations, processing the one or more intervals comprises determining dlnRR, a representation of a discrete estimate of the logarithmic derivative of the one or more intervals at a selected reference time. In some implementations, processing the one or more intervals comprises determining dlnRR at any time, T, using first window length $\tau_1$ and second window length $\tau_2$, according to the equation:

$$dlnRR(T)_{\tau_1,\tau_2} \stackrel{def}{=} \frac{1}{\tau_1} \frac{\overline{RRI}_{\tau_1}(T+\tau_1/2) - \overline{RRI}_{\tau_1}(T-\tau_1/2)}{\overline{RRI}_{\tau_2}(T)} \text{ wherein}$$

$$\overline{RRI}_{\tau_1}(T) = \frac{\tau_1}{N_{RR,\tau_1}(T)}$$

$$\overline{RRI}_{\tau_2}(T) = \frac{\tau_2}{N_{RR,\tau_2}(T)}$$

$$N_{RR,\tau_i}(T) \stackrel{def}{=} \text{fractional number of intervals} \in [T - \tau_i/2, T + \tau_i/2].$$

In some implementations, processing the one or more intervals comprises determining dlnRR at any time, T, using first window length $\tau_1$ equal to the second window length $\tau_2$, ($\tau_1 = \tau_2 = \tau$) with according to the equation:

$$dlnRR(T)_\tau \stackrel{def}{=} \frac{2}{\tau_1} \frac{\overline{RRI}(T+\tau/2) - \overline{RRI}(T-\tau/2)}{\overline{RRI}(T+\tau/2) + \overline{RRI}(T-\tau/2)} \text{ where}$$

$$\overline{RRI}(T) = \frac{\tau}{N_{RR}(T)}$$

$$N_{RR}(T) = \text{fractional number of intervals} \in [T-\tau/2, T+\tau/2],$$

where fractional number of intervals include partial intervals that remain inside the window. In the limit as $\tau \to 0$, if the derivative of RR-time series is defined, this representation becomes the derivative of the logarithm of the RR interval:

$$\lim_{\tau \to 0} dlnRR(T)_\tau \stackrel{def}{=}$$

$$\lim_{\tau \to 0} \frac{2}{\tau} \frac{\overline{RRI}\left(T+\frac{\tau}{2}\right) - \overline{RRI}\left(T-\frac{\tau}{2}\right)}{\overline{RRI}\left(T+\frac{\tau}{2}\right) + \overline{RRI}\left(T-\frac{\tau}{2}\right)} = \frac{\frac{d}{dT}\overline{RRI}(T)}{\overline{RRI}(T)} = \frac{d}{dT} \ln \overline{RRI}(T)$$

dlnRR is a local measure that is proportional to the normalized RR interval in the window length over which it is calculated.

In some implementations, such as where the mammal is a mouse having an average heart rate of 600 beats per minute, $\tau_1 \geq 100$ ms. In some implementations, where the mammal is a mouse, $\tau_1 = 0.5$ s, $\tau_2 = 1$ s. In some implementations, such as where the mammal is a human having an average heart rate of 60 beats per minute, $\tau_1 \geq 1$ s. In some implementations, where the mammal is human, $\tau_1 \in [10,20]$ s and $\tau_2 \geq 30$ s. In some implementations, $\tau_2$ can be based on the average breathing rate of a human mammal. In some implementations, $\tau_2$ can be from about 5 to about 12 seconds.

At stage 160, the system processes the cardiac activity feature representations and generates an estimated distribution of the cardiac activity feature representations of the mammal over the period of time at stage 168. The distribution can, in some implementations, be, e.g., a statistical distribution, such as a rank distribution, the probability density function, or the cumulative probability. In some implementations, the cumulative probability is equivalent to normalized rank. The distribution can be one-dimensional or multi-dimensional. In some implementations, the distribution is independent of the mammal's behavioral state during the period of time. Optionally, the process can include stage 164, wherein the system provides an indication, such as, e.g., a graphical or tabular output of the estimated distribution. In some implementations, the output can be a physical output, an image on a graphical user interface, an audible output, or the like.

At stage 170, the system identifies a predetermined range within the distribution with which to compare the cardiac activity feature representations within the distribution. In some implementations, the predetermined range can be a range determined by the system and/or selected by a user prior to generation of the distribution. In some embodiments, the predetermined range can be a range determined by the system and/or selected by a user based on one or more aspects of the generated distribution. In some implementations, the stage 170 involves an optional step of identifying, by the system, a threshold range within the distribution based on the distribution. In some implementations, the system can identify a threshold range based on the presence and magnitude of observable outlier values of cardiac activity feature representations within the distribution. In some implementations, the predetermined range is the threshold range. In such implementations, the threshold range can be determined by, e.g., statistical rank of the distribution. In some implementations, the predetermined range can be a 90%, 95%, or 99% range or threshold. For example, in some implementations, the predetermined range can be a 99% rank distribution range such that an outlier value is greater than or equal to 99%. In such exemplary implementations an outlier value is present in the upper 1% tail of the rank distribution. As another example, in some implementations, the predetermined or threshold range can be a 1% rank distribution range such that an outlier value is less than or equal to 1%. In such exemplary implementations, an outlier value can be present in the lower 1% tail of the rank distribution. In some implementations, the system can optionally provide an indication of the threshold and/or predetermined range (not shown).

In some implementations, the process 100 can optionally be used to build or train (e.g., via machine learning) a model for evaluation of physiological data. In such implementations of the process, stages 110-170 are used to identify or generate a modified threshold range or modified predetermined range. The modified threshold or predetermined range can then be provided as an output to a user or stored in a memory, e.g., on computer-readable media, for later use in process 100. The user can then return to stage 110 to repeat process 100 for the same, different, or new data using the modified threshold or predetermined range. In this manner, the predetermined range can be set to useful or statistically significant values specific to a chosen disease, group of mammals, or individual mammal or patient.

At stage 180, the system identifies one or more cardiac activity feature representations that fall outside of the predetermined range in the distribution and generates a set of one or more target cardiac activity representations. Optionally, the process can include stage 184, wherein the system provides an indication, such as, e.g., a graphical or tabular output of the target cardiac activity representations. In some implementations, the output can be a physical output, an image on a graphical user interface, an audible output, or the like. In some implementations, the target cardiac activity representations are representative of likely abnormal cardiac events or aberrations in the mammal's average cardiac activity. One advantage of the systems and methods described herein is that, while these likely abnormal cardiac events or aberrations in the mammal's average cardiac activity might not otherwise be detectable from reviewing a standard ECG, the processes and systems described herein both allow detection and eliminate the need to define an abnormal event in some manner in which it can be detected, instead providing a simple manner in which to identify the likely abnormal events. In some implementations, the system can be trained, e.g., through machine learning, and configured to identify a predetermined and/or threshold range suitable for the desired analysis.

Optionally, the process can further include stage 190, wherein the system quantifies the magnitude and/or frequency of the one or more target cardiac activity feature representations. Optionally, the process can include providing, by the system, an indication, such as, e.g., a graphical or tabular output of the magnitude and/or frequency of the one or more target cardiac activity feature representations. In some implementations, the system can optionally generate a plot (not shown) of the magnitude and/or frequency of the one or more target cardiac activity feature representations over the period of time.

Figure 2:
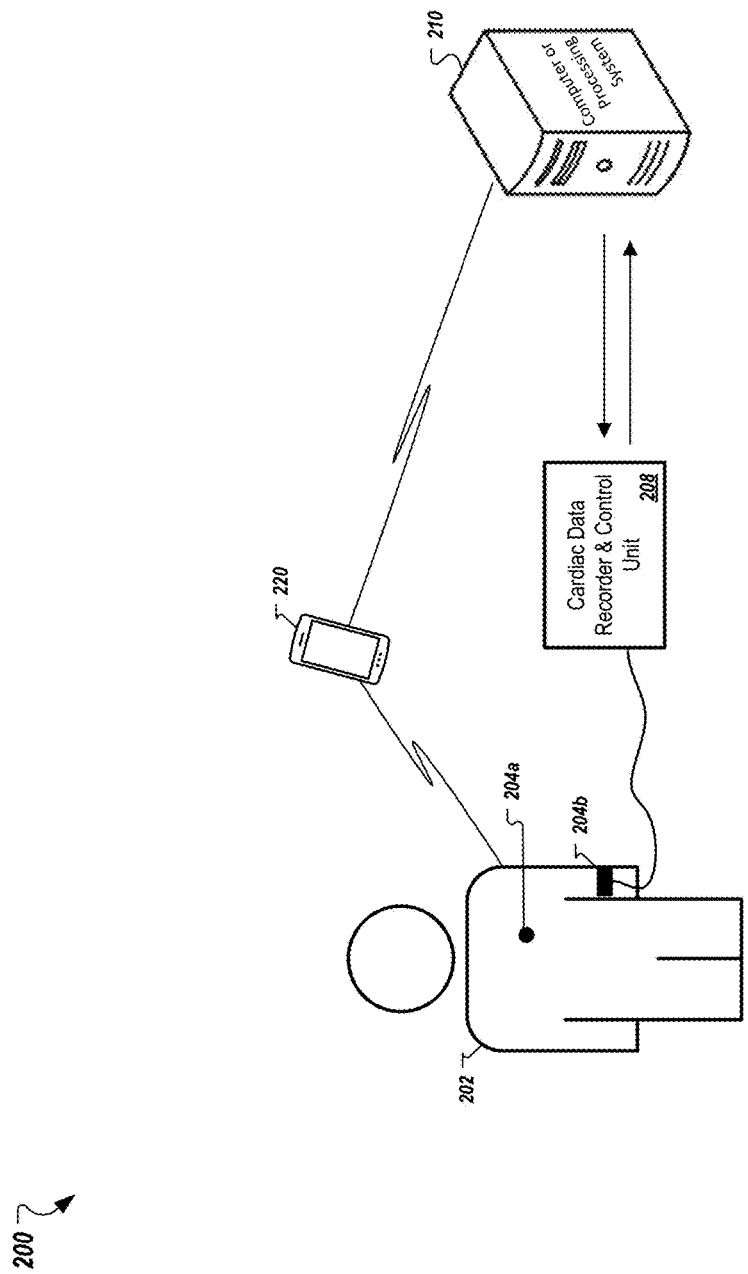
FIG. 2 is a conceptual diagram of an example system for recording and processing physiological data representative of cardiac activity, and using the data to generate a behavioral state-independent representation of cardiac activity.

FIG. 2 is a conceptual diagram of an example system 200 for recording and processing physiological data that describes cardiac activity of a mammal, and using the physiological data for generating a behavioral state-independent representation of cardiac activity of a subject mammal 202. For the purpose of this example, the subject 202 will be considered as a human, and more specifically as a patient of a healthcare provider. However, it should be understood that the description is not limited to this example. In other implementations, the subject 202 may be a human who is not specifically associated with a healthcare provider, or may be any other mammal, such as, e.g., a mouse, rat, or non-human primate.

One or more sensors 204a and/or 204b are disposed on a surface of the patient 202 to enable recording of signals or physiological data that describes cardiac activity of a mammal. In some implementations, the sensors can be, e.g., one or more ECG electrode leads affixed to a patient. In some implementations, the sensors can be selected from sensors that measure or provide an indication of changes in electrocardiogram (ECG) data, blood pressure data, and photoplethysmography (PPG) data. In some implementations, the physiological data can be obtained from one or more physiologic sensors that are integrated with or communicatively coupled to a smartphone, a tablet computer, a watch body, a watch band, or a wearable patch. For example, in some implementations, the patient 202 can manually contact a fixed pair of external electrodes or other sensors with his or her fingers, or the patient 202 may wear a watch, wristband, chest band, or other device that secures one or more electrodes or other sensors in position on the patient 202 to sense the patient's cardiac activity. A mobile computing device (e.g., smartphone 220) may be used by the patient 202 or a healthcare provider to configure aspects of the data recording procedure in a clinical or non-clinical setting.

The system 200 can further include a data recorder and control unit 206 for controlling and recording the physiological data from the sensors. In some implementations, data recording and/or controlling units can be integrated into one or more sensor devices and/or a mobile computing device (e.g., smartphone 220). The system 200 further includes a data processing system 210, and one or more input/output devices (e.g., smartphone 220). In some implementations, data processing system 210 can be integrated into one or more sensor devices and/or a mobile computing device (e.g., smartphone 220). For example, a wearable sensing device can, in some implementations, include the physiological data sensors, the data recording and control unit, the data processing system, and, optionally, one or more input/output interfaces.

The data recorder and controller unit 206 is communicably coupled to the processing system 210. The processing system 210 is a system of one or more computers, which may be distributed in one or more physical locations. System 210 may or may not be in the same physical location as the patient 202 and/or the data recorder and control unit 206. The system 210 may be coupled to peripheral devices such as a display screen (e.g., on smartphone 220) for presenting information to a user, patient, or healthcare provider, and an input interface (e.g., on smartphone 220) for receiving user inputs. Moreover, the system 210 may include a variety of components known to one of ordinary skill in the art that facilitate processing of physiological data in the processes described herein.

It should be understood that in some implementations, the physiological data can be recorded and processed simultaneously in real-time, or a delay can occur between the recording of the data and the processing. For example, the processing can be done using data recorded minutes, days, or even years prior to the processing. The data can be stored, e.g., on computer-readable media, for a length of time prior to the processing of the data.

Figure 3:
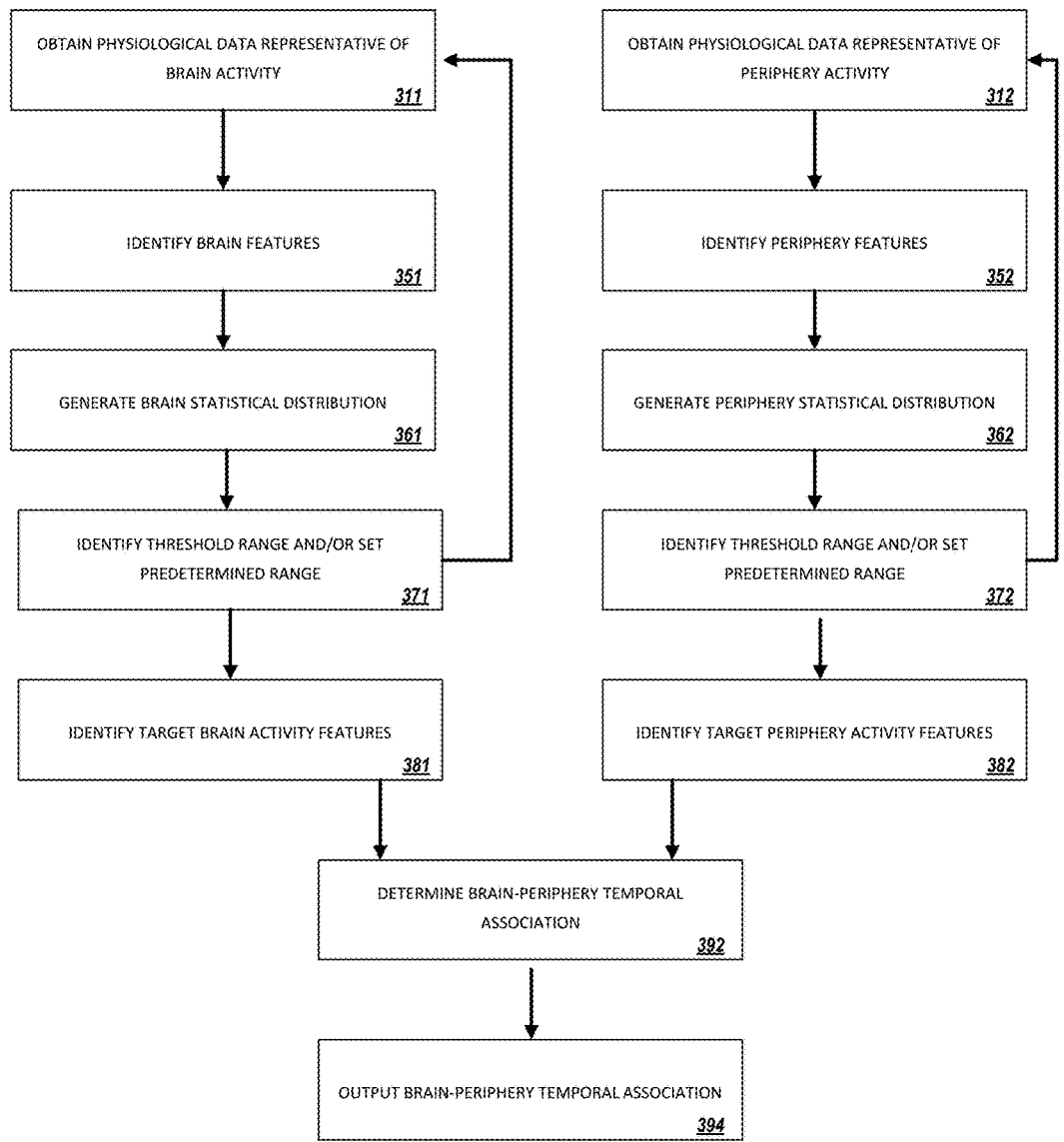
FIG. 3 is a flowchart of an example process for determining brain-periphery temporal associations.

FIG. 3 is a flowchart of an example process 300 for non-invasive monitoring of biological markers in a mammal. In some implementations, process 300 can generate an indication of a brain-periphery temporal association between brain physiological events and periphery physiological events. The process 300 can be performed by a computing system, e.g., system 410 of FIG. 4. At stage 311, the system obtains or receives brain data from a brain activity measurement device that describes brain activity of a mammal over a first period of time. At stage 312, the system obtains or receives periphery data from a peripheral activity measurement device that describes peripheral activity of a mammal over a second period of time. The first and second periods of time can be chosen based on the particular disease or stage of disease being investigated, the particular brain and/or periphery events being investigated, the species of mammal, and the like. In some implementations, the first and second periods of time can range from about 15 minutes to about 200 days, from about 15 minutes to about 2 days, from about 15 minutes to about 2 weeks, from about 1 to about 3 days, or from about 1 day to about 30 years. In some implementations, the data and any corresponding representations, predictions, or estimates can be continuously updated indefinitely. In some implementations, the first and second periods of time can be the same time length and/or the same time data. By same time data it is meant that the data recorded during the first and second periods of time can be superimposed on one another and represent the same points of time in the periods (e.g. simultaneously captured data). In some implementations, if the data is incomplete during the time periods, the univariate distributions can be used from each of the brain and periphery data to make ongoing estimates of the distribution (e.g., rank). In some implementations, overlapping periods can be used to estimate coincidence rates. In some implementations, the statistics of such estimates can be, within a normalization, the same as or similar to that of complete data.

The brain data can, in some implementations, be data obtained from electrical measurements of brain activity can include electrical potentials measured from scalp (such as classic scalp electroencephalography (EEG)), or from implanted electrodes below the scalp, within the cranium outside or within the dura, or from electrodes implanted within the parenchyma of the brain (depth electrodes). Electrical measurements can also be acquired from electrodes within the brain vasculature. Magnetic measurements can be made from electrical coils outside the head (standard magentoenephelography MEG), micro-coils or other magnetic sensors (including MEMs magnetic field sensors) outside, on or within the head. Optical measurements can include those based on hemodynamic responses to brain activity (such as functional near infra-red spectroscopy, fNIRs), dynamic light scattering, and the like. The brain data can, in some implementations, be representative of data selected from electroencephalographic (EEG) data and electrocorticography (ECoG) data. In some embodiments, the EEG data can be scalp EEG data, subdural EEG (sdEEG) data, or intracranial EEG (icEEG) data.

The periphery data can, in some implementations, be representative of data selected from cardiac data, muscle movement data, nerve activity data, pupil dilation data, and body movement data. In some implementations, muscle movement data is selected from hand or limb acceleration data and electromyography (EMG) data, such as, e.g., stomach EMG data. In some implementations, the periphery data is nerve activity data selected from nerve conduction data and vagal nerve activity data. In some implementations, the periphery data is body movement data is selected from hand acceleration data, limb acceleration data, and perspiration data. The periphery data can, in some implementations, be representative of cardiac activity of the mammal. The periphery data can, in some implementations, be representative of an electrophysiologic pattern of the cardiac function of the mammal. Exemplary electrophysiologic pattern of the cardiac function can include QRS complexes, heartbeats, and/or other heart rate variable data. The physiological data can, in some implementations, be selected from electrocardiogram (ECG) data, blood pressure data, and photoplethysmography (PPG) data. ECG data can include one or more channels that each represents the ECG signal for a respective lead of an ECG procedure, and data from each channel can be temporally aligned. The cardiac periphery data may span two or more cardiac cycles of the patient, and can include one or more portions of a cardiac cycle of the mammal. Obtaining or receiving the periphery data can, in some implementations, include processing the data to obtain a graphical or tabular representation of the data, such as, e.g., a graphical representation of an ECG of a mammal, a table of individual heart beats and their associated temporal classifications, and the like. In some implementations, receiving and/or processing the periphery data can include the process 100 of FIG. 1.

At stage 351, the system generates one or more brain feature representations based on the brain data. In some implementations, the brain feature representations include EEG line length ($EEG_L$) representations, short-term spectral band power, peak amplitude, frequencies in various bands, spike signatures, and the like. At stage 352, the system generates one or more periphery feature representations based on the periphery data. In some implementations, the periphery feature representations are selected from cardiac feature representations, muscle movement feature representations, nerve activity feature representations, and hand acceleration feature representations. In some implementations, the periphery feature can include activity of the heart or respiration, muscle activity, limb motion, pupil dilation, activity of the stomach or intestinal walls, bladder or urethral or sphincter tone, and/or activity of the sympathetic or parasympathetic systems. In some implementations, the periphery feature representations are cardiac feature representations representative of a cardiac event such as, e.g., a single heartbeat. Optionally, the process can include providing an indication, such as, e.g., a graphical or tabular output of the brain and/or periphery feature representations of the mammal over the period of time. In some implementations, the output can be a physical output, an image on a graphical user interface, an audible output, or the like.

In some implementations, generating one or more brain feature representations based on the brain data and/or generating one or more periphery feature representations based on the periphery data can include processing the respective brain or periphery data through a univariate determination or a multivariate determination. In some implementations, processing the periphery data includes determining a discrete estimate of the logarithmic derivative of the one or more intervals as described in process 100.

At stage 361, the system processes the brain activity feature representations and generates an estimated distribution of the brain activity feature representations of the mammal over the period of time. At stage 362, the system processes the periphery activity feature representations and generates an estimated distribution of the periphery activity feature representations of the mammal over the period of time. The brain and/or periphery distribution can, in some implementations, be, e.g., a statistical distribution, such as a rank distribution. The brain and/or periphery distribution can be one-dimensional or multi-dimensional. In some implementations, the brain and/or periphery distribution is independent of the mammal's behavioral state during the period of time. Optionally, the process can include providing an indication, such as, e.g., a graphical or tabular output of the estimated brain and/or periphery distribution. In some implementations, the output can be a physical output, an image on a graphical user interface, an audible output, or the like.

At stage 371, the system identifies a predetermined range within the distribution with which to compare the brain activity feature representations within the distribution. At stage 372, the system identifies a predetermined range within the distribution with which to compare the periphery activity feature representations within the distribution. In some implementations, the predetermined range can be a range determined by the system and/or selected by a user prior to generation of the brain and/or periphery distribution. In some embodiments, the predetermined range can be a range determined by the system and/or selected by a user based on one or more aspects of the generated distribution. In some implementations, stage 371 and/or 372 involves an optional step of identifying, by the system, a threshold range within the brain and/or periphery distribution based on the distribution. In some implementations, the system can identify a threshold range based on the presence and magnitude of observable outliers of brain and/or periphery activity feature representations within the distribution. In some implementations, the predetermined range is the threshold range. In such implementations, the threshold range can be determined by, e.g., statistical rank of the distribution. In some implementations, the predetermined range can be a 90%, 95%, or 99% range or threshold. For example, in some implementations, the predetermined range can be a 99% rank distribution range such that an outlier value is greater than or equal to 99%. In such exemplary implementations, an outlier value is present in the upper 1% tail of the rank distribution. As another example, in some implementations, the predetermined or threshold range can be a 1% rank distribution range such that an outlier value is less than or equal to 1%. In such exemplary implementations, an outlier value can be present in the lower 1% tail of the rank distribution. In some implementations, the system can optionally provide an indication of the threshold and/or predetermined range (not shown).

At stage 381, the system identifies one or more brain activity feature representations that fall outside of a predetermined range in the distribution and generates a set of one or more target brain activity representations. At stage 382, the system identifies one or more periphery activity feature representations that fall outside of a predetermined range in the distribution and generates a set of one or more target periphery activity representations. Optionally, the process can further include providing an indication, such as, e.g., a graphical or tabular output of the target brain and/or periphery activity representations. In some implementations, the output can be a physical output, an image on a graphical user interface, an audible output, or the like. In some implementations, the target brain and/or periphery activity representations are representative of likely abnormal brain and/or periphery events or aberrations in the mammal's average brain and/or periphery activity. Optionally, identifying one or more brain and/or periphery activity feature representations that fall outside of a predetermined range can include identifying, by the system, a predetermined range within the brain and/or periphery distribution with which to compare the brain and/or periphery activity feature representations within the distribution. In some implementations, the predetermined range can be a range determined by the system and/or selected by a user prior to generation of the distribution. In some embodiments, the predetermined range can be a range determined by the system and/or selected by a user based on one or more aspects of the generated distribution. In some implementations, identifying a predetermined range involves an optional step of identifying, by the system, a threshold range within the distribution based on the distribution. In some implementations, the system can identify a threshold range based on the presence and magnitude of observable outliers of brain and/or periphery activity feature representations within the distribution. In some implementations, the predetermined range is the threshold range. In such implementations, the threshold range can be determined by, e.g., statistical rank of the distribution. In some implementations, the predetermined range can be a 90%, 95%, or 99% range or threshold. For example, in some implementations, the predetermined range can be a 99% rank distribution range such that an outlier value is greater than or equal to 99%. In such exemplary implementations, an outlier value is present in the upper 1% tail of the rank distribution. As another example, in some implementations, the predetermined or threshold range can be a 1% rank distribution range such that an outlier value is less than or equal to 1%. In such exemplary implementations, an outlier value can be present in the lower 1% tail of the rank distribution. In such implementations, the system can optionally provide an indication of the threshold and/or predetermined range (not shown). In some implementations, the system can be trained, e.g., through machine learning, and configured to identify a predetermined and/or threshold range suitable for the desired analysis.

The process 300 further includes stage 392, wherein the system determines, a brain-periphery temporal association between the one or more target brain feature representations and the one or more target periphery feature representations. In some implementations, determining a temporal association includes determining a time relationship between the occurrence of a target brain feature representation and a target periphery feature representation. In some implementations, determining the temporal association includes comparing all brain feature-periphery feature representation pairs of one or more target brain feature representations and one or more target periphery feature representations. In some implementations, comparing all brain feature-periphery feature representation pairs includes comparing brain feature-periphery feature representation pairs within a predetermined time window. In some implementations, determining the temporal association can include selecting one or more target brain feature representations; identifying a predetermined target time window around each of the selected brain feature representations; and determining the incidence of one or more target periphery feature representations within each predetermined time window. In some implementations, determining the temporal association can include selecting one or more target periphery feature representations; identifying a predetermined target time window around each of the selected periphery feature representations; and determining the incidence of one or more target brain feature representations within each predetermined time window. In some implementations, the predetermined time window is from about 10 ms to about 2 seconds, from about 10 ms to about 100 ms, from about 1 second to about 2 seconds, or from about 0.5 seconds to about 2.5 seconds. In some implementations, the time window can be adjusted based on the peripheral system examined and/or the location of the sensors, such as, e.g., EEG electrodes. In some implementations, the predetermined time window is a window of time before the selected target brain and/or periphery feature representation. In some implementations, the predetermined time window is a window of time after the selected target brain and/or periphery feature representation. In some implementations, the predetermined time window is a window of time before and after the selected target brain and/or periphery feature representation.

The process 300 can optionally further include stage 394, wherein the system provides an indication, such as, e.g., a graphical or tabular output of the temporal association. In some implementations, the output can be a physical output, an image on a graphical user interface, an audible output, or the like. In some implementations, the process can further include determining whether the brain periphery temporal association between a given brain feature-periphery feature representation pair indicates a brain-periphery coincidence between the target brain feature representation and the target periphery feature representation and therefore between the brain event and periphery event of which the target brain feature representation and the target periphery feature representation are representative. In some implementations, coincidence is determined if the events occur within a specified time window with respect to each other. In some implementations, once events are detected from one type of activity (e.g., brain and/or periphery activity) the rank sum of feature representations of the other type of activity are reviewed. In some implementations, coincidence is determined by statistical probability excursions from random distribution of the occurrence of the two events. If a coincidence between a given target brain feature representation and a given target periphery feature representation is determined, the process can optionally further include determining a brain-periphery coincidence rate of the target brain-periphery feature representations. Coincidence rate describes the frequency of coincidences. In some implementations, coincidence rate can be determined by a conditional rank-sum approach. In some implementations, the coincidence rate can be the normalized rank-sum of the paired conditional distributions such that the greater the coincidence rate is, the stronger the correlation between brain and periphery activity is.

In some implementations, the process can optionally further include determining, by the system, a quantification of the brain-periphery temporal association. Optionally, the process can include providing, by the system, an indication, such as, e.g., a graphical or tabular output of the quantification of the brain-periphery temporal association.

In some implementations, the process 300 can optionally be used to build or train (e.g., via machine learning) a model for determination of brain-periphery temporal association, brain-periphery coincidence, and/or brain-periphery coincidence rate. In such implementations of the process, stages 311-371 and 312-372 are used to identify or generate a modified threshold range or modified predetermined range. The modified threshold or predetermined range can then be provided as an output to a user or stored in a memory, e.g., on computer-readable media, for later use in process 300. The user can then return to stages 311 and 312 to repeat process 300 for the same, different, or new data using the modified threshold or predetermined range. In this manner, the predetermined range can be set to useful or statistically significant values specific to a chosen disease, periphery measurement, group of mammals, or individual mammal or patient.

In some implementations, the process 300 can optionally be used to build or train (e.g., via machine learning) a model for determination of brain-periphery temporal association, brain-periphery coincidence, and/or brain-periphery coincidence rate that is associated with a separate physiological event such as a seizure, cardiac arrest, onset of a disease such as development of acquired epilepsy, or the like. In some implementations, the process can further include receiving, by the system, data from a physiological measurement device confirming the occurrence of a physiological event. In some implementations, the process can further include determining, by the system, an association between the physiological event and the brain-periphery temporal association. In some implementations, the process can further include determining, by the system, a quantification of the association between the physiological event and the brain-periphery temporal association. In some implementations, the process can further include determining, by the system, a modified predetermined range (e.g., stage 371) for the brain statistical distribution based on at least one of the quantification of the brain-periphery temporal association and the quantification of the association between the physiological event and the brain-periphery temporal association. In some implementations, the process can further include determining, by the system, a modified predetermined range (e.g., stage 372) for the periphery statistical distribution based on at least one of the quantification of the brain-periphery temporal association and the quantification of the association between the physiological event and the brain-periphery temporal association. In some implementations of the process, upon confirming an association between the physiological event and the brain-periphery temporal association, and/or upon determining a modified predetermined range for the brain and/or periphery statistical distribution, the modified threshold or predetermined range can then be provided as an output to a user or stored in a memory, e.g., on computer-readable media, for later use in process 300. The user can then return to stages 311 and 312 to repeat process 300 for the same, different, or new data based on the association between the physiological event and the brain-periphery temporal association, in some implementations using the modified threshold or predetermined range. In this manner, the predetermined range can be set to useful or statistically significant values specific to a chosen disease, periphery measurement, group of mammals, or individual mammal or patient.

In some implementations, once an association between the physiological event and the brain-periphery temporal association has been confirmed, the process can be used to predict and/or estimate the risk of a similar future physiological event based on, e.g., the occurrence of temporally associated, or coincident, target brain-periphery feature representations. In some implementations, the process can further include providing, by the system, an estimate of risk of a future physiological event based on the brain-periphery temporal association and/or the quantification of the brain-periphery temporal association. Optionally, the process can further include providing an indication, such as, e.g., a graphical or tabular output of the estimate of risk of the physiological event. In some implementations, the output can be a physical output, an image on a graphical user interface, an audible output, or the like. In some implementations, the processes and systems provide an early warning of a potential future physiological event so that protective measures may be taken to lessen the effect of the future physiological event, such as by ensuring a safe, fall-free environment for a seizure, or taking intervention measures, such as, e.g., anti-epileptic drugs in the case of an impending epileptic seizure, that lessen the event, prevent the event, or delay the event. In some implementations of the process, the system can provide a plot of the magnitude and/or frequency of the brain-periphery temporal association over the period of time. In some implementations of the process, the system can provide an estimate of risk of a future physiological event based on a trend in the magnitude and/or frequency of brain-periphery temporal association. In some implementations of the process, the system can provide an estimate of the timing of the future physiological event, such as how long a subject has before the physiological event will likely occur, giving the subject a valuable indication of how much time is available to prepare for or intervene against the future physiological event, which may affect the preparation decisions and/or choice of intervention methods and/or medications. In some implementations of the process, an indication of an estimate of risk of a future physiological event can also include an indication of the estimate of timing of the potential future physiological event.

In another implementation of a process similar to process 300, the process can include receiving, by a system of one or more computers, brain data from a brain activity measurement device that describes brain activity of a mammal over a first period of time; receiving, by the system, periphery data from a peripheral activity measurement device that describes peripheral activity of a mammal over a second period of time; generating, by the system, one or more brain feature representations based on the brain data; generating, by the system, one or more periphery feature representations based on the periphery data; generating, by the system, one or more brain statistical distributions of the one or more brain features; generating, by the system, one or more periphery statistical distributions of the one or more periphery feature representations; identifying, by the system, one or more brain feature representations that fall outside of a predetermined range in the brain statistical distribution to generate a set of one or more target brain feature representations; identifying, by the system, one or more periphery feature representations that fall outside of a predetermined range in the periphery statistical distribution to generate a set of one or more target periphery feature representations; identifying, by the system, a probability of the one or more target periphery feature representations within a defined time window of one or more of the target brain feature representations to generate an estimated cumulative probability distribution; determining, by the system a brain-periphery temporal association between the one or more target brain feature representations and the one or more target periphery feature representations based on the estimated cumulative probability distribution; and providing, by the system, an indication of the temporal association.

In another implementation of a process similar to process 300, the process can include receiving, by a system of one or more computers, brain data from a brain activity measurement device that describes brain activity of a mammal over a first period of time; receiving, by the system, periphery data from a peripheral activity measurement device that describes peripheral activity of a mammal over a second period of time; generating, by the system, one or more brain feature representations based on the brain data; generating, by the system, one or more periphery feature representations based on the periphery data; generating, by the system, one or more brain statistical distributions of the one or more brain features; generating, by the system, one or more periphery statistical distributions of the one or more periphery feature representations; identifying, by the system, one or more brain feature representations that fall outside of a predetermined range in the brain statistical distribution to generate a set of one or more target brain feature representations; identifying, by the system, one or more periphery feature representations that fall outside of a predetermined range in the periphery statistical distribution to generate a set of one or more target periphery feature representations; identifying, by the system, a probability of the one or more target brain feature representations within a defined time window of one or more of the target periphery feature representations to generate an estimated cumulative probability distribution; determining, by the system a brain-periphery temporal association between the one or more target brain feature representations and the one or more target periphery feature representations based on the estimated cumulative probability distribution; and providing, by the system, an indication of the temporal association.

Figure 4:
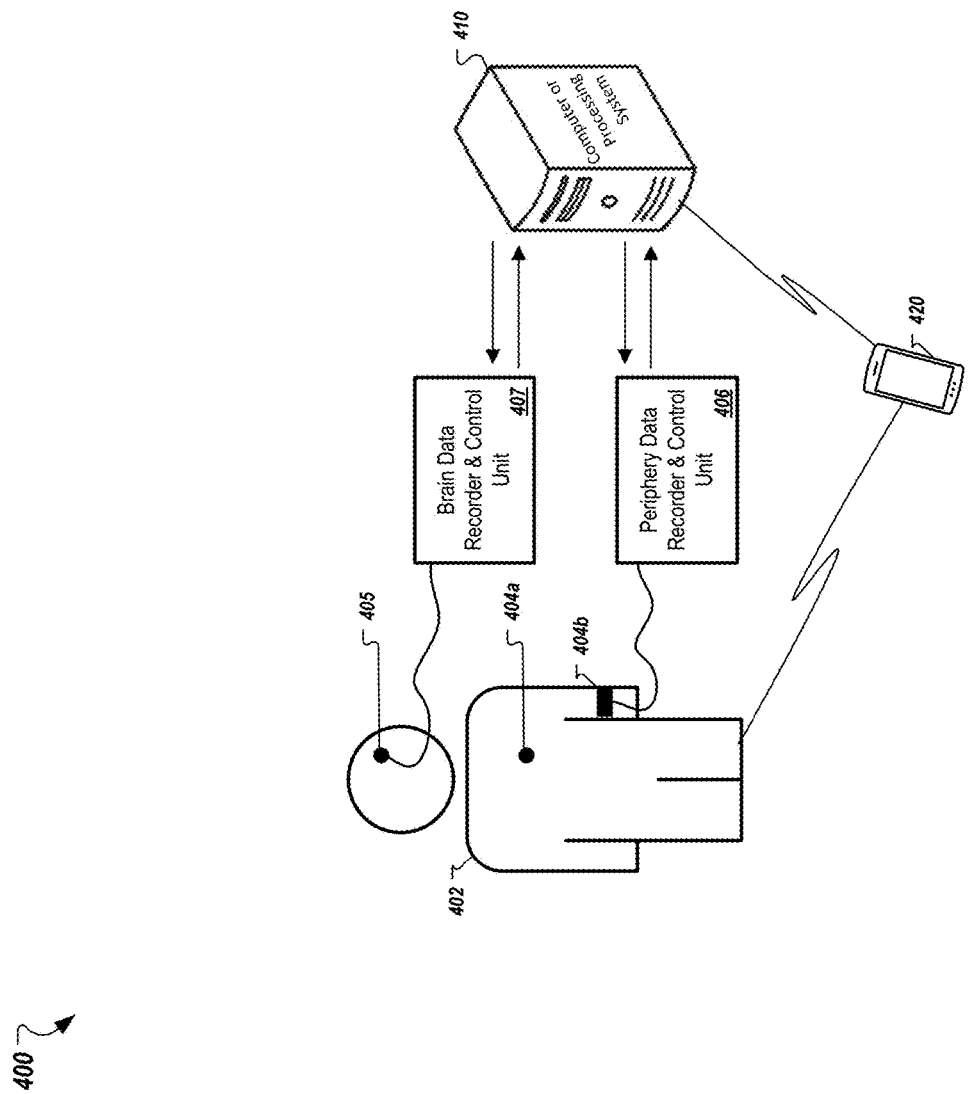
FIG. 4 is a conceptual diagram of an example system for recording and processing physiological data representative of cardiac activity and brain activity, and using the data to determine brain-periphery temporal associations.

FIG. 4 is a conceptual diagram of an example system 400 for recording and processing brain activity data and peripheral activity data of a subject mammal 402, and using the data for determining a brain-periphery temporal association. For the purpose of this example, the subject 402 will be considered as a human, and more specifically as a patient of a healthcare provider. However, it should be understood that the description is not limited to this example. In other implementations, the subject 402 may be a human who is not specifically associated with a healthcare provider, or may be any other mammal, such as, e.g., a mouse, rat, or non-human primate.

One or more periphery sensors 404a and/or 404b are disposed on a surface of the patient 402 to enable recording of periphery signals or physiological data that describes a periphery activity of a mammal, such as, e.g., cardiac activity, muscle activity, nerve activity, or ocular activity. In some implementations, the sensors can be, e.g., one or more ECG or EMG electrode leads affixed to a patient. In some implementations, the periphery sensors can be placed within a mammal or patient as invasively placed sensors and devices such as, e.g., pacemakers, embedded cardiac monitors, and the like. In some implementations, the sensors can be selected from sensors that measure or provide an indication of changes in electrocardiogram (ECG) data, blood pressure data, and photoplethysmography (PPG) data. In some implementations, the sensors can be selected from sensors that measure or provide an indication of changes in nerve activity data, muscle movement data, cardiac activity data, or pupil dilation data. In some implementations, the periphery activity data can be obtained from one or more physiologic sensors that are integrated with or communicatively coupled to a smartphone, a tablet computer, a watch body, a watch band, or a wearable patch. For example, in some implementations, the patient 402 can manually contact a fixed pair of external electrodes or other sensors with his or her fingers, or the patient 402 may wear a watch, wristband, chest band, or other device that secures one or more electrodes or other sensors in position on the patient 402 to sense the patient's cardiac activity. A mobile computing device (e.g., smartphone 420) may be used by the patient 402 or a healthcare provider to configure aspects of the data recording procedure in a clinical or non-clinical setting.

One or more brain sensors 405 are disposed on a surface of or embedded within the patient 402 to enable recording of brain activity signals or physiological data that describes brain activity of a mammal. In some implementations, the sensors can be, e.g., one or more EEG electrode leads affixed to a patient. In some implementations, the brain sensors can be placed within a mammal or patient as invasively placed sensors and devices such as, e.g., embedded EEG electrodes, and the like. In some implementations, the brain activity data can be obtained from one or more physiologic sensors that are integrated with or communicatively coupled to a smartphone, a tablet computer, a watch body, a watch band, or a wearable patch. For example, in some implementations, the patient 402 can manually contact a fixed pair of external electrodes or other sensors with his or her fingers, or the patient 402 may wear a watch, wristband, chest band, or other device that secures one or more electrodes or other sensors in position on the patient 402 to sense the patient's cardiac activity. A mobile computing device (e.g., smartphone 420) may be used by the patient 402 or a healthcare provider to configure aspects of the data recording procedure in a clinical or non-clinical setting.

The system 400 can further include a first data recorder and control unit 406 for controlling and recording the periphery data from the sensors. In some implementations, data recording and/or controlling units can be integrated into one or more sensor devices and/or a mobile computing device (e.g., smartphone 420). The system 400 can further include a second data recorder and control unit 407 for controlling and recording the brain data from the sensors. In some implementations, data recording and/or controlling units can be integrated into one or more sensor devices and/or a mobile computing device (e.g., smartphone 420). In some implementations, the first and second data recorder and control units 406, 407 can be the same data recorder and control unit and/or integrated into the same device, such as one or more sensor devices and/or a mobile computing device (e.g., smartphone 420).

The system 400 further includes a data processing system 410, and one or more input/output devices (e.g., smartphone 420). In some implementations, data processing system 410 can be integrated into one or more sensor devices and/or a mobile computing device (e.g., smartphone 420). For example, a wearable sensing device can, in some implementations, include brain and/or periphery data sensors, one or more data recording and control units, the data processing system, and, optionally, one or more input/output interfaces.

The first and second data recorder and controller units 406, 407 are communicably coupled to the processing system 410. The processing system 410 is a system of one or more computers, which may be distributed in one or more physical locations. System 410 may or may not be in the same physical location as the patient 402 and/or the first and/or second data recorder and controller units 406, 407. The system 410 may be coupled to peripheral devices such as a display screen (e.g., on smartphone 420) for presenting information to a user, patient, or healthcare provider, and an input interface (e.g., on smartphone 420) for receiving user inputs. Moreover, the system 410 may include a variety of components known to one of ordinary skill in the art that facilitate processing of brain and/or peripheral data in the processes described herein.

It should be understood that in some implementations, the brain and/or periphery data can be recorded and processed simultaneously in real-time, or a delay can occur between the recording of the data and the processing. For example, the processing can be done using data recorded minutes, days, or even years prior to the processing. The data can be stored, e.g., on computer-readable media, for a length of time prior to the processing of the data.

In some implementations, a seizure warning system (not shown) is provided. The seizure warning system can be described by system 400, wherein sensor 405 includes one or more electrodes for recording EEG signals from the mammal, and wherein sensor(s) 404a and/or 404b enable recording physiological data that describes a cardiac activity of a mammal. In some implementations, the sensors can be, e.g., one or more ECG electrode leads affixed to a patient. In some implementations, the sensors can be selected from sensors that measure or provide an indication of changes in electrocardiogram (ECG) data, blood pressure data, and photoplethysmography (PPG) data. The system can determine an estimate of risk of a future seizure based on a brain-cardiac temporal association and provide an automatic warning based on the estimated risk. The system can further optionally determine an estimate of timing of a future seizure based on an brain-cardiac temporal association and provide an automatic warning based on the estimated timing, including, optionally an indication of the estimated timing. In some implementations, the seizure warning system can estimate risk and/or timing of clusters seizures rather than individual seizures.

Figure 5:
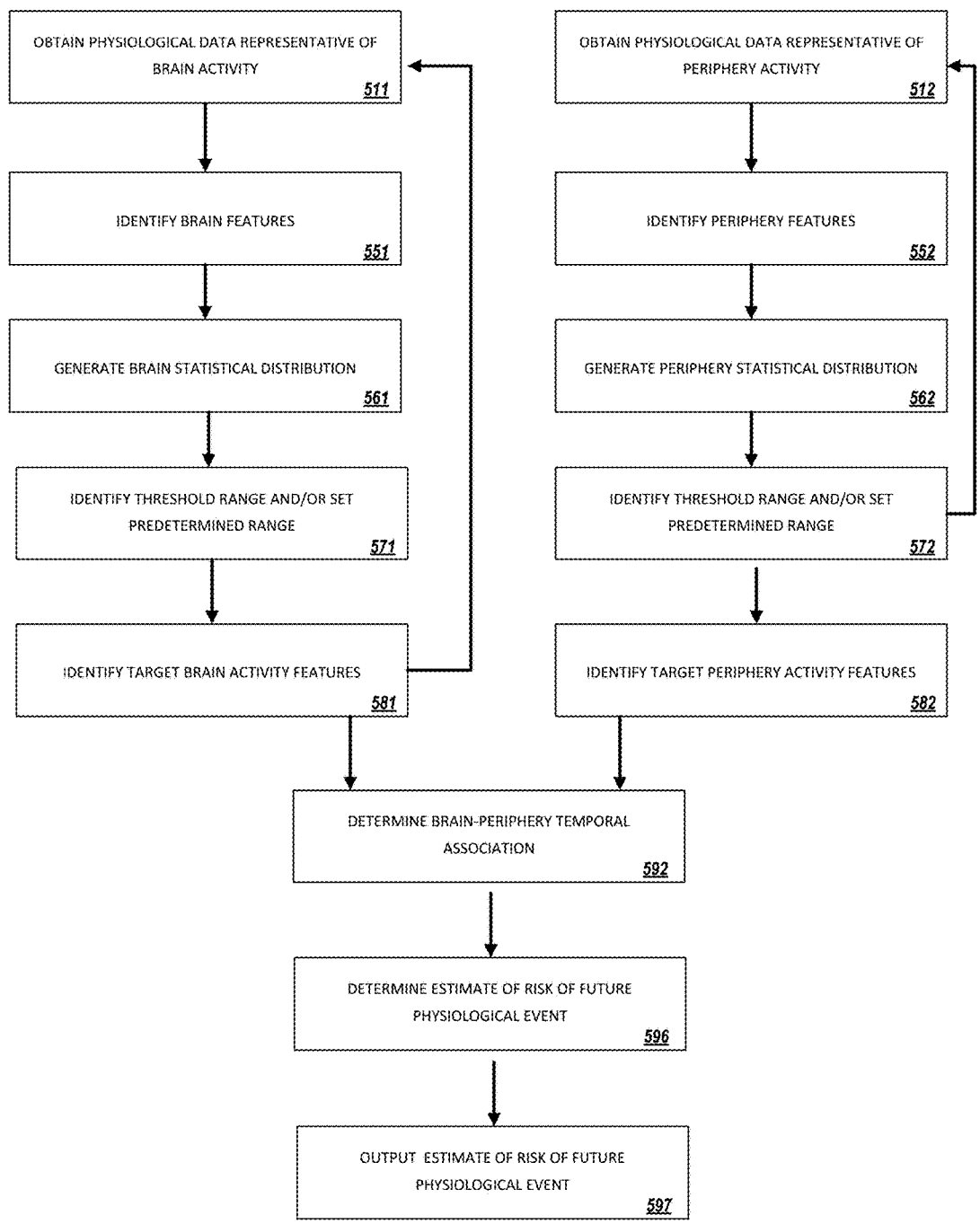
FIG. 5 is a flowchart of an example process for determining an estimate of risk of a future physiological event.

In some implementations of the processes described herein, a method for estimating the risk of a physiological event in a mammal prior to the occurrence of the event is provided. FIG. 5 is a flowchart of an example process 500 for estimating the risk of a physiological event in a mammal prior to the occurrence of the event using non-invasive monitoring of biological markers in a mammal. In some implementations, process 500 can generate and output an estimation of risk of a future physiological event based on a brain-periphery temporal association. The process 500 can be performed by a computing system, e.g., system 410 of FIG. 4. The process proceeds similarly to process 300 described above. At stage 511, the system obtains or receives brain data from a brain activity measurement device that describes brain activity of a mammal over a first period of time. At stage 512, the system obtains or receives periphery data from a peripheral activity measurement device that describes peripheral activity of a mammal over a second period of time.

At stage 551, the system generates one or more brain feature representations, e.g., EEG line length ($EEG_{LL}$) representations, based on the brain data. At stage 552, the system generates one or more periphery feature representations based on the periphery data. In some implementations, generating one or more brain feature representations based on the brain data and/or generating one or more periphery feature representations based on the periphery data can include processing the respective brain or periphery data through a univariate determination or a multivariate determination. In some implementations, processing the periphery data includes determining a discrete estimate of the logarithmic derivative of the one or more intervals as described in process 100.

At stage 561, the system processes the brain activity feature representations and generates an estimated distribution of the brain activity feature representations of the mammal over the period of time. At stage 562, the system processes the periphery activity feature representations and generates an estimated distribution of the periphery activity feature representations of the mammal over the period of time. At stage 571, the system identifies a predetermined range within the distribution with which to compare the brain activity feature representations within the distribution. At stage 572, the system identifies a predetermined range within the distribution with which to compare the periphery activity feature representations within the distribution. In some implementations, stage 571 and/or 572 involves an optional step of identifying, by the system, a threshold range within the brain and/or periphery distribution based on the distribution. In some implementations, the process 500 can optionally be used to build or train (e.g., via machine learning) a model for determination of brain-periphery temporal association, brain-periphery coincidence, and/or brain-periphery coincidence rate. In such implementations of the process, stages 511-571 and 512-572 are used to identify or generate a modified threshold range or modified predetermined range. The modified threshold or predetermined range can then be provided as an output to a user or stored in a memory, e.g., on computer-readable media, for later use in process 500. The user can then return to stages 511 and 512 to repeat process 500 for the same, different, or new data using the modified threshold or predetermined range. In this manner, the predetermined range can be set to useful or statistically significant values specific to a chosen disease, periphery measurement, group of mammals, or individual mammal or patient.

At stage 581, the system identifies one or more brain activity feature representations that fall outside of a predetermined range in the distribution and generates a set of one or more target brain activity representations. At stage 582, the system identifies one or more periphery activity feature representations that fall outside of a predetermined range in the distribution and generates a set of one or more target periphery activity representations. The process 500 further includes stage 592, wherein the system determines, a brain-periphery temporal association between the one or more target brain feature representations and the one or more target periphery feature representations.

The process 500 can optionally further include stage 596, wherein the system predicts and/or determines an estimate of the risk of a future physiological event based on, e.g., the occurrence of temporally associated, or coincident, target brain-periphery feature representations. In some implementations, the process can further include providing, by the system, an estimate of risk of a future physiological event based on the brain-periphery temporal association and/or a quantification of the brain-periphery temporal association. Optionally, the process can further include providing an indication, such as, e.g., a graphical or tabular output of the estimate of risk of the physiological event. In some implementations, the output can be a physical output, an image on a graphical user interface, an audible output, or the like. In some implementations, the processes and systems provide an early warning of a potential future physiological event so that protective measures may be taken to lessen the effect of the future physiological event, such as by ensuring a safe, fall-free environment for a seizure, or taking intervention measures, such as, e.g., anti-epileptic drugs in the case of an impending epileptic seizure, that lessen the event, prevent the event, or delay the event. In some implementations of the process, the system can provide a plot of the magnitude and/or frequency of the brain-periphery temporal association over the period of time. In some implementations of the process, the system can provide an estimate of risk of a future physiological event based on a trend in the magnitude and/or frequency of brain-periphery temporal association. In some implementations of the process, the system can provide an estimate of the timing of the future physiological event, such as how long a subject has before the physiological event will likely occur, giving the subject a valuable indication of how much time is available to prepare for or intervene against the future physiological event, which may affect the preparation decisions and/or choice of intervention methods and/or medications. In some implementations of the process, an indication of an estimate of risk of a future physiological event can also include an indication of the estimate of timing of the potential future physiological event.

In some implementations, the future physiological event can be selected from the onset of acquired epilepsy, an epileptic seizure, sudden unexpected death in epilepsy (SUDEP), hydrocephalous, sepsis, and onset of cerebral palsy. In some implementations of process 500, the periphery data is ECG data; receiving and/or processing the periphery data includes the methods of process 100; and the physiological event is selected from the onset of acquired epilepsy, an epileptic seizure, and sudden unexpected death in epilepsy (SUDEP).

Figure 6:
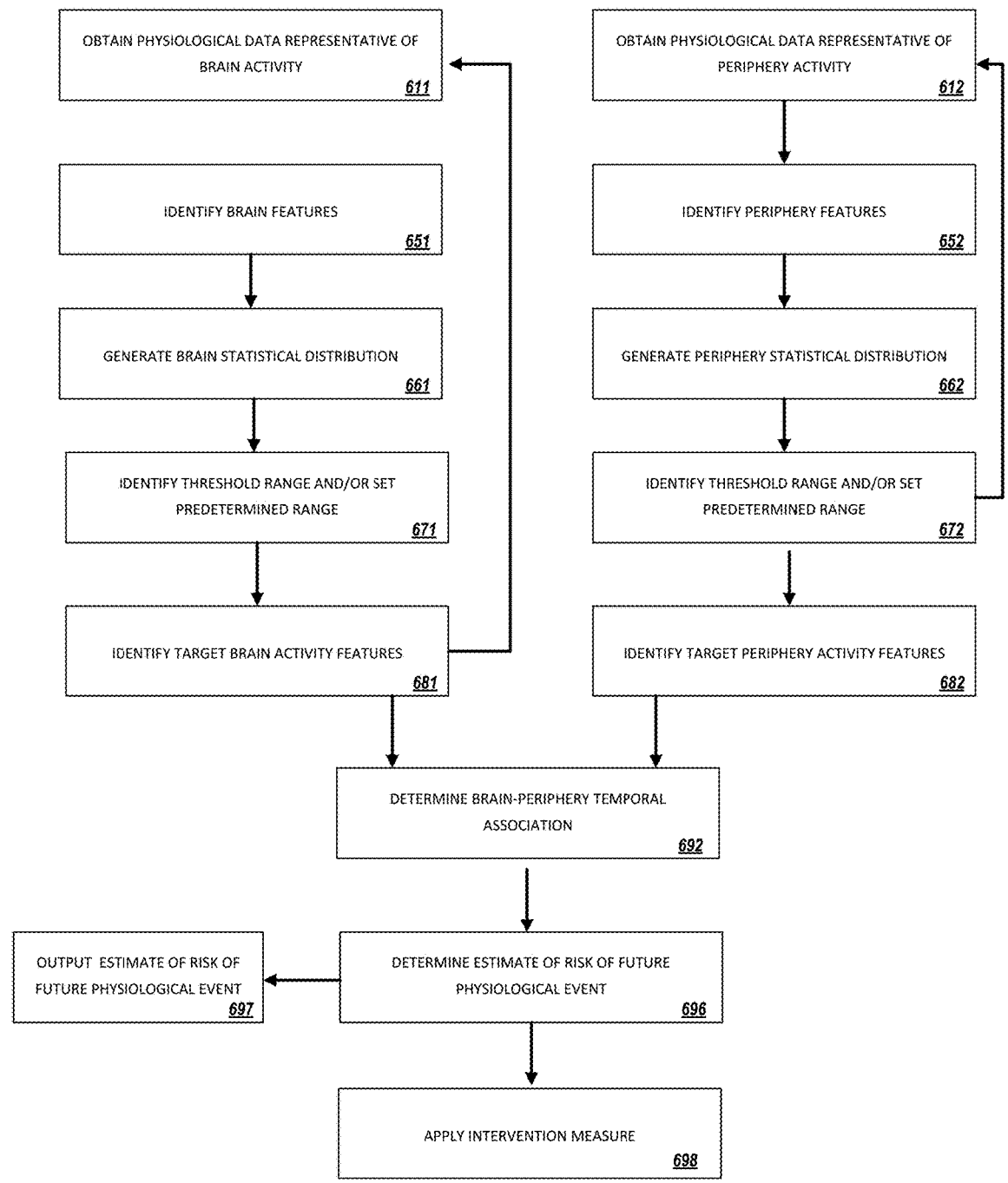
FIG. 6 is a flowchart of an example process for intervening to prevent a future physiological event.

In some implementations of the processes described herein, a method for preventing an occurrence of a physiological event in a mammal is provided. FIG. 6 is a flowchart of an example process 600 for estimating the risk of a physiological event in a mammal prior to the occurrence of the event using non-invasive monitoring of biological markers in a mammal. In some implementations, process 600 can generate and output an estimation of risk of a future physiological event based on a brain-periphery temporal association. The process 600 can be performed by a computing system, e.g., system 410 of FIG. 4. The process proceeds similarly to processes 300 and 500 described above. At stage 611, the system obtains or receives brain data from a brain activity measurement device that describes brain activity of a mammal over a first period of time. At stage 612, the system obtains or receives periphery data from a peripheral activity measurement device that describes peripheral activity of a mammal over a second period of time.

At stage 651, the system generates one or more brain feature representations, e.g., EEG line length ($EEG_{LL}$) representations, based on the brain data. At stage 652, the system generates one or more periphery feature representations based on the periphery data. In some implementations, generating one or more brain feature representations based on the brain data and/or generating one or more periphery feature representations based on the periphery data can include processing the respective brain or periphery data through a univariate determination or a multivariate determination. In some implementations, processing the periphery data includes determining a discrete estimate of the logarithmic derivative of the one or more intervals as described in process 100.

At stage 661, the system processes the brain activity feature representations and generates an estimated distribution of the brain activity feature representations of the mammal over the period of time. At stage 662, the system processes the periphery activity feature representations and generates an estimated distribution of the periphery activity feature representations of the mammal over the period of time. At stage 671, the system identifies a predetermined range within the distribution with which to compare the brain activity feature representations within the distribution. At stage 672, the system identifies a predetermined range within the distribution with which to compare the periphery activity feature representations within the distribution. In some implementations, stage 671 and/or 672 involves an optional step of identifying, by the system, a threshold range within the brain and/or periphery distribution based on the distribution. In some implementations, the process 600 can optionally be used to build or train (e.g., via machine learning) a model for determination of brain-periphery temporal association, brain-periphery coincidence, and/or brain-periphery coincidence rate. In such implementations of the process, stages 611-671 and 612-672 are used to identify or generate a modified threshold range or modified predetermined range. The modified threshold or predetermined range can then be provided as an output to a user or stored in a memory, e.g., on computer-readable media, for later use in process 600. The user can then return to stages 611 and 612 to repeat process 600 for the same, different, or new data using the modified threshold or predetermined range. In this manner, the predetermined range can be set to useful or statistically significant values specific to a chosen disease, periphery measurement, group of mammals, or individual mammal or patient.

At stage 681, the system identifies one or more brain activity feature representations that fall outside of a predetermined range in the distribution and generates a set of one or more target brain activity representations. At stage 682, the system identifies one or more periphery activity feature representations that fall outside of a predetermined range in the distribution and generates a set of one or more target periphery activity representations. The process 600 further includes stage 692, wherein the system determines, a brain-periphery temporal association between the one or more target brain feature representations and the one or more target periphery feature representations.

The process 600 can optionally further include stage 696, wherein the system predicts and/or determines an estimate of the risk of a future physiological event based on, e.g., the occurrence of temporally associated, or coincident, target brain-periphery feature representations. In some implementations, the process can further include providing, by the system, an estimate of risk of a future physiological event based on the brain-periphery temporal association and/or a quantification of the brain-periphery temporal association. Optionally, the process can further include stage 697, providing an indication, such as, e.g., a graphical or tabular output of the estimate of risk of the physiological event. In some implementations, the output can be a physical output, an image on a graphical user interface, an audible output, or the like. In some implementations, the processes and systems provide an early warning of a potential future physiological event so that protective measures may be taken to lessen the effect of the future physiological event, such as by ensuring a safe, fall-free environment for a seizure, or taking intervention measures, such as, e.g., anti-epileptic drugs in the case of an impending epileptic seizure, that lessen the event, prevent the event, or delay the event. In some implementations of the process, the system can provide a plot of the magnitude and/or frequency of the brain-periphery temporal association over the period of time. In some implementations of the process, the system can provide an estimate of risk of a future physiological event based on a trend in the magnitude and/or frequency of brain-periphery temporal association. In some implementations of the process, the system can provide an estimate of the timing of the future physiological event, such as how long a subject has before the physiological event will likely occur, giving the subject a valuable indication of how much time is available to prepare for or intervene against the future physiological event, which may affect the preparation decisions and/or choice of intervention methods and/or medications. In some implementations of the process, an indication of an estimate of risk of a future physiological event can also include an indication of the estimate of timing of the potential future physiological event.

In some implementations, the future physiological event can be selected from the onset of acquired epilepsy, an epileptic seizure, sudden unexpected death in epilepsy (SUDEP), hydrocephalous, sepsis, and onset of cerebral palsy. In some implementations of process 600, the periphery data is ECG data; receiving and/or processing the periphery data includes the methods of process 100; and the physiological event is selected from the onset of acquired epilepsy, an epileptic seizure, and sudden unexpected death in epilepsy (SUDEP).

The process 600 can optionally further include stage 698, wherein at least one intervention measure that is commensurate with the prevention of the specific physiological event can be applied. In some implementations of process 600, estimating the risk and applying the intervention measure can be performed automatically, e.g., by a wearable device such as, e.g., a medication pump. In some implementations of process 600, the physiological event is the onset of acquired epilepsy and the at least on intervention measure is an anti-epileptogenesis therapy. In some implementations, the intervention measure is a therapy that helps with blood brain barrier (BBB) integrity. In some implementations, the intervention measure is a cerebrovascular drug. In some implementations of process 600, the physiological event is an epileptic seizure and the at least on intervention measure is an anti-epileptic drug (AED), such as, e.g., a drug selected from Acetazolamide, Carbamazepine, Clobazam, Clonazepam, Eslicarbazepine acetate, Ethosuximide, Gabapentin, Lacosamide, Lamotrigine, Levetiracetam, Nitrazepam, Oxcarbazepine, Perampanel, Piracetam, Phenobarbital, Phenytoin, Pregabalin, Primidone, Rufinamide, Sodium valproate, Stiripentol, Tiagabine, Topiramate, Vigabatrin, Zonisamide, and the like, and combinations thereof. In some implementations, process 600 can optionally further include evaluating effectiveness of an intervention measure by determining, through standard methods the efficacy of the intervention measure after application of the intervention measure. In some implementations, evaluating effectiveness of an intervention measure can include repeating stages 611-692 and 612-692 to determine if the brain-periphery temporal associations are present, have decreased in frequency or magnitude, or the like.

In some implementations of the processes described herein, a method for detecting a brain-periphery coincidence in a mammal is provided. The method can include obtaining brain activity data that describes brain activity of the mammal over a period of time; obtaining peripheral activity data that describes peripheral activity of the mammal over a period of time; processing the peripheral activity data to generate independent peripheral activity data that is independent of behavioral state; and using a machine-learning model to detect presence of a brain-periphery coincidence in the mammal based on the brain activity data and the peripheral activity data.

Figure 24:
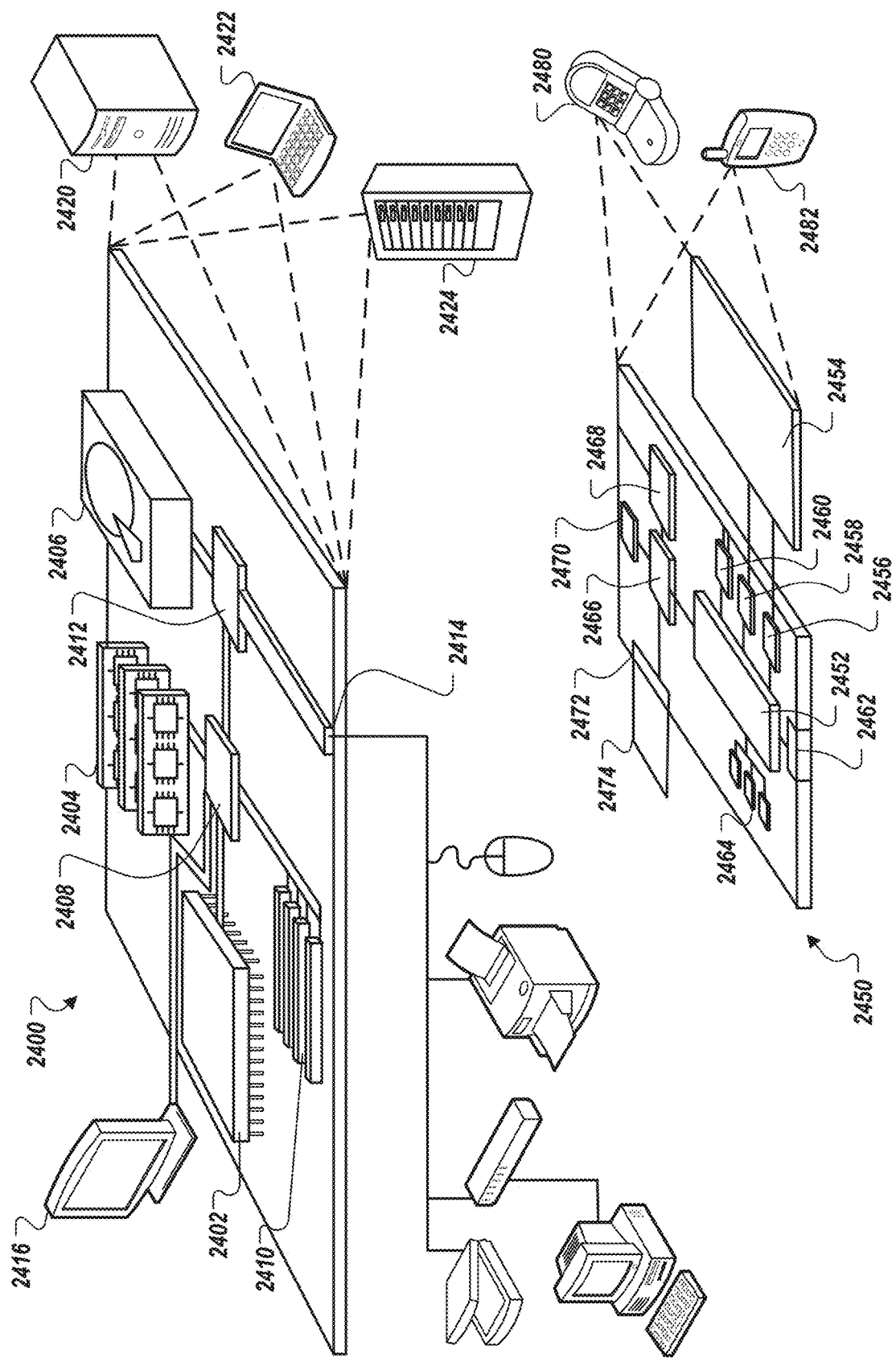
FIG. 24 is a schematic diagram that shows an example of a computing device and a mobile computing device.

FIG. 24 shows an example of a computing device 2400 and an example of a mobile computing device that can be used to implement the techniques described here. The computing device 2400 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 2400 includes a processor 2402, a memory 2404, a storage device 2406, a high-speed interface 2408 connecting to the memory 2404 and multiple high-speed expansion ports 2410, and a low-speed interface 2412 connecting to a low-speed expansion port 2414 and the storage device 2406. Each of the processor 2402, the memory 2404, the storage device 2406, the high-speed interface 2408, the high-speed expansion ports 2410, and the low-speed interface 2412, are interconnected using various busses, and may be mounted on a common motherboard or in other manners as appropriate. The processor 2402 can process instructions for execution within the computing device 2400, including instructions stored in the memory 2404 or on the storage device 2406 to display graphical information for a GUI on an external input/output device, such as a display 2416 coupled to the high-speed interface 2408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 2404 stores information within the computing device 2400. In some implementations, the memory 2404 is a volatile memory unit or units. In some implementations, the memory 2404 is a non-volatile memory unit or units. The memory 2404 may also be another form of computer-readable medium, such as a magnetic or optical disk.

The storage device 2406 is capable of providing mass storage for the computing device 2400. In some implementations, the storage device 2406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The computer program product can also be tangibly embodied in a computer- or machine-readable medium, such as the memory 2404, the storage device 2406, or memory on the processor 2402.

The high-speed interface 2408 manages bandwidth-intensive operations for the computing device 2400, while the low-speed interface 2412 manages lower bandwidth-intensive operations. Such allocation of functions is exemplary only. In some implementations, the high-speed interface 2408 is coupled to the memory 2404, the display 2416 (e.g., through a graphics processor or accelerator), and to the high-speed expansion ports 2410, which may accept various expansion cards (not shown). In the implementation, the low-speed interface 2412 is coupled to the storage device 2406 and the low-speed expansion port 2414. The low-speed expansion port 2414, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 2400 may be implemented in a number of different forms, as shown in the figure. For example, it may be implemented as a standard server 2420, or multiple times in a group of such servers. In addition, it may be implemented in a personal computer such as a laptop computer 2422. It may also be implemented as part of a rack server system 2424. Alternatively, components from the computing device 2400 may be combined with other components in a mobile device (not shown), such as a mobile computing device 2450. Each of such devices may contain one or more of the computing device 2400 and the mobile computing device 2450, and an entire system may be made up of multiple computing devices communicating with each other.

The mobile computing device 2450 includes a processor 2452, a memory 2464, an input/output device such as a display 2454, a communication interface 2466, and a transceiver 2468, among other components. The mobile computing device 2450 may also be provided with a storage device, such as a micro-drive or other device, to provide additional storage. Each of the processor 2452, the memory 2464, the display 2454, the communication interface 2466, and the transceiver 2468, are interconnected using various buses, and several of the components may be mounted on a common motherboard or in other manners as appropriate.

The processor 2452 can execute instructions within the mobile computing device 2450, including instructions stored in the memory 2464. The processor 2452 may be implemented as a chipset of chips that include separate and multiple analog and digital processors. The processor 2452 may provide, for example, for coordination of the other components of the mobile computing device 2450, such as control of user interfaces, applications run by the mobile computing device 2450, and wireless communication by the mobile computing device 2450.

The processor 2452 may communicate with a user through a control interface 2458 and a display interface 2456 coupled to the display 2454. The display 2454 may be, for example, a TFT (Thin-Film-Transistor Liquid Crystal Display) display or an OLED (Organic Light Emitting Diode) display, or other appropriate display technology. The display interface 2456 may comprise appropriate circuitry for driving the display 2454 to present graphical and other information to a user. The control interface 2458 may receive commands from a user and convert them for submission to the processor 2452. In addition, an external interface 2462 may provide communication with the processor 2452, so as to enable near area communication of the mobile computing device 2450 with other devices. The external interface 2462 may provide, for example, for wired communication in some implementations, or for wireless communication in other implementations, and multiple interfaces may also be used.

The memory 2464 stores information within the mobile computing device 2450. The memory 2464 can be implemented as one or more of a computer-readable medium or media, a volatile memory unit or units, or a non-volatile memory unit or units. An expansion memory 2474 may also be provided and connected to the mobile computing device 2450 through an expansion interface 2472, which may include, for example, a SIMM (Single In Line Memory Module) card interface. The expansion memory 2474 may provide extra storage space for the mobile computing device 2450, or may also store applications or other information for the mobile computing device 2450. Specifically, the expansion memory 2474 may include instructions to carry out or supplement the processes described above, and may include secure information also. Thus, for example, the expansion memory 2474 may be provide as a security module for the mobile computing device 2450, and may be programmed with instructions that permit secure use of the mobile computing device 2450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 2464, the expansion memory 2474, or memory on the processor 2452. In some implementations, the computer program product can be received in a propagated signal, for example, over the transceiver 2468 or the external interface 2462.

The mobile computing device 2450 may communicate wirelessly through the communication interface 2466, which may include digital signal processing circuitry where necessary. The communication interface 2466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2468 using a radio-frequency. In addition, short-range communication may occur, such as using a Bluetooth, Wi-Fi, or other such transceiver (not shown). In addition, a GPS (Global Positioning System) receiver module 2470 may provide additional navigation- and location-related wireless data to the mobile computing device 2450, which may be used as appropriate by applications running on the mobile computing device 2450.

The mobile computing device 2450 may also communicate audibly using an audio codec 2460, which may receive spoken information from a user and convert it to usable digital information. The audio codec 2460 may likewise generate audible sound for a user, such as through a speaker, e.g., in a handset of the mobile computing device 2450. Such sound may include sound from voice telephone calls, may include recorded sound (e.g., voice messages, music files, etc.) and may also include sound generated by applications operating on the mobile computing device 2450.

The mobile computing device 2450 may be implemented in a number of different forms, as shown in the figure. For example, it may be implemented as a cellular telephone 2480. It may also be implemented as part of a smart-phone 2482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal, and also including devices in which some or all of the instruction logic is encoded into the hardware design (e.g., ASICs, including digital or mixed analog/digital devices). The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

A number of embodiments of the invention have been described. Nevertheless, it will be understood that various modifications may be made without departing from the spirit and scope of the invention. Accordingly, other embodiments are within the scope of the following claims and exemplary embodiments.

Embodiment 1. A computer-implemented method, comprising:
  receiving, by a system of one or more computers, physiological data that describes cardiac activity of a mammal over a period of time;
  identifying, by the system, two or more reference points in the physiological data;

determining, by the system, one or more intervals wherein each interval is an interval between a unique set of two of the reference points;

processing, by the system, the one or more intervals to generate one or more cardiac activity feature representations, wherein a distribution of the cardiac activity feature representations of the mammal over the period of time is independent of the mammal's behavioral state during the period of time; and providing, by the system, an indication of the cardiac activity feature representations of the mammal over the period of time.

Embodiment 2. The computer-implemented method of embodiment 1, further comprising:

processing, by the system, the cardiac activity feature representations to generate an estimated distribution of the cardiac activity feature representations of the mammal over the period of time; and providing, by the system, an indication of the distribution of the cardiac activity feature representations of the mammal over the period of time.

Embodiment 3. The computer-implemented method of embodiment 2, further comprising:

identifying, by the system, a threshold range within the distribution based on the distribution; and providing, by the system, an indication of the threshold range.

Embodiment 4. The computer-implemented method of embodiment 3, further comprising:

identifying, by the system, one or more cardiac activity feature representations that are outside of a predetermined range in the distribution to generate a set of one or more target cardiac activity feature representations; and providing, by the system, an indication of the one or more target cardiac activity feature representations outside of the predetermined range in the distribution.

Embodiment 5. The computer-implemented method of embodiment 4, further comprising:

quantifying, by the system, the magnitude of the one or more target cardiac activity feature representations; and providing, by the system, an indication of the magnitude of the one or more target cardiac activity feature representations.

Embodiment 6. The computer-implemented method of any one of embodiments 4 or 5, further comprising:

quantifying, by the system, the frequency of the one or more target cardiac activity feature representations; and providing, by the system, an indication of the frequency of the one or more target cardiac activity feature representations.

Embodiment 7. The computer-implemented method of embodiment 5, further comprising:

providing, by the system, a plot of the magnitude of the one or more target cardiac activity feature representations over the period of time.

Embodiment 8. The computer-implemented method of embodiment 6, further comprising:

providing, by the system, a plot of the frequency of the one or more target cardiac activity feature representations over the period of time.

Embodiment 9. The computer-implemented method of any one of embodiments 4-8, wherein the predetermined range is based on the threshold range.

Embodiment 10. The computer-implemented method of any one of embodiments 4-8, wherein the predetermined range is the threshold range.

Embodiment 11. The computer-implemented method of any one of embodiments 4-10, wherein each of the one or more target cardiac activity feature representations describes a single heartbeat of the mammal.

Embodiment 12. The computer-implemented method of any one of embodiments 1-11, wherein the physiological data is representative of an electrophysiologic pattern of the cardiac function of the mammal.

Embodiment 13. The computer-implemented method of any one of embodiments 1-11, wherein the physiological data is selected from electrocardiogram (ECG) data, blood pressure data, and photoplethysmography (PPG) data.

Embodiment 14. The computer-implemented method of any one of embodiments 1-13, wherein the physiological data is ECG data and wherein the reference points correspond to one or more morphological feature representations of an ECG of the mammal.

Embodiment 15. The computer-implemented method of embodiment 14, wherein the morphological feature representations are selected from a T-wave peak, a P-wave peak, a R-wave peak, an onset of a P-wave, an onset of Q, and an end of a T-wave.

Embodiment 16. The computer-implemented method of any one of embodiments 1-15, wherein at least one of the two or more reference points are representative of at least one feature of a QRS complex or at least one feature within a QRS complex of the mammal.

Embodiment 17. The computer-implemented method of embodiment 16, wherein the reference points are R wave peaks.

Embodiment 18. The computer-implemented method of embodiment 17, wherein the one or more intervals include at least one RR interval.

Embodiment 19. The computer-implemented method of any one of embodiments 1-18, wherein the one or more intervals are selected from an interval between two successive reference points and an interval between two successive like reference points.

Embodiment 20. The computer-implemented method of any one of embodiments 1-19, wherein the period of time ranges from about 15 minutes to about 200 days.

Embodiment 21. The computer-implemented method of any one of embodiments 1-20, wherein processing the one or more intervals comprises determining for each interval a discrete estimate of the logarithmic derivative of the one or more intervals at a selected reference time, proportional to the difference in the interval before and after each selected reference time determined over a first time window, normalized by the average interval over a second time window.

Embodiment 22. The computer-implemented method of embodiment 21, wherein the first time window is at least 100 ms.

Embodiment 23. The computer-implemented method of embodiment 21, wherein the first time window is at least 1 second.

Embodiment 24. The computer-implemented method of embodiment 21, wherein the first time window is selected from a window of from about 100 ms to about 500 ms and a window of from about 750 ms to about 5000 ms.

Embodiment 25. The computer-implemented method of embodiment 21, wherein the second time window is greater than first time window.

Embodiment 26. The computer-implemented method of embodiment 21, wherein the second time window is twice the length of the first time window.

Embodiment 27. The computer-implemented method of embodiment 21, wherein the first and second time windows are sliding time windows.

Embodiment 28. The computer-implemented method of embodiment 21, wherein processing the one or more intervals comprises determining dlnRR at any time, T, using first window length $\tau$ and second window length $2\tau$, according to the equation:

$$dlnRR(T)_t \stackrel{def}{=} \frac{2}{\tau} \frac{\overline{RRI}(T+\tau/2) - \overline{RRI}(T-\tau/2)}{\overline{RRI}(T+\tau/2) + \overline{RRI}(T-\tau/2)}, \text{ wherein}$$

$$\overline{RRI}(T) = \frac{\tau}{N_{RR}(T)}, \text{ and}$$

$N_{RR}(T)$ = fractional number of intervals $\in [T - \tau/2, T + \tau/2]$, and
wherein the fractional number of intervals include partial intervals that remain inside the first or second time windows.

Embodiment 29. The computer-implemented method of any one of embodiments 1-28, wherein the mammal is human.

Embodiment 30. The computer-implemented method of any one of embodiments 1-28, wherein the mammal is mouse.

Embodiment 31. The computer-implemented method of any one of embodiments 1-28, wherein the mammal is rat.

Embodiment 32. One or more non-transitory computer-readable media encoded with instructions that, when executed by one or more processors of a system, cause the one or more processors to perform operations comprising:
receiving, by a system of one or more computers, physiological data that describes cardiac activity of a mammal over a period of time;
identifying, by the system, two or more reference points in the physiological data;
determining, by the system, one or more intervals wherein each interval is an interval between a unique set of two of the reference points;
processing, by the system, the one or more intervals to generate one or more cardiac activity feature representations, wherein a distribution of the cardiac activity feature representations of the mammal over the period of time is independent of the mammal's behavioral state during the period of time; and
providing, by the system, an indication of the cardiac activity feature representations of the mammal over the period of time.

Embodiment 33. The computer-readable media of embodiment 32, further comprising:
processing, by the system, the cardiac activity feature representations to generate an estimated distribution of the cardiac activity feature representations of the mammal over the period of time; and
providing, by the system, an indication of the distribution of the cardiac activity feature representations of the mammal over the period of time.

Embodiment 34. The computer-readable media of embodiment 33, further comprising:
identifying, by the system, a threshold range within the distribution based on the distribution; and
providing, by the system, an indication of the threshold range.

Embodiment 35. The computer-readable media of embodiment 34, further comprising:
identifying, by the system, one or more cardiac activity feature representations that are outside of a predetermined range in the distribution to generate a set of one or more target cardiac activity feature representations; and
providing, by the system, an indication of the one or more target cardiac activity feature representations outside of the predetermined range in the distribution.

Embodiment 36. The computer-readable media of embodiment 35, further comprising:
quantifying, by the system, the magnitude of the one or more target cardiac activity feature representations; and
providing, by the system, an indication of the magnitude of the one or more target cardiac activity feature representations.

Embodiment 37. The computer-readable media of any one of embodiments 35 or 36, further comprising:
quantifying, by the system, the frequency of the one or more target cardiac activity feature representations; and
providing, by the system, an indication of the frequency of the one or more target cardiac activity feature representations.

Embodiment 38. The computer-readable media of embodiment 36, further comprising:
providing, by the system, a plot of the magnitude of the one or more target cardiac activity feature representations over the period of time.

Embodiment 39. The computer-readable media of embodiment 37, further comprising:
providing, by the system, a plot of the frequency of the one or more target cardiac activity feature representations over the period of time.

Embodiment 40. The computer-readable media of any one of embodiments 35-39, wherein the predetermined range is based on the threshold range.

Embodiment 41. The computer-readable media of any one of embodiments 35-39, wherein the predetermined range is the threshold range.

Embodiment 42. The computer-readable media of any one of embodiments 35-41, wherein each of the one or more target cardiac activity feature representations describes a single heartbeat of the mammal.

Embodiment 43. The computer-readable media of any one of embodiments 32-42, wherein the physiological data is representative of an electrophysiologic pattern of the cardiac function of the mammal.

Embodiment 44. The computer-readable media of any one of embodiments 32-42, wherein the physiological data is selected from electrocardiogram (ECG) data, blood pressure data, and photoplethysmography (PPG) data.

Embodiment 45. The computer-readable media of any one of embodiments 32-44, wherein the physiological data is ECG data and wherein the reference points correspond to one or more morphological features of an ECG of the mammal.

Embodiment 46. The computer-readable media of embodiment 45, wherein the morphological features are selected from a T-wave peak, a P-wave peak, a R-wave peak, an onset of a P-wave, an onset of Q, and an end of a T-wave.

Embodiment 47. The computer-readable media of any one of embodiments 32-46, wherein at least one of the two or more reference points are representative of at least one feature of a QRS complex or at least one feature within a QRS complex of the mammal.

Embodiment 48. The computer-readable media of embodiment 47, wherein the reference points are R wave peaks.

Embodiment 49. The computer-readable media of embodiment 48, wherein the one or more intervals include at least one RR interval.

Embodiment 50. The computer-readable media of any one of embodiments 32-49, wherein the one or more intervals are selected from an interval between two successive reference points and an interval between two successive like reference points.

Embodiment 51. The computer-readable media of any one of embodiments 32-50, wherein the period of time ranges from about 15 minutes to about 200 days.

Embodiment 52. The computer-readable media of any one of embodiments 32-51, wherein processing the one or more intervals comprises determining for each interval a discrete estimate of the logarithmic derivative of the one or more intervals at a selected reference time, proportional to the difference in the interval before and after each selected reference time determined over a first time window, normalized by the average interval over a second time window.

Embodiment 53. The computer-readable media of embodiment 52, wherein the first time window is at least 100 ms.

Embodiment 54. The computer-readable media of embodiment 52, wherein the first time window is at least 1 second.

Embodiment 55. The computer-readable media of embodiment 52, wherein the first time window is selected from a window of from about 100 ms to about 500 ms and a window of from about 750 ms to about 5000 ms.

Embodiment 56. The computer-readable media of embodiment 52, wherein the second time window is greater than first time window.

Embodiment 57. The computer-readable media of embodiment 52, wherein the second time window is twice the length of the first time window.

Embodiment 58. The computer-readable media of embodiment 52, wherein the first and second time windows are sliding time windows.

Embodiment 59. The computer-readable media of embodiment 52, wherein processing the one or more intervals comprises determining dlnRR at any time, T, using first window length $\tau$ and second window length $2\tau$, according to the equation:

$$dlnRR(T)_t \stackrel{def}{=} \frac{2}{\tau} \frac{\overline{RRI}(T+\tau/2) - \overline{RRI}(T-\tau/2)}{\overline{RRI}(T+\tau/2) + \overline{RRI}(T-\tau/2)}, \text{wherein}$$

$$\overline{RRI}(T) = \frac{\tau}{N_{RR}(T)}, \text{and}$$

$N_{RR}(T) = $ fractional number of intervals $\in [T - \tau/2, T + \tau/2]$, and wherein the fractional number of intervals include partial intervals that remain inside the first or second time windows.

Embodiment 60. The computer-readable media of any one of embodiments 32-59, wherein the mammal is human.

Embodiment 61. The computer-readable media of any one of embodiments 32-59, wherein the mammal is mouse.

Embodiment 62. The computer-readable media of any one of embodiments 32-59, wherein the mammal is rat.

Embodiment 63. A computing system, comprising:
one or more processors; and
one or more computer-readable media encoded with instructions that, when executed by the one or more processors, cause the one or more processors to perform the method of any one of embodiments 1-31.

Embodiment 64. A system comprising:
one or more electrodes for recording electrocardiographic (ECG) signals from a mammal; and
a computing system according to embodiment 63.

Embodiment 65. A method of identifying statistically significant cardiac events in a mammal over a period of time, wherein the cardiac events are independent of the mammal's behavioral state during the period of time, comprising:
obtaining physiological data that describes cardiac activity of the mammal over a period of time;
receiving, by a system of one or more computers, the physiological data that describes cardiac activity of a mammal over a period of time;
identifying, by the system, two or more reference points in the representation of cardiac activity;
determining, by the system, one or more intervals wherein each interval is an interval between a unique set of two of the reference points;
processing, by the system, the one or more intervals to generate one or more cardiac activity feature representations, wherein a distribution of the cardiac activity feature representations of the mammal over the period of time is independent of the mammal's behavioral state during the period of time;
processing, by the system, the cardiac activity feature representations to generate an estimated distribution of the cardiac activity feature representations of the mammal over the period of time;
identifying, by the system, one or more cardiac activity feature representations that are outside of a predetermined range in the distribution to generate a set of one or more target cardiac activity feature representations; and
providing, by the system, an indication of the one or more target cardiac activity feature representations outside of the predetermined range in the distribution.

Embodiment 66. The method of embodiment 65, further comprises quantifying, by the system, the magnitude of the one or more target intervals.

Embodiment 67. The method of any one of embodiments 65 and 66, wherein processing the one or more intervals comprises determining for each of one or more selected reference times a discrete estimate of the logarithmic derivative of the one or more intervals at the selected reference time, proportional to the difference in the interval before and after each selected reference time determined over a first time window, normalized by the average interval over a second time window.

Embodiment 68. The method of any one of embodiments 65-67, wherein the physiological data is selected from electrocardiogram (ECG) data, blood pressure data, and photoplethysmography (PPG) data.

Embodiment 69. The method of any one of embodiments 65-68, wherein the physiological data was obtained one or more physiologic sensors that are integrated with or communicatively coupled to a smartphone, a tablet computer, a watch body, a watch band, or a wearable patch.

Embodiment 70. A computer-implemented method, comprising:
  receiving, by a system of one or more computers, brain data from a brain activity measurement device that describes brain activity of a mammal over a first period of time;
  receiving, by the system, periphery data from a peripheral activity measurement device that describes peripheral activity of a mammal over a second period of time;
  generating, by the system, one or more brain feature representations based on the brain data;
  generating, by the system, one or more periphery feature representations based on the periphery data;
  generating, by the system, one or more brain statistical distributions of the one or more brain features;
  generating, by the system, one or more periphery statistical distributions of the one or more periphery feature representations;
  identifying, by the system, one or more brain feature representations that fall outside of a predetermined range in the brain statistical distribution to generate a set of one or more target brain feature representations;
  identifying, by the system, one or more periphery feature representations that fall outside of a predetermined range in the periphery statistical distribution to generate a set of one or more target periphery feature representations;
  determining, by the system, a brain-periphery temporal association between the one or more target brain feature representations and the one or more target periphery feature representations; and
  providing, by the system, an indication of the temporal association.

Embodiment 71. The computer-implemented method of embodiment 70, further comprising:
  determining, by the system, a quantification of the brain-periphery temporal association; and
  providing, by the system, an indication of the quantification of the brain-periphery temporal association.

Embodiment 72. The computer-implemented method of any one of embodiments 70 or 71, further comprising:
  determining a brain-periphery coincidence rate of one or more target brain feature representations and one or more target periphery feature representations; and
  providing, by the system, and indication of the brain-periphery coincidence.

Embodiment 73. The computer-implemented method of any one of embodiments 70-72, wherein determining the temporal association comprises comparing all brain feature-periphery feature pairs of one or more target brain feature representations and one or more target periphery feature representations.

Embodiment 74. The computer-implemented method of embodiment 73, wherein comparing all brain feature-periphery feature pairs comprises comparing brain feature-periphery feature pairs within a predetermined time window.

Embodiment 75. The computer-implemented method of embodiment 74, wherein the predetermined time window is from about 10 ms to about 2 seconds.

Embodiment 76. The computer-implemented method of any one of embodiments 70-72, wherein determining the temporal association comprises:
  selecting one or more target brain feature representations;
  identifying a predetermined target time window around each of the selected brain feature representations; and
  determining the incidence of one or more target periphery feature representations within each predetermined time window.

Embodiment 77. The computer-implemented method of embodiment 76, wherein the predetermined time window is from about 10 ms to about 2 seconds.

Embodiment 78. The computer-implemented method of any one of embodiments 70-77, further comprising:
  receiving, by the system, data from a physiological measurement device confirming the occurrence of a physiological event.

Embodiment 79. The computer-implemented method of embodiment 78, further comprising:
  determining, by the system, an association between the physiological event and the brain-periphery temporal association.

Embodiment 80. The computer-implemented method of embodiment 79, further comprising:
  providing, by the system, a quantification of the association between the physiological event and the brain-periphery temporal association.

Embodiment 81. The computer-implemented method of embodiment 80, further comprising:
  determining, by the system, a modified predetermined range for the brain statistical distribution based on at least one of the quantification of the brain-periphery temporal association and the quantification of the association between the physiological event and the brain-periphery temporal association.

Embodiment 82. The computer-implemented method of embodiment 81, further comprising:
  determining, by the system, a modified predetermined range for the periphery statistical distribution based on at least one of the quantification of the brain-periphery temporal association and the quantification of the association between the physiological event and the brain-periphery temporal association.

Embodiment 83. The computer-implemented method of embodiment 82, further comprising:
  receiving, by a system of one or more computers, brain data from a brain activity measurement device that describes brain activity of a mammal over a first period of time;
  receiving, by the system, periphery data from a peripheral activity measurement device that describes peripheral activity of a mammal over a second period of time;

identifying, by the system, one or more brain feature representations within the brain data;

identifying, by the system, one or more periphery feature representations within the periphery data;

generating, by the system, one or more brain statistical distributions of the one or more brain feature representations;

generating, by the system, one or more periphery statistical distributions of the one or more periphery feature representations;

identifying, by the system, one or more brain feature representations that fall outside of the modified predetermined range in the brain statistical distribution to generate a set of one or more target brain feature representations;

identifying, by the system, one or more periphery feature representations that fall outside of the modified predetermined range in the periphery statistical distribution to generate a set of one or more target periphery feature representations;

determining, by the system, a brain-periphery temporal association between the one or more target brain feature representations and the one or more target periphery feature representations; and providing, by the system, an indication of the temporal association.

Embodiment 84. The computer-implemented method of any one of embodiments 70-83, wherein the one or more periphery statistical distribution is independent of behavioral state.

Embodiment 85. The computer-implemented method of any one of embodiments 70-84, further comprising:
providing, by the system, an estimate of risk of a future physiological event based on the brain-periphery temporal association.

Embodiment 86. The computer-implemented method of any one of embodiments 70-84, further comprising:
providing, by the system, an estimate of risk of a future physiological event based on the quantification of the brain-periphery temporal association.

Embodiment 87. The computer-implemented method of any one of embodiments 70-86, further comprising:
providing, by the system, a plot of the magnitude of the brain-periphery temporal association over the period of time.

Embodiment 88. The computer-implemented method of any one of embodiments 70-86, further comprising:
providing, by the system, a plot of the frequency of the brain-periphery temporal association over the period of time.

Embodiment 89. The computer-implemented method of embodiment 87, further comprising:
providing, by the system, an estimate of risk of a future physiological event based on a trend in the magnitude of brain-periphery temporal association.

Embodiment 90. The computer-implemented method of embodiment 88, further comprising:
providing, by the system, an estimate of risk of a future physiological event based on a trend in the frequency of the brain-periphery temporal association.

Embodiment 91. The computer-implemented method of any one of embodiments 89 and 90, further comprising:
providing, by the system, an estimate of the magnitude of a future physiological event based on the trend in the brain-periphery temporal association.

Embodiment 92. The computer-implemented method of any one of embodiments 70-91, wherein the brain activity data is selected from electroencephalography (EEG) data and electrocorticography (ECoG) data.

Embodiment 93. The computer-implemented method of embodiment 92, wherein the brain activity data is EEG data and the EEG data is EEG line length data.

Embodiment 94. The computer-implemented method of any one of embodiments 70-93, wherein the periphery activity data is selected from cardiac data, muscle movement data, nerve activity data, pupil dilation data, and body movement data.

Embodiment 95. The computer-implemented method of embodiment 94, wherein the periphery data is cardiac data and the cardiac data is selected from electrocardiogram (ECG) data, blood pressure data, and photoplethysmography (PPG) data.

Embodiment 96. The computer-implemented method of embodiment 95, wherein the periphery data is ECG data and wherein receiving the periphery data comprises the method of any one of embodiments 1-31.

Embodiment 97. The computer-implemented method of embodiment 94, wherein the periphery data is muscle movement data and the muscle movement data is selected from electromyography (EMG) data, and limb or hand acceleration data.

Embodiment 98. The computer-implemented method of embodiment 94, wherein the periphery data is EMG data and the EMG data is stomach EMG data.

Embodiment 99. The computer-implemented method of embodiment 94, wherein the periphery data is nerve activity data and the nerve activity data is selected from nerve conduction data, and vagal nerve activity data.

Embodiment 100. The computer-implemented method of embodiment 94,
wherein the periphery data is body movement data and the body movement data is selected from hand acceleration data, limb acceleration data, and perspiration data.

Embodiment 101. The computer-implemented method of any one of embodiments 70-100, wherein the physiological event is selected from the onset of acquired epilepsy, an epileptic seizure, sudden unexpected death in epilepsy (SUDEP), hydrocephalous, sepsis, and onset of cerebral palsy.

Embodiment 102. The computer-implemented method of any one of embodiments 70-101, wherein the mammal is human.

Embodiment 103. The computer-implemented method of any one of embodiments 70-101, wherein the mammal is mouse.

Embodiment 104. The computer-implemented method of any one of embodiments 70-101, wherein the mammal is rat.

Embodiment 105. One or more non-transitory computer-readable media encoded with instructions that, when executed by one or more processors of a system, cause the one or more processors to perform operations comprising:
receiving, by a system of one or more computers, brain data from a brain activity measurement device that describes brain activity of a mammal over a first period of time;
receiving, by the system, periphery data from a peripheral activity measurement device that describes peripheral activity of a mammal over a second period of time;
generating, by the system, one or more brain feature representations based on the brain data;

generating, by the system, one or more periphery feature representations based on the periphery data;

generating, by the system, one or more brain statistical distributions of the one or more brain features;

generating, by the system, one or more periphery statistical distributions of the one or more periphery features;

identifying, by the system, one or more brain feature representations that fall outside of a predetermined range in the brain statistical distribution to generate a set of one or more target brain feature representations;

identifying, by the system, one or more periphery feature representations that fall outside of a predetermined range in the periphery statistical distribution to generate a set of one or more target periphery feature representations;

determining, by the system, a brain-periphery temporal association between the one or more target brain feature representations and the one or more target periphery feature representations; and providing, by the system, an indication of the temporal association.

Embodiment 106. The computer-readable media of embodiment 105, further comprising:

determining, by the system, a quantification of the brain-periphery temporal association; and providing, by the system, an indication of the quantification of the brain periphery temporal association.

Embodiment 107. The computer-readable media of any one of embodiments 105 or 106, further comprising:

determining a brain-periphery coincidence of one or more target brain feature representations and one or more target periphery feature representations; and providing, by the system, and indication of the brain-periphery coincidence.

Embodiment 108. The computer-readable media of any one of embodiments 105-107, wherein determining the temporal association comprises comparing all brain feature-periphery feature pairs of one or more target brain feature representations and one or more target periphery feature representations.

Embodiment 109. The computer-readable media of embodiment 108, wherein comparing all brain feature-periphery feature pairs comprises comparing brain feature-periphery feature pairs within a predetermined time window.

Embodiment 110. The computer-readable media of embodiment 109, wherein the predetermined time window is from about 10 ms to about 2 seconds.

Embodiment 111. The computer-readable media of any one of embodiments 105-107, wherein determining the temporal association comprises:

selecting one or more target brain feature representations;

identifying a predetermined target time window around each of the selected brain feature representations; and determining the incidence of one or more target periphery feature representations within each predetermined time window.

Embodiment 112. The computer-readable media of embodiment 111, wherein the predetermined time window is from about 10 ms to about 2 seconds.

Embodiment 113. The computer-readable media of any one of embodiments 105-112, further comprising:

receiving, by the system, data from a physiological measurement device confirming the occurrence of a physiological event.

Embodiment 114. The computer-readable media of embodiment 113, further comprising:

determining, by the system, an association between the physiological event and the brain-periphery temporal association.

Embodiment 115. The computer-readable media of embodiment 114, further comprising:

providing, by the system, a quantification of the association between the physiological event and the brain-periphery temporal association.

Embodiment 116. The computer-readable media of embodiment 115, further comprising:

determining, by the system, a modified predetermined range for the brain statistical distribution based on at least one of the quantification of the brain-periphery temporal association and the quantification of the association between the physiological event and the brain-periphery temporal association.

Embodiment 117. The computer-readable media of embodiment 116, further comprising:

determining, by the system, a modified predetermined range for the periphery statistical distribution based on at least one of the quantification of the brain-periphery temporal association and the quantification of the association between the physiological event and the brain-periphery temporal association.

Embodiment 118. The computer-readable media of embodiment 117, further comprising:

receiving, by a system of one or more computers, brain data from a brain activity measurement device that describes brain activity of a mammal over a first period of time;

receiving, by the system, periphery data from a peripheral activity measurement device that describes peripheral activity of a mammal over a second period of time;

identifying, by the system, one or more brain feature representations within the brain data;

identifying, by the system, one or more periphery feature representations within the periphery data;

generating, by the system, one or more brain statistical distributions of the one or more brain feature representations;

generating, by the system, one or more periphery statistical distributions of the one or more periphery feature representations;

identifying, by the system, one or more brain feature representations that fall outside of the modified predetermined range in the brain statistical distribution to generate a set of one or more target brain feature representations;

identifying, by the system, one or more periphery feature representations that fall outside of the modified predetermined range in the periphery statistical distribution to generate a set of one or more target periphery feature representations;

determining, by the system, a brain-periphery temporal association between the one or more target brain feature representations and the one or more target periphery feature representations; and providing, by the system, an indication of the temporal association.

Embodiment 119. The computer-readable media of any one of embodiments 105-118, wherein the one or more periphery statistical distribution is independent of behavioral state.

Embodiment 120. The computer-readable media of any one of embodiments 105-119, further comprising:
providing, by the system, an estimate of risk of a future physiological event based on the brain-periphery temporal association.

Embodiment 121. The computer-readable media of any one of embodiments 105-119, further comprising:
providing, by the system, an estimate of risk of a future physiological event based on the quantification of the brain-periphery temporal association.

Embodiment 122. The computer-readable media of any one of embodiments 105-121, further comprising:
providing, by the system, a plot of the magnitude of the brain-periphery temporal association over the period of time.

Embodiment 123. The computer-readable media of any one of embodiments 105-121, further comprising:
providing, by the system, a plot of the frequency of the brain-periphery temporal association over the period of time.

Embodiment 124. The computer-readable media of embodiment 122, further comprising:
providing, by the system, an estimate of risk of a future physiological event based on a trend in the magnitude of brain-periphery temporal association.

Embodiment 125. The computer-readable media of embodiment 123, further comprising:
providing, by the system, an estimate of risk of a future physiological event based on a trend in the frequency of the brain-periphery temporal association.

Embodiment 126. The computer-readable media of any one of embodiments 124 and 125, further comprising:
providing, by the system, an estimate of the magnitude of a future physiological event based on the trend in the brain-periphery temporal association.

Embodiment 127. The computer-readable media of any one of embodiments 105-127, wherein the brain activity data is selected from electroencephalography (EEG) data and electrocorticography (ECoG) data.

Embodiment 128. The computer-readable media of embodiment 127, wherein the brain activity data is EEG data and the EEG data is EEG line length ($EEG_{LL}$) data.

Embodiment 129. The computer-readable media of any one of embodiments 105-128, wherein the periphery activity data is selected from cardiac data, muscle movement data, nerve activity data, pupil dilation data, and body movement data.

Embodiment 130. The computer-readable media of embodiment 129, wherein the periphery data is cardiac data and the cardiac data is selected from electrocardiogram (ECG) data, blood pressure data, and photoplethysmography (PPG) data.

Embodiment 131. The computer-readable media of embodiment 130, wherein the periphery data is ECG data and wherein receiving the periphery data comprises the method of any one of embodiments 1-31.

Embodiment 132. The computer-readable media of embodiment 129, wherein the periphery data is muscle movement data and the muscle movement data is selected from electromyography (EMG) data and limb or hand acceleration data.

Embodiment 133. The computer-readable media of embodiment 129, wherein the periphery data is EMG data and the EMG data is stomach EMG data.

Embodiment 134. The computer-readable media of embodiment 129, wherein the periphery data is nerve activity data and the nerve activity data is selected from nerve conduction data, and vagal nerve activity data.

Embodiment 135. The computer-readable media of embodiment 129, wherein the periphery data is body movement data and the body movement data is selected from hand acceleration data and limb acceleration data.

Embodiment 136. The computer-readable media of any one of embodiments 105-135, wherein the physiological event is selected from the onset of acquired epilepsy, an epileptic seizure, sudden unexpected death in epilepsy (SUDEP), hydrocephalous, sepsis, and onset of cerebral palsy.

Embodiment 137. The computer-readable media of any one of embodiments 105-136, wherein the mammal is human.

Embodiment 138. The computer-readable media of any one of embodiments 105-136, wherein the mammal is mouse.

Embodiment 139. The computer-readable media of any one of embodiments 105-136, wherein the mammal is rat.

Embodiment 140. A computing system, comprising:
one or more processors; and
one or more computer-readable media encoded with instructions that, when executed by the one or more processors, cause the one or more processors to perform the method of any one of embodiments 70-104.

Embodiment 141. A system comprising:
a device for recording brain activity data from a mammal;
a device for recording peripheral activity from a mammal; and
a computing system according to embodiment 140.

Embodiment 142. A method for estimating the risk of occurrence of a physiological event in a mammal prior to the occurrence of the physiological event, comprising:
obtaining brain activity data that describes brain activity of the mammal over a first period of time;
obtaining peripheral activity data that describes peripheral activity of the mammal over a second period of time;
receiving, by a system of one or more computers, brain data from a brain activity measurement device that describes brain activity of a mammal over the first period of time;
receiving, by the system, periphery data from a peripheral activity measurement device that describes peripheral activity of a mammal over the second period of time;
generating, by the system, one or more brain feature representations based on the brain data;
generating, by the system, one or more periphery feature representations based on the periphery data;
generating, by the system, one or more brain statistical distributions of the one or more brain feature representations;
generating, by the system, one or more periphery statistical distributions of the one or more periphery feature representations;

identifying, by the system, one or more brain feature representations that fall outside of a predetermined range in the brain statistical distribution to generate a set of one or more target brain feature representations;

identifying, by the system, one or more periphery feature representations that fall outside of a predetermined range in the periphery statistical distribution to generate a set of one or more target periphery feature representations;

determining, by the system, a brain-periphery temporal association between the one or more target brain feature representations and the one or more target periphery feature representations;

determining, by the system, an estimate of risk of a future physiological event based on the brain-periphery temporal association; and providing, by the system, an indication of the estimate of risk of the future physiological event.

Embodiment 143. The method of embodiment 142, further comprising determining, by the system, a quantification of the brain-periphery temporal association; wherein providing the estimate of risk of a future physiological event is based on the quantification of the brain-periphery temporal association.

Embodiment 144. The method of embodiment 142, further comprising:
determining, by the system, an estimate of the timing of a future physiological event based on the brain-periphery temporal association; and
providing an indication of the estimate of the timing of the future physiological event.

Embodiment 145. The method of embodiment 143, further comprising:
determining, by the system, an estimate of the timing of a future physiological event based on the quantification of the brain-periphery temporal association; and
providing an indication of the estimate of the timing of the future physiological event.

Embodiment 146. The method of any one of embodiments 142-145, wherein the periphery statistical distribution is independent of behavioral state.

Embodiment 147. The method of any one of embodiments 142-146, wherein the brain activity data is electroencephalography (EEG) data.

Embodiment 148. The method of embodiment 147, wherein the brain activity data is EEG data and the EEG data is EEG line length data.

Embodiment 149. The method of any one of embodiments 142-148, wherein the periphery activity data is selected from cardiac data, muscle movement data, nerve activity data, pupil dilation data, and body movement data.

Embodiment 150. The method of embodiment 149, wherein the periphery data is cardiac data and the cardiac data is selected from electrocardiogram (ECG) data, blood pressure data, and photoplethysmography (PPG) data.

Embodiment 151. The method of embodiment 150, wherein the periphery data is ECG data and wherein receiving the periphery data comprises the method of any one of embodiments 1-31.

Embodiment 152. The method of embodiment 149, wherein the periphery data is muscle movement data and the muscle movement data is selected from electromyography (EMG) data and limb or hand acceleration data.

Embodiment 153. The method of embodiment 149, wherein the periphery data is EMG data and the EMG data is stomach EMG data.

Embodiment 154. The method of embodiment 149, wherein the periphery data is nerve activity data and the nerve activity data is selected from nerve conduction data, and vagal nerve activity data.

Embodiment 155. The method of embodiment 149, wherein the periphery data is body movement data and the body movement data is selected from hand acceleration data, limb acceleration data, and perspiration data.

Embodiment 156. The method of any one of embodiments 142-155, wherein the physiological event is selected from the onset of acquired epilepsy, an epileptic seizure, sudden unexpected death in epilepsy (SUDEP), hydrocephalous, sepsis, and onset of cerebral palsy.

Embodiment 157. The method of embodiment 148, wherein:
the periphery data is ECG data;
receiving the periphery data comprises the method of any one of embodiments 1-31; and
the physiological event is selected from the onset of acquired epilepsy, an epileptic seizure, and sudden unexpected death in epilepsy (SUDEP).

Embodiment 158. The method of any one of embodiments 142-157, wherein the mammal is human.

Embodiment 159. The method of any one of embodiments 142-157, wherein the mammal is mouse.

Embodiment 160. The method of any one of embodiments 142-157, wherein the mammal is rat.

Embodiment 161. The method of any one of embodiments 142-160, wherein the peripheral activity data was obtained from a peripheral activity measurement device that is integrated with or communicatively coupled to a smartphone, a tablet computer, a watch body, a watch band, or a wearable patch.

Embodiment 162. The method of any one of embodiments 142-161, further comprising displaying, on a display device, an output indicative of the estimate of risk of the physiological event.

Embodiment 163. The method of any one of embodiments 144-145, further comprising displaying, on a display device, an output indicative of the estimate of risk of the physiological event.

Embodiment 164. A seizure advisory system comprising:
one or more electrodes for recording electroencephalographic (EEG) signals from a mammal;
one or more devices for recording cardiac data from a mammal; and
a computing system comprising:
one or more processors; and
one or more computer-readable media encoded with instructions that, when executed by the one or more processors, cause the one or more processors to perform operations comprising:
receiving, by the system, EEG data from the mammal over a first period of time;
receiving, by the system, cardiac data from the mammal over a second period of time;
generating, by the system, one or more EEG feature representations based on the EEG data;
generating, by the system, one or more cardiac feature representations based on the cardiac data;

generating, by the system, one or more EEG statistical distributions of the one or more EEG feature representations;

generating, by the system, one or more cardiac statistical distributions of the one or more cardiac feature representations according to the method of any one of embodiments 1-31;

identifying, by the system, one or more EEG feature representations that fall outside of a predetermined range in the EEG statistical distribution to generate a set of one or more target EEG feature representations;

identifying, by the system, one or more cardiac feature representations that fall outside of a predetermined range in the cardiac statistical distribution to generate a set of one or more target cardiac feature representations;

determining, by the system, a brain-cardiac temporal association between the one or more EEG feature representations and the one or more cardiac feature representations;

determining, by the system, an estimate of risk of a future seizure based on the brain-cardiac temporal association; and providing, by the system, an automatic warning based on the estimated risk of a future seizure.

Embodiment 165. The system of embodiment 164, wherein the one or more computer-readable media cause the one or more processors to perform operations further comprising:

determining, by the system, a quantification of the brain-periphery temporal association, wherein providing the estimate of risk of a future physiological event is based on the quantification of the brain-periphery temporal association.

Embodiment 166. The system of embodiment 164, wherein the one or more computer-readable media cause the one or more processors to perform operations further comprising:

determining, by the system, an estimate of the timing of a future physiological event based on the brain-periphery temporal association; and providing an automatic warning indicating the estimate of the timing of the future physiological event.

Embodiment 167. The system of embodiment 165, wherein the one or more computer-readable media cause the one or more processors to perform operations further comprising:

determining, by the system, an estimate of the timing of a future physiological event based on the quantification of the brain-periphery temporal association; and providing an automatic warning indicating the estimate of the timing of the future physiological event.

Embodiment 168. The system of any one of embodiments 164-167, wherein the one or more cardiac statistical distributions are independent of behavioral state.

Embodiment 169. The system of any one of embodiments 164-168, wherein the one or more devices for recording cardiac data comprise one or more electrodes for recording electrocardiographic (ECG) signals from a mammal; one or more blood pressure sensors, one or more optical sensors for recording photoplethysmography (PPG) data from a mammal.

Embodiment 170. The system of any one of embodiments 164-169, wherein the EEG data is EEG line length data.

Embodiment 171. The system of any one of embodiments 164-170, wherein at least one of the EEG data and the cardiac data is obtained from one or more physiologic sensors that are integrated with or communicatively coupled to a smartphone, a tablet computer, a watch body, a watch band, or a wearable patch.

Embodiment 172. A method of preventing a physiological event, comprising:

estimating the risk of occurrence of a physiological event in a mammal according to the method of any one of embodiments 142-163; and applying at least one intervention measure that is commensurate with the prevention of the physiological event.

Embodiment 173. The method of embodiment 172, wherein estimating the risk and applying the intervention measure are performed automatically.

Embodiment 174. The method of any one of embodiments 172-173, wherein the physiological event is the onset of acquired epilepsy and the at least on intervention measure is an anti-epileptogenesis therapy.

Embodiment 175. The method of any one of embodiments 172-173, wherein the physiological event is an epileptic seizure and the at least on intervention measure is an anti-epileptic drug (AED).

Embodiment 176. A method of evaluating the effectiveness of an intervention measure, comprising:

estimating the risk of occurrence of a physiological event in a mammal according to the method of any one of embodiments 142-163;

applying at least one intervention measure that is commensurate with the prevention of the physiological event; and determining the effectiveness of the intervention measure.

Embodiment 177. The method of embodiment 176, wherein estimating the risk and apply the intervention measure are performed automatically.

Embodiment 178. The method of any one of embodiments 176-177, wherein the physiological event is the onset of acquired epilepsy and the at least on intervention measure is an anti-epileptogenesis therapy.

Embodiment 179. The method of any one of embodiments 176-177, wherein the physiological event is an epileptic seizure and the at least on intervention measure is an anti-epileptic drug (AED).

Embodiment 180. A method for detecting a brain-periphery coincidence in a mammal, comprising:

obtaining brain activity data that describes brain activity of the mammal over a period of time;

obtaining peripheral activity data that describes peripheral activity of the mammal over a period of time;

processing the peripheral activity data to generate independent peripheral activity data that is independent of behavioral state; and using a machine-learning model to detect presence of a brain-periphery coincidence in the mammal based on the brain activity data and the peripheral activity data.

Embodiment 181. The system of embodiment 64, wherein the one or more sensors are selected from sensors that records electrocardiogram (ECG) data, blood pressure data, and photoplethysmography (PPG) data.

Embodiment 182. The computer-implemented method of embodiment 21, wherein processing the one or more intervals comprises determining dlnRR at any time, T, using first window length $\tau_1$ and second window length $\tau_2$, according to the equation:

$$dlnRR(T)_{\tau_1,\tau_2} \overset{def}{=} \frac{1}{\tau_1} \frac{\overline{RRI}_{\tau_1}(T+\tau_1/2) - \overline{RRI}_{\tau_1}(T-\tau_1/2)}{\overline{RRI}_{\tau_2}(T)} \text{ wherein}$$

$$\overline{RRI}_{\tau_1}(T) = \frac{\tau_1}{N_{RR,\tau_1}(T)}$$

$$\overline{RRI}_{\tau_2}(T) = \frac{\tau_2}{N_{RR,\tau_2}(T)}$$

$N_{RR,\tau_i}(T) \overset{def}{=}$ fractional number of intervals $\in [T - \tau_i/2, T + \tau_i/2]$, and
wherein the fractional number of intervals include partial intervals that remain inside the first or second time windows.

Embodiment 183. The computer-implemented method of embodiment 182, wherein $\tau_1$ is greater than or equal to 100 ms.

Embodiment 184. The computer-implemented method of embodiment 182, wherein $\tau_1$ is greater than or equal to 1 second.

Embodiment 185. The computer-implemented method of embodiment 182, wherein $\tau_1$ is about 0.5 seconds and $\tau_2$ is about 1 second.

Embodiment 186. The computer-implemented method of embodiment 182, wherein $\tau_1$ is from about 10 to about 20 seconds and $\tau_2$ is about 30 seconds.

Embodiment 187. The computer-readable media of embodiment 52, wherein processing the one or more intervals comprises determining dlnRR at any time, T, using first window length $\tau_1$ and second window length $\tau_2$, according to the equation:

$$dlnRR(T)_{\tau_1,\tau_2} \overset{def}{=} \frac{1}{\tau_1} \frac{\overline{RRI}_{\tau_1}(T+\tau_1/2) - \overline{RRI}_{\tau_1}(T-\tau_1/2)}{\overline{RRI}_{\tau_2}(T)} \text{ wherein}$$

$$\overline{RRI}_{\tau_1}(T) = \frac{\tau_1}{N_{RR,\tau_1}(T)}$$

$$\overline{RRI}_{\tau_2}(T) = \frac{\tau_2}{N_{RR,\tau_2}(T)}$$

$N_{RR,\tau_i}(T) \overset{def}{=}$ fractional number of intervals $\in [T - \tau_i/2, T + \tau_i/2]$, and
wherein the fractional number of intervals include partial intervals that remain inside the first or second time windows.

Embodiment 188. The computer-readable media of embodiment 187, wherein $\tau_1$ is greater than or equal to 100 ms.

Embodiment 189. The computer-readable media of embodiment 187, wherein $\tau_1$ is greater than or equal to 1 second.

Embodiment 190. The computer-readable media of embodiment 187, wherein $\tau_1$ is about 0.5 seconds and $\tau_2$ is about 1 second.

Embodiment 191. The computer-readable media of embodiment 187, wherein $\tau_1$ is from about 10 to about 20 seconds and $\tau_2$ is about 30 seconds.

Embodiment 192. A computer-implemented method, comprising:
  receiving, by a system of one or more computers, brain data from a brain activity measurement device that describes brain activity of a mammal over a first period of time;
  receiving, by the system, periphery data from a peripheral activity measurement device that describes peripheral activity of a mammal over a second period of time;
  generating, by the system, one or more brain feature representations based on the brain data;
  generating, by the system, one or more periphery feature representations based on the periphery data;
  generating, by the system, one or more brain statistical distributions of the one or more brain features;
  generating, by the system, one or more periphery statistical distributions of the one or more periphery feature representations;
  identifying, by the system, one or more brain feature representations that fall outside of a predetermined range in the brain statistical distribution to generate a set of one or more target brain feature representations;
  identifying, by the system, one or more periphery feature representations that fall outside of a predetermined range in the periphery statistical distribution to generate a set of one or more target periphery feature representations;
  identifying, by the system, a probability of the one or more target periphery feature representations within a defined time window of one or more of the target brain feature representations to generate an estimated cumulative probability distribution;
  determining, by the system a brain-periphery temporal association between the one or more target brain feature representations and the one or more target periphery feature representations based on the estimated cumulative probability distribution; and
  providing, by the system, an indication of the temporal association.

Embodiment 193. A computer-implemented method, comprising:
  receiving, by a system of one or more computers, brain data from a brain activity measurement device that describes brain activity of a mammal over a first period of time;
  receiving, by the system, periphery data from a peripheral activity measurement device that describes peripheral activity of a mammal over a second period of time;
  generating, by the system, one or more brain feature representations based on the brain data;
  generating, by the system, one or more periphery feature representations based on the periphery data;
  generating, by the system, one or more brain statistical distributions of the one or more brain features;
  generating, by the system, one or more periphery statistical distributions of the one or more periphery feature representations;
  identifying, by the system, one or more brain feature representations that fall outside of a predetermined range in the brain statistical distribution to generate a set of one or more target brain feature representations;
  identifying, by the system, one or more periphery feature representations that fall outside of a predetermined range in the periphery statistical distribution to generate a set of one or more target periphery feature representations;

identifying, by the system, a probability of the one or more target brain feature representations within a defined time window of one or more of the target periphery feature representations to generate an estimated cumulative probability distribution;

determining, by the system a brain-periphery temporal association between the one or more target brain feature representations and the one or more target periphery feature representations based on the estimated cumulative probability distribution; and providing, by the system, an indication of the temporal association.

EXAMPLES

Exemplary Embodiment: Epileptogenesis Biomarker

There is critical need for diagnostic biomarkers of epileptogenesis to facilitate identification of patients at high-risk of developing epilepsy and to introduce effective anti-epileptogenic interventions.

In a post-infection model of acquired epilepsy, it was demonstrated that delayed brain-heart coincidences serve as a biomarker of epileptogenesis. In a murine model of post-cerebral malaria epilepsy mice were infected by malarial parasites, rescued, implanted, and monitored for development of recurrent spontaneous seizures. As with the human conditions of post-infection acquired epilepsy the model exhibits long and variable epileptogenesis periods. Long-term simultaneous measurements of the central activity via electroencephalography (EEG) and autonomic cardiac activity via electrocardiography (ECG) were utilized to quantitatively track brain-heart interactions during epileptogenesis. A state of vigilance independent representation of cardiac activity was developed to quantify fluctuations in the heart beat-to-beat intervals. Statistical tests of dependence between brain and cardiac representations were then used to identify abnormal transmission of activity from brain to heart. It was found that abnormal cortical discharges precede abnormal fluctuations in the cardiac rhythm at the resolution of single beat-to-beat intervals. The delayed brain-heart coincidence is significantly detected only in animals that become epileptic, is detectable as early as the onset of chronic measurements—2 to 14 weeks prior to first seizure—and increases during epileptogenesis. These findings indicate that delayed brain-heart coincidence serves as a biomarker of epileptogenesis and can be used for phenotyping, diagnostic, and therapeutic purposes.

For the wide range of human acquired epilepsies—developed after brain insults such as traumatic brain injuries, stroke, and infections—no biomarker that readily predicts and tracks epileptogenesis[26] currently exists.[17, 49, 50] Such diagnostic biomarkers are critical to identify patients at risk of epilepsy, introduce early and effective interventions to prevent establishment of epilepsy, and evaluate therapeutic efficacy of such treatments.

A murine model of post-cerebral malaria epilepsy was developed that duplicates elements of the human post-infection acquired epilepsy. As with the human condition, the model presented with long and highly variable epileptogenesis periods.[58] The brain-heart interactions were investigated as potential biomarkers of epileptogenesis. It was hypothesized that the frequency and strength of signals from brain affecting heart would vary with progression of epileptogenesis and therefore, if detected and quantified, could potentially serve as a biomarker of the process.

Almost all previous efforts to identify biomarkers of epileptogenesis have been focused on brain indicators such as high frequency oscillations[13, 18], and most recently permeability of blood brain barrier (BBB) in post-injury epilepsy.[4, 5, 6, 61] Despite the many benefits of brain-related biomarkers of epileptogenesis, the need for invasive or otherwise costly measurements to identify them severely limits their applicability.

Cardiac fluctuations are one of the more accessible symptoms of epilepsy.[1, 12, 15, 24, 39, 40] It has been shown in acute animal models of induced seizures that epileptic cortical discharges cause synchronized cardiac sympathetic and vagal nerve discharges.[38] The synchronicity is known as the Lockstep phenomenon (LSP).

The sensitivity of cardiac rhythmicity to epileptic discharges has been utilized for seizure prediction[16, 22, 23, 41, 47] and identification of epileptogenesis.[37] However, these efforts have had limited success partly due to the dependency of the conventional measures of cardiac rhythm—such as mean heart rate and heart rate variability parameters—on state of vigilance (SOV).[3, 7, 27, 51] In order to accommodate for SOV, cardiac related analyses are often restricted to periods of relatively stationary behavior such as observed[21, 28, 37, 43] or imposed rest.[2, 10, 20, 21] Therefore, these analyses are fragmented and incapable of continuous long-term tracking of brain-heart dynamics during epileptogenesis.

In order to address the challenges associated with conventional metrics of cardiac rhythmicity a new representation of the activity was generated and employed; the statistics of the representation are independent of behavior and state of vigilance. It was shown that in epileptic compared to non-epileptic animals, potentially abnormal cortical discharges precede disturbances in cardiac rhythm. The causal transmission of abnormal activity along the brain-heart axis starts early and progresses during epileptogenesis. These findings can be utilized to identify potential patients at risk of developing epilepsy, track the progression of epileptogenesis, and predict the occurrence of seizures.

Material and Methods

Experimental Design

All animal work was approved by and performed under administration of the Institutional Animal Care and Use Committee at the Pennsylvania State University.

Mice were infected with malarial parasite and monitored for signs of cerebral malaria. Infected mice were treated once they showed clear signs of cerebral malaria. Treated mice were allowed sufficient recovery period and then along with controls were implanted with electrodes. All implanted animals were monitored continuously for development of epilepsy and brain-heart interactions.

Infection and Treatment: Donor animals were infected from frozen stocks of Plasmodium berghei ANKA (PbANKA) or Plasmodium berghei NK65 (Pb-NK65) parasite, and blood was drawn on day 7 for inoculation into homologous experimental animals. Swiss Webster (SW), C57BL/6 (Charles Rivers Laboratory) and CBA/CaJ (CBA, Jackson Laboratory) male mice were infected by intraperitoneal injection of infected red blood cells from the donor animal. Age-matched control mice were inoculated with un-infected red blood cells from un-infected donor animals. The animals were treated by antimalarial medication, Artesunate (64 mg/kg dosage), for seven days starting from day 5 (C57BL/6-PbANKA or CBA-PbANKA), day 6 (SW-PbANKA) and day 7 (SW-PbNK65) post-infection[8].

Surgical Procedure and Care: Animals were implanted with electrodes to monitor brain activity at least five days post-treatment. Mice were anesthetized by inhalation of isofluorane throughout the surgery. After application of a long-lasting analgesic (Ketoprofen), Bupivacaine (5 mg/ml at a dose of 50 μl/100 g body weight), a local anesthetic, was injected subcutaneously in the scalp.

Four stainless steel screws (#000 self-tapping, Morris Co.) were placed over frontal (AP +1.5, ML ±2.5 mm) and Si (AP −2.3, ML +3.5 mm) cortices for measurement of electrocorticogram (ECoG). For the measurement of hippocampal field potentials 2 custom-made 50 μm (diameter) ultralow impedance micro-reaction chamber (pRC) electrodes[57] were implanted in dorsal hippocampus (AP −2.3, ML +2.0, DV −1.5 mm). A 3 mm length of 50 μm gold-plated 316L stainless steel wire was used to measure neck muscle activity (EMG). 3 mm length of the wire was prepared by dissolving the polyimide insulation in heated nano-strip solution (KMG Inc.). It was then electroplated with gold to avoid corrosion of active stainless steel in electrolytic environment of tissue. The EMG electrode was placed into a bluntly dissected opening within the nuchal muscles and further secured with polyglycolic acid absorbable sutures through the subcutaneous tissue. To measure cardiac activity we fabricated ECG leads from 50 μm gold-plated 316L stainless steel wire. The exposed end of the wire was formed into a ~2 mm diameter coil, which was then electroplated with gold to avoid exposure of stainless steel through possible cracks in the original gold-coated layer. The structure was then supported by a thin layer of biocompatible polymer (Slygard 184). A small incision was made in the chest and the electrode was placed in a bluntly dissected pocket-sized hole in precordium. The leads were subcutaneously routed from the chest to the head and connected to the head-mount. Two stainless steel screw electrodes at (AP −3.8, ML +3.5 mm) served as reference and ground. All coordinates were Bregma referenced.

At the completion of the surgery, animals were returned to their individual home-cages for recovery. Animals were housed individually in custom-made plexiglass cages each containing two enclosures with dimensions 6"W×12"D×12"H. Mice were allowed to recover and monitored for a minimum of 7 days post-surgery and had free access to food and water. After the recovery period, implanted mice were cabled to the acquisition board, which hangs down through a 1.5-inch hole in the ceiling of each enclosure. The board is connected to a custom-made commutator to allow for postural flexibility and free movement of the animals.

Data Collection: Animals were maintained under a 12-hour light/dark cycle with lights on between 6 am and 6 μm. During the dark period infrared LED arrays were used to illuminate the cage for continuous 24 hour video monitoring. Synchronized video (at 3 frames per second) and bio-potential recordings were recorded as 1 hour long files and stored on hard drives for further analysis. Bio-potential measurements were recorded via a custom-built acquisition board designed to provide 8 channels of high quality recordings with 24-bit digitization.[58] Internally amplified, digitized, and wide-band signals were sampled at 1000 samples/second sampling rate per channel and transmitted through a USB port to the computer.

Data Analysis: At least one week of data were analyzed for each animal. Longer datasets up to when the animals developed their first seizure, lost the ECG lead, or were sacrificed were used when available. Our inclusion criteria for each hour of data involved availability of viable ECG and at least one clean hippocampal depth and ECoG recordings. All recorded data were inspected via in-house written Labview (National Instruments) and MATLAB (MathWorks Inc.) programs that allow for simultaneous re-referencing, filtering, spectral analysis and annotation.

Figure 16:
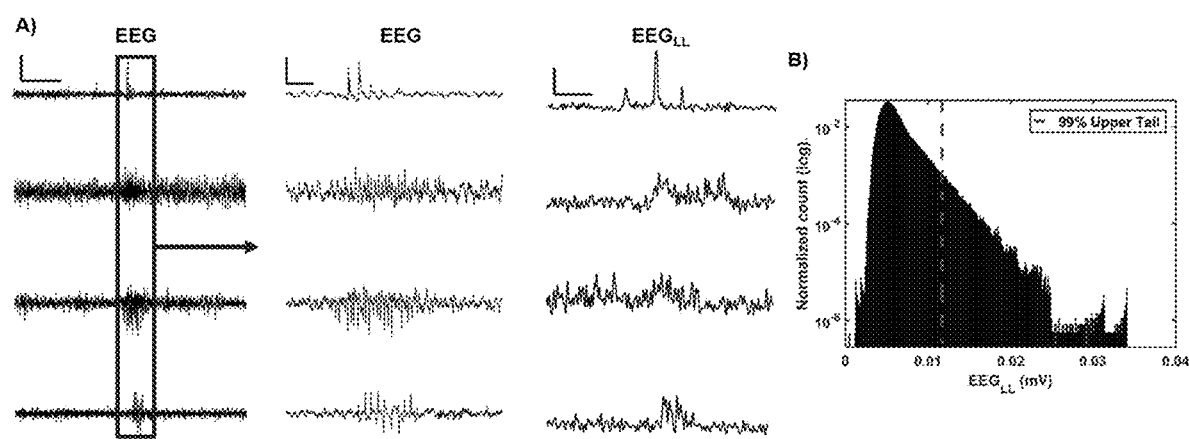
FIG. 16 is a series of charts depicting samples of cortical discharges and their associated line length, according to the Examples described herein. All traces are from epileptic animal #3 with seizure latency of 55 days post infection. (A) shows EEG traces bandpass-filtered between 15 and 250 Hz. Line length of the EEG was calculated with a window length of 300 ms. Shown are examples of abnormal brain discharges (at 16, 14, 8, 3 days—from top to bottom—prior to the first convulsive seizure) from one hippocampal channel. The events do not share a unique pattern in shape, duration, or amplitude during epileptogenesis. Vertical scale bar, 1 mV for the left and middle panels, 2 mV for the right panel. Horizontal scale bar, 5 s for left and right panels, 0.5 s for middle panel (B) shows the distribution of $EEG_{LL}$ from the same hippocampal channel in panel (A) for a one hour-long block of data at day 14 prior to the first seizure. By construction potentially abnormal brain events lead to large line length values in the upper tail of the distribution. We chose the upper 1% tail of the $EEG_{LL}$ distribution (indicated by the dashed red line) as the criteria for further analysis.

Cortical discharges were detected by a custom script implemented in MATLAB (Mathworks, Inc.). The raw EEG data were first bandpass filtered using 15-250 Hz pass band to preserve the high frequency nature of the discharges while eliminating the low frequency artifacts. Line length of the EEG signal was then computed using a sliding window of length ~300 ms. Line Length (LL) is essentially a discrete estimate of a continuous time-series and is calculated as the sum of distances between successive points in a window[19]:

$$LL(n) = \Sigma_{k=n-N}^{n} |x(k-1) - x(k)|$$

where x(k) is the kth point in the time-series within the window, N is the length of the sliding window and LL(n) is the normalized line length value at any given time point n. The cortical discharges do not share a unique pattern and vary in amplitude and duration throughout epileptogenesis. The window length was selected to be able to capture the variety of epileptic discharges including sharp waves, spikes and spike and wave complexes.[35] Examples of events that lay in the 1% upper tail of the line length distribution are illustrated in FIG. 16.

State of vigilance (SOV) was scored using a semi-automatic approach via Linear Discriminant Analysis (LDA) similar to the algorithm described in Sunderam et al. 2007).[59] Briefly, a training set for each animal was generated by visual SOV-scoring of 4-6 hours of video-EEG data within a day. The remaining 18-20 hours of data were set aside as out-of-sample test data. We marked onset of transitions between different states of vigilance: Rapid Eye Movement (REM), Non-Rapid Eye Movement (NREM), and Wake. Spectral power of the EEG across frequency bands of 0.5-4 Hz, 4-8 Hz, 8-12 Hz, 12-25 Hz, and 25-80 Hz as well as EMG total power were calculated as features for the automatic SOV classification of the test dataset.

The performance of the classifier for the out-of-sample test data and utilized the classified SOV as the new training set to recursively update the parameters of the LDA was further verified. For almost all animals under analysis the overall automated accuracy exceeded 90%.

Heart Rate Characterization:

The QRS complex was detected via a custom written MATLAB script (Mathworks, Inc.). The ECG is bandpass filtered from 30 Hz to 250 Hz to remove the low (DC drift) and high frequency artifacts. Line length was used to highlight the QRS complexes from the background ECG activity. The window size was selected to be 50 ms long to accommodate the ~40 ms long QRS complexes. The line length calculation is designed such that it introduces no phase shifts to the analysis and therefore preserves the QRS complex at the same time as it occurs in the original signal. In order to detect the QRS complex, specifically the R wave, the standard deviation of the line length time-series is estimated in non-overlapping 2-second long windows. The QRS complex is then detected via threshold crossing of 2-3 times the standard deviation from the mean.

The algorithm accounts for motion artifacts and DC glitches that inevitably escape filtering. The unfiltered ECG is convolved with a step function to highlight such glitches and their time-point. Any QRS complex detected within 20 ms of those glitches is then marked as a false detection and is excluded from analysis. We removed hour-long blocks of data with more than 2 glitches from the analysis. If the glitch-detection procedure fails, for each step function one QRS complex and 2 RR intervals are falsely excluded. Therefore, for the hour-long blocks that are included in the analysis, the maximum allowed estimated false detection rate is 4 RR intervals in 18000, which is negligible. The point-by-point RR interval and heart rate are then calculated from the time-series of the detected beats.

The cardiac representation dlnRR was calculated at any time, T, over window-lengths of $2\tau$ long:

$$dlnRR(T)_\tau \stackrel{def}{=} \frac{2}{\tau_1} \frac{\overline{RRI}(T+\tau/2) - \overline{RRI}(T-\tau/2)}{\overline{RRI}(T+\tau/2) + \overline{RRI}(T-\tau/2)} \text{ Where}$$

$$\overline{RRI}(T) = \frac{\tau}{N_{RR}(T)}$$

$N_{RR}(T)$ = fractional number of intervals $\in [T - \tau/2, T + \tau/2]$, where fractional number of intervals include partial intervals that remain inside the window. Therefore, the discretization effects are minimized.

Figure 17:
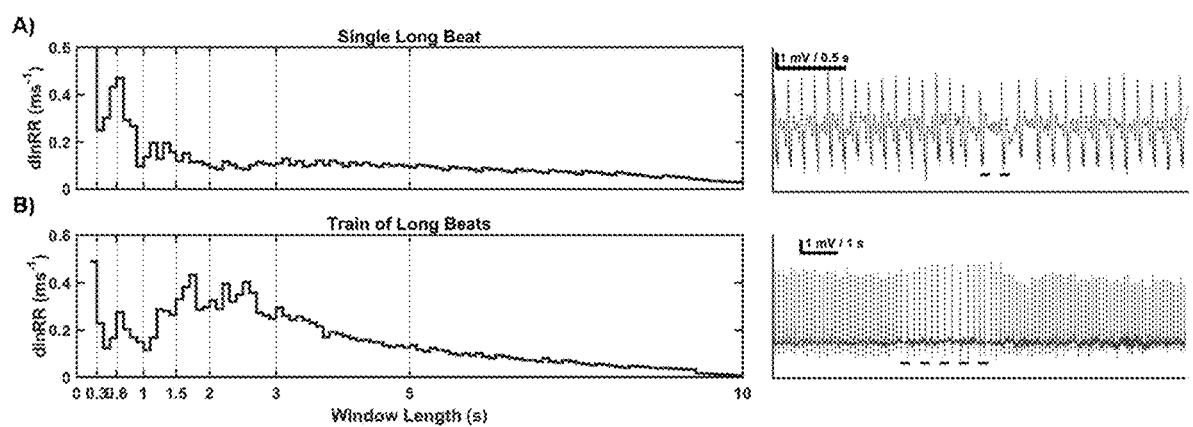
FIG. 17 is a series of charts depicting the effect of window-length in sensitivity of dlnRR to abnormally long RR intervals, according to the Examples described herein. dlnRR is calculated for two beat times associated with a following (A) single RR interval and (B) a train of 14 long RR intervals (marked by the dashed black lines). For single long RR intervals smaller window-lengths ($\tau \leq 0.7$ s) capture the effect sufficiently. In contrast, for the train of long RR intervals larger $\tau$ is required. In either cases once the window length ($\tau$) becomes too large, dlnRR values are comparable to the mean dlnRR of the RR interval time-series which is zero.

In the limit as $\tau \to 0$, if the derivative of RR-time series was defined, this representation becomes the derivative of the logarithm of the RR interval:

$$\lim_{\tau \to 0} dlnRR(T)_\tau \stackrel{def}{=}$$

$$\lim_{\tau \to 0} \frac{2}{\tau} \frac{\overline{RRI}\left(T+\frac{\tau}{2}\right) - \overline{RRI}\left(T-\frac{\tau}{2}\right)}{\overline{RRI}\left(T+\frac{\tau}{2}\right) + \overline{RRI}\left(T-\frac{\tau}{2}\right)} = \frac{\frac{d}{dT}\overline{RRI}(T)}{\overline{RRI}(T)} = \frac{d}{dT}\ln\overline{RRI}(T)$$

dlnRR is a local measure that is proportional to the normalized RR interval in the window length over which it is calculated. Therefore, the window length $\tau$ directly affects dlnRR's capability to efficiently track and represent the underlying RRI time-series. If $\tau$ is too small, then dlnRR is dominated by normal fluctuations between consecutive RR intervals induced by motion or cardio-respiratory coupling. If $\tau$ is too large, then the numerator becomes insensitive to single RRI fluctuations, while the denominator is too long to follow state-dependent changes in the RR interval time-series (FIG. 17). However, in FIG. 9C-D it is shown that choice of $\tau$ does not affect the behavior-related differences in distributions of both dlnRR and RMSSD.

Statistical Analysis:

Distributions of $EEG_{LL}$ and dlnRR are not Gaussian, therefore we used non-parametric rank-order statistics. In order to find the correlation between brain and heart, both $EEG_{LL}$ and dlnRR distributions were casted into the rank space. For the brain- or cardiac-triggered analysis we selected the $EEG_{LL}$ or dlnRR ranks above 99% and found their corresponding rank (dlnRR) or rank ($EEG_{LL}$) values. The analysis for identification of brain-heart coincidences was based on statistical tests of dependence of the $EEG_{LL}$ and dlnRR rank distributions with the null hypothesis of random rank selection. The ranks were computed over either one hour or one-day long blocks of data approximating nearly uniform selection of ranks. Because our samples sizes, N, are very large (N>>100), the normalized rank-sum distribution are well approximated as Gaussian with means of 0.5 and standard deviation of $$\frac{1}{12\sqrt{N}}.$$

Figure 12:
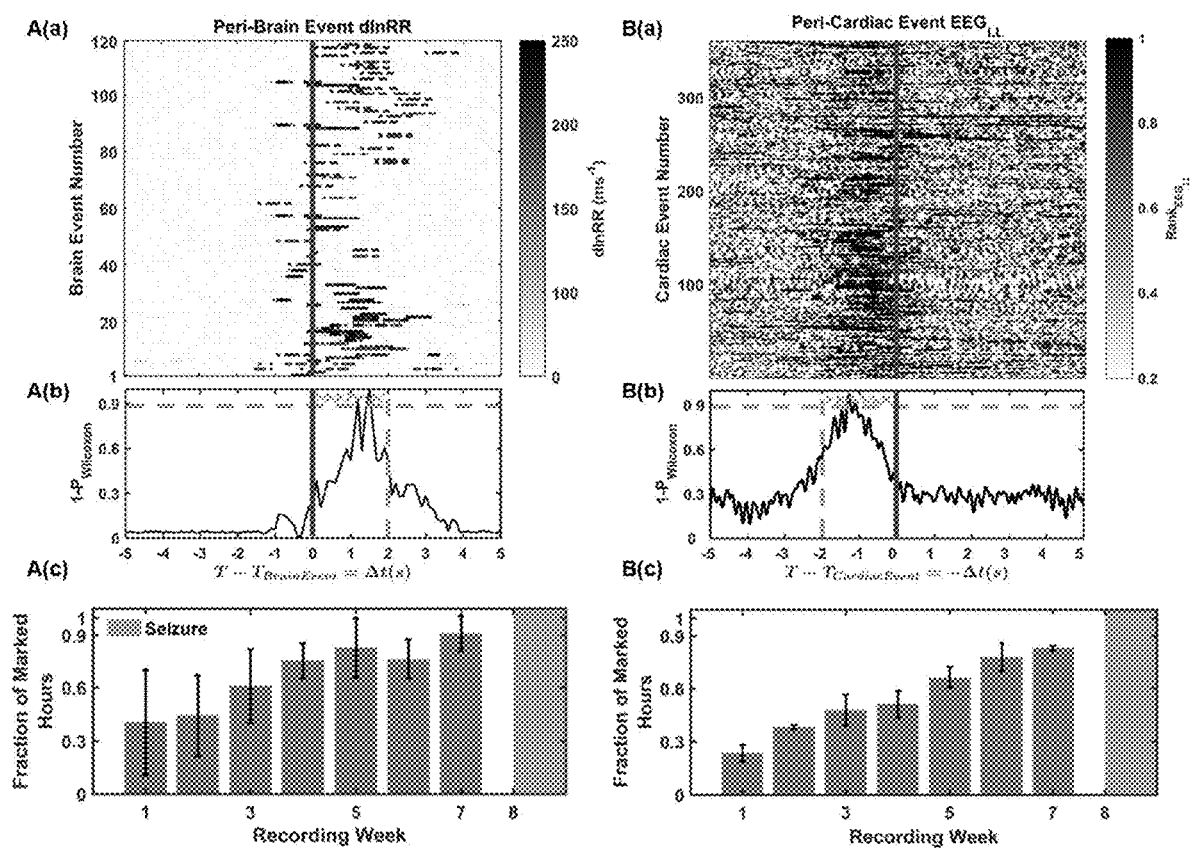
FIG. 12 is a series of charts depicting event-triggered analysis of brain-heart coincidence, according to the Examples described herein. Isolated, potentially abnormal events are detected from normalized rank ($EEG_{LL}$(t))≥0.99 (A) for brain- or rank (dlnRR(t))≥0.99 (B) for heart-triggered analyses. (A.a, B.a) Peri-event time-series of the heart representation with respect to brain-event times (A.a) or brain representation with respect to heart-event times (B.a) shown for the same animal and hour as in FIG. 10 and FIG. 11. (A.b,B.b) Complement of the Wilcoxon rank-sum test P-value, 1−PWilcoxon, as a function of time-offset ($\Delta t$) from detected abnormal events (A.b) for brain events and (B.b) for heart events. The event times are marked by the solid red lines. The low probability indicates that these representations are significantly interdependent for time-offsets of $\Delta t \in [0,2]$ s. Specifically, for brain-triggered analysis at $\Delta t$=1.5 s, PWilcoxon=0.002 and for heart-triggered analysis at $\Delta t$=−1.1 s, PWilcoxon=0.001. (A.c, B.c) Fraction of marked hours with brain-heart coincidence averaged per week of recording for this animal for (A.c) brain-triggered events and (B.c) heart-triggered events. Hours were marked for existence of brain-heart coincidences for (1−PWilcoxon) ≥0.9 for $\Delta t \in [0,2]$ s (hash-marked red area in A.b and B.b). Error bars reflect the standard deviation of these measures between days. These fractions steadily rise through the epileptogenic period leading to this animal's first seizure.
Figure 13:
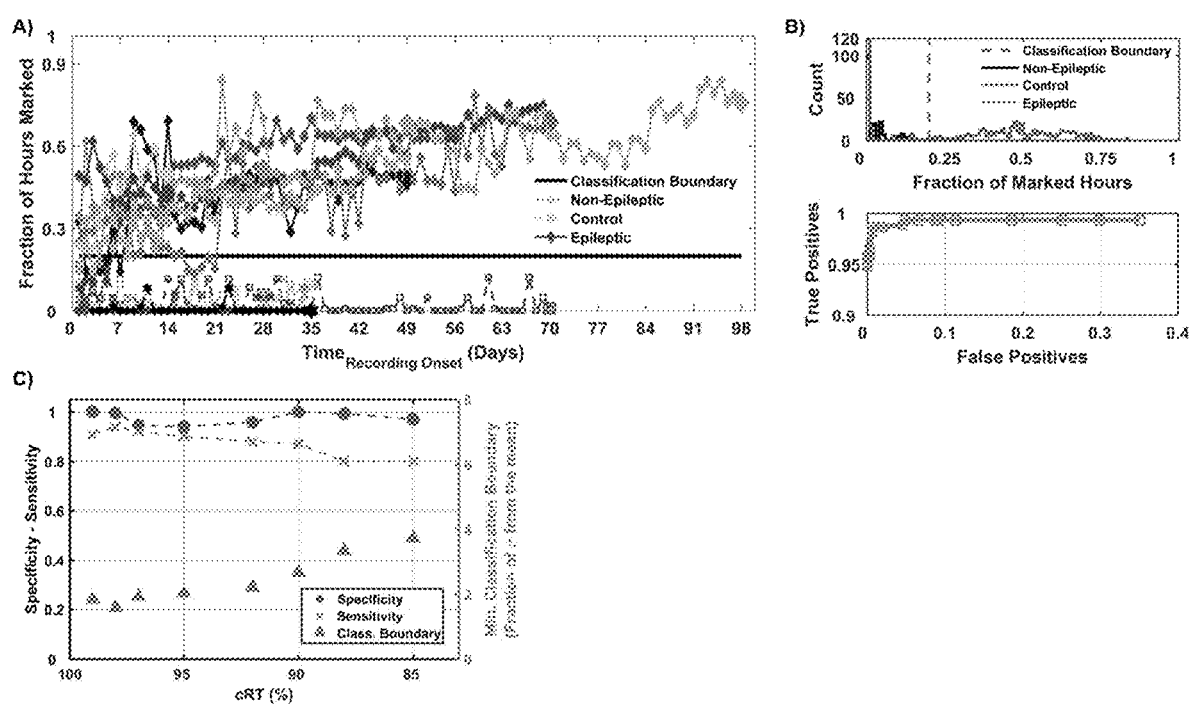
FIG. 13 is a series of charts depicting evolution of Brain-Heart coupling in epileptic, non-epileptic, and control mice using hour-long blocks of data, according to the Examples described herein. (A) depicts daily fraction of hours marked for existence of brain-heart coincidence are shown for epileptic (colored diamond markers), non-epileptic (colored square markers), and control (hexagons) mice; based on a conditional rank threshold (cRT) of 0.99. The fractions increase during epileptogenesis with large fluctuations within the first 21 days of the recordings. In contrast, they remain low for animals that were rescued from cerebral malaria but did not become epileptic (non-epileptic) and controls. The hours are marked for existence of brain-heart coincidences if they have conditional $EEG_{LL}$ rank-sums larger than a specified rank-sum threshold. The rank-sum threshold is selected to maximize classification specificity for a collection of every other days from the first 14 days of recordings. Mice were then classified according to a classification boundary on fraction of marked hours to maximize specificity (Black solid line). This boundary is represented by the gray dashed line separating epileptic, non-epileptic, and control distributions in the top panel of (B). Shown in the bottom panel of (B) is the Receiver Operating Characteristic (ROC) curve using the boundary and fraction of marked hours. All epileptic mice but one (light blue trace in panel (A)) are separated from non-epileptic and control mice after 21 days of recording. (C) depicts specificity (blue circles), sensitivity (orange crosses), and the minimum conditional rank-sums (gray triangles) selected as the classification boundary to mark hours for brain-heart coincidences, as a function of conditional rank threshold (cRT).
Figure 14:
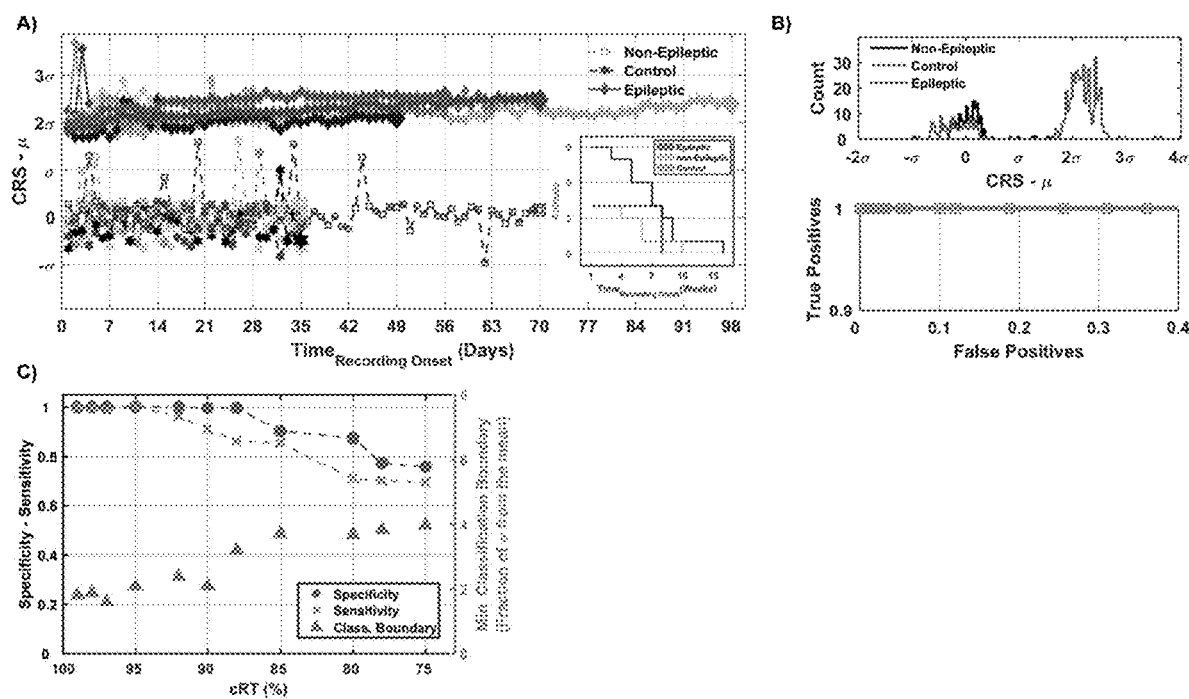
FIG. 14 is a series of charts depicting evolution of brain-heart coupling in epileptic, non-epileptic, and control mice using day-long blocks of data, according to the Examples described herein. (A) depicts conditional rank-sum (CRS) of the cardiac-triggered brain events from each day for all animals: epileptic mice (colored diamond markers), non-epileptic mice (colored square markers), and control mice (hexagons); based on conditional rank threshold (cRT) of 0.99. The color-coding for all mice is the same as in FIG. 13A. Similar to daily fractional detections in FIG. 13A, this statistic increases during epileptogenesis for epileptic mice while it remains low for non-epileptic and control mice. All epileptic animals—including the animal that was transiently misclassified in FIG. 13A—are fully separable from non-epileptic and control mice as shown in the distributions of these animals in the upper panel of (B) (green for epileptic, black for non-epileptic, and magenta for controls). Therefore, this statistic provides a classifier with complete sensitivity and specificity (shown via the ROC curve in bottom panel of (B)). Epileptic mouse #9 in FIG. 10 is marked by the purple trace. Shown in the inset of panel (A) is the number of epileptic (gray), non-epileptic (green), and control (magenta) alive at days post-recording onset. (C) depicts specificity (blue circles) and sensitivity (orange crosses), as a function of conditional rank threshold (cRT). The sensitivity values are computed based on a classification boundary to maximize specificity. As the cRT is relaxed to include more intermediary values of the rank (dlnRR(t)) distribution, the sensitivity and specificity decrease and the classifier performs worse. Gray triangles indicate the minimum classification threshold that maximizes specificity in the units of fraction of standard deviation away from the mean of the control and non-epileptic distributions.
Figure 19:
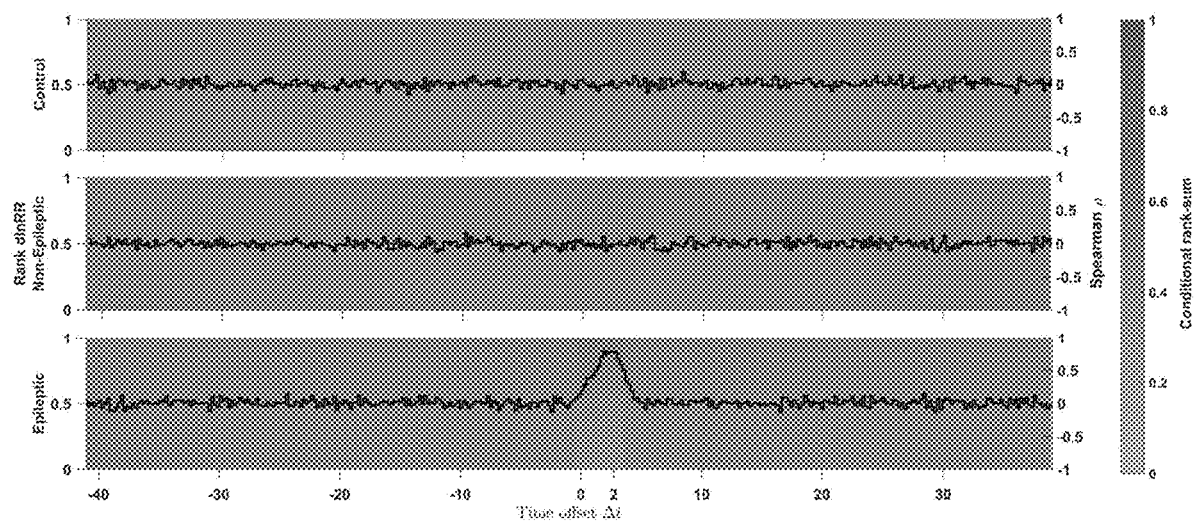
FIG. 19 is a chart showing fluctuations in the brain ($EEG_{LL}$) and cardiac (dlnRR) representations with a 0-2 s delay are consistent with Spearman's correlation, according to the Examples described herein. Same distribution of the normalized conditional rank-sum of $EEG_{LL}$ values as in FIG. 18, for different time-offsets ($\Delta t$). Overlaid in black lines are the correlation coefficients ($\rho$) of the Spearman's Rank Correlation between the distributions of $EEG_{LL}$ and dlnRR ranks (right y-axis indicates values of the correlation coefficient). Consistent with the conditional rank-sum (CRS), Spearman's $\rho$ remains close to zero with small fluctuations for the control and non-epileptic mice as well as outside the range of $0 \leq \Delta t \leq 2$ s for the epileptic mouse. In contrast, $\rho$ increases within $0 \leq \Delta t \leq 2$ s for the epileptic mouse which indicates that the $EEG_{LL}$ and dlnRR rank distributions are correlated with a positive time-delay. Same data as in FIG. 18.
Figure 20:
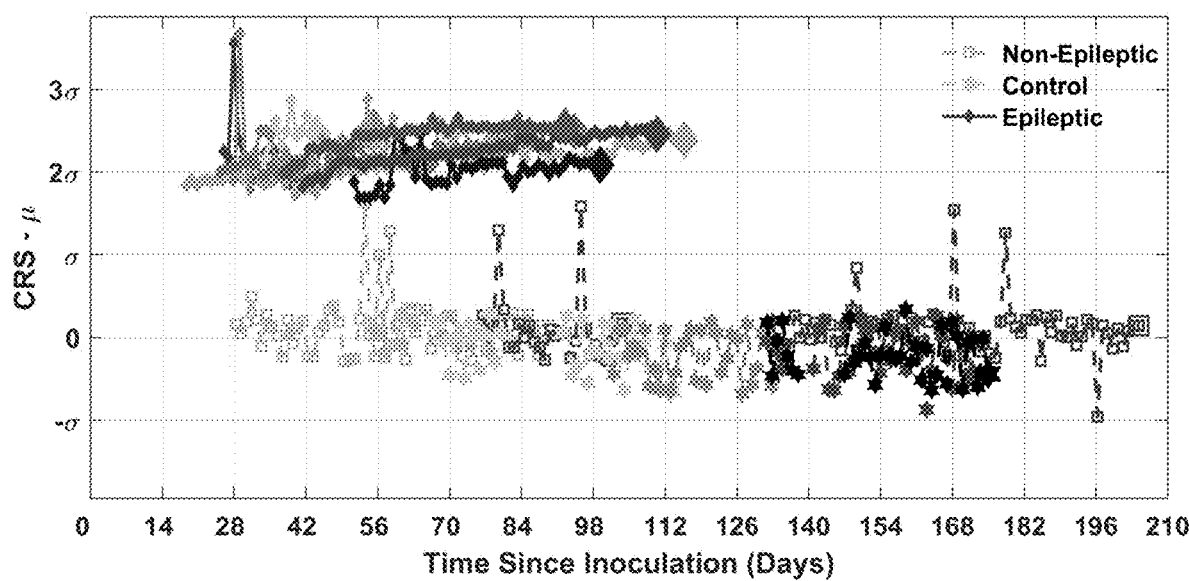
FIG. 20 is a chart depicting evolution of Brain-Heart coupling in epileptic, non-epileptic, and control mice as a function of time since inoculation, according to the Examples described herein. Conditional rank-sum (CRS) of the cardiac-triggered brain events from each day for all animals: epileptic mice (colored diamond markers), non-epileptic mice (colored square markers), and control mice (hexagons). The evolution is with respect to time since inoculation which for epileptic and non-epileptic mice stands for time since infection and for control mice represents time since inoculation with uninfected red blood cells. The color-coding for all mice is the same as in FIG. 13A and FIG. 14A.

All rank-ordered statistics are then presented either in absolute units (FIG. 10-12 and FIG. 18-19) or as means and standard deviations of the rank-sum distributions (FIG. 13-14 and FIG. 20). Expected false detection rates from null hypotheses with P<0.005 are identified.

Results

A combination of mouse and parasite strains were examined for development of post-cerebral malaria epilepsy[58]: Swiss-Webster (SW), C57BL/6, and CBA/CaJ mice and *Plasmodium berghei* ANKA (PbANKA) and *Plasmodium berghei* NK65 (PbNK65) parasites. Young mice (P23) received intraperitoneal injection of infected red blood cells from a donor animal. The infected animals were treated by antimalarial medication once they showed signs of severe cerebral malaria such as convulsions and coma. Mice were then implanted with hippocampal, cortical and electromyography (EMG) electrodes at least five days post-treatment. A cohort of the animals also received electrocardiography (ECG) electrodes to monitor cardiac activity. Continuous recording started after ample recovery time and lasted for periods of at least 2 weeks until the animals expired.

From the animals that survived to recordings, 75% developed epilepsy as defined by observation of 2 or more seizures with durations longer than 10 s and clear behavioral manifestations as shown in FIG. 15 (see Ssentongo et al. 2017[58] for more detailed description of the model statistics). The epileptic animals all had relatively long latencies to the first seizure with median of 5 to 10 weeks post-infection (Supplementary Table 1). Further, it was observed incidents of sudden unexplained death in epilepsy (SUDEP) and other seizure-related mortalities such as gradual decline of physiological signs—heart rate and behavior—after multiple seizures in 10% of the epileptic cohort.

Figure 7:
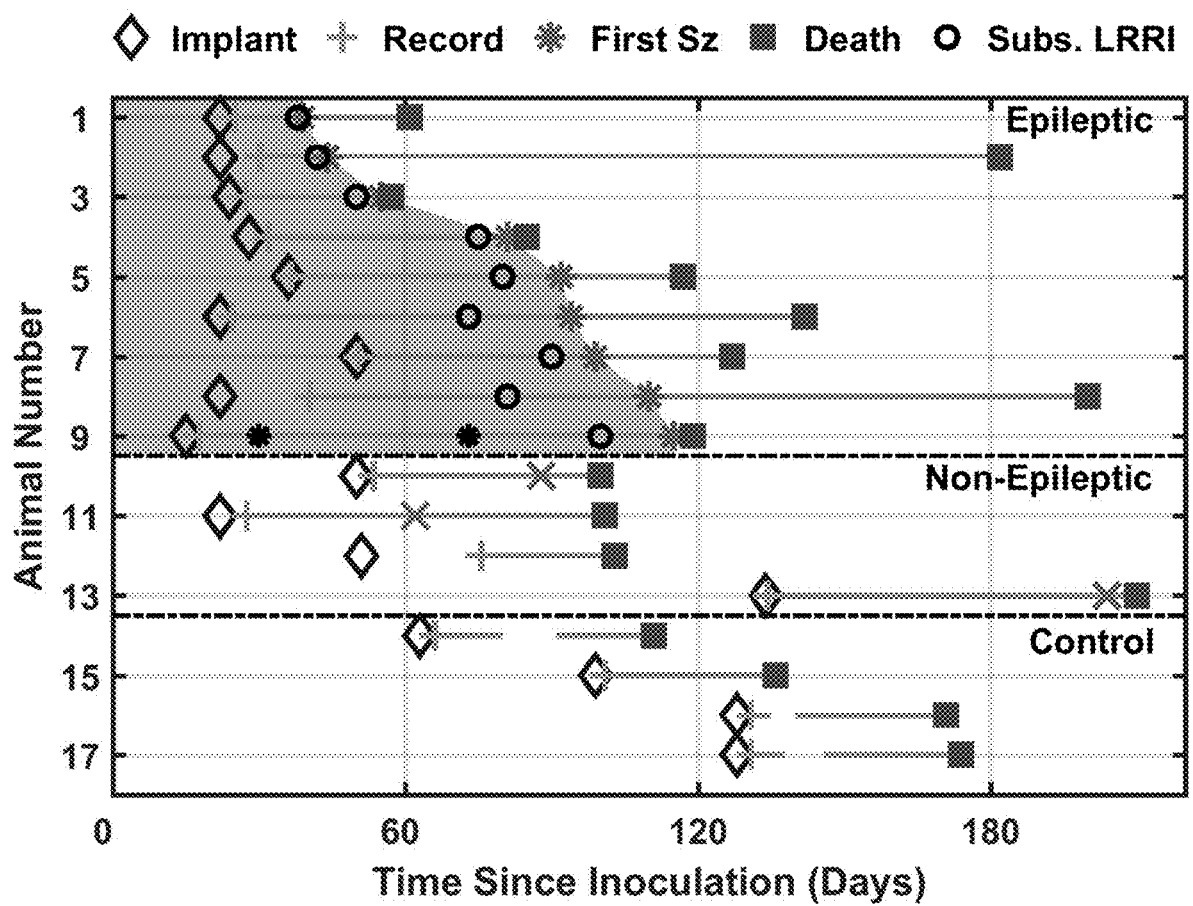
FIG. 7 is a chart of a time course of events from infection with a malarial parasite in mice through death, according to the Examples described herein. After animals received treatment and allowed ample time for recovery, they were implanted and continuously monitored (orange lines). For animals that became epileptic, the latency to the first convulsive seizure (marked with magenta asterisks) ranged from 39 days to 115 days post-infection (shaded gray area). Because the physiological measurements did not start until the animals fully recovered from cerebral malaria, we assume that we only captured part of the epileptogenesis process. Instances of substantially long single RR intervals (Subs. LRRI) were present in all epileptic mice. The onset of appearance of such events is marked by black open circles. The black dashed lines separate epileptic, non-epileptic, and control mice. Non-epileptic mice were rescued from cerebral malaria and chronically recorded from but did not develop seizures. Data prior to the first convulsive seizure for epileptic mice (shaded gray area), and until ECG leads broke in control (entire recording time) and non-epileptic mice (dark green crosses) were analyzed. Data from 30 and 73 days post-infection from animal #9 (black asterisks) are used in later FIG. 10 and FIG. 18.

To investigate the brain-heart coupling during epileptogenesis, 9 epileptic mice that had viable ECG electrodes at least until their first seizure were selected for further analysis. This subset is representative of the original epileptic cohort both in terms of seizure rate and distribution as well as latency to first convulsive seizure (FIG. 7, FIG. 15). Cardiac activity was monitored during epileptogenesis, which ranged from minimum of 39 days to a maximum of 115 days post-infection (FIG. 7). In addition to the 9 epileptic mice, 4 animals that were rescued from cerebral malaria but did not become epileptic (termed non-epileptic mice), and 4 control mice (treated but not infected) were investigated. Animals were excluded from analysis when they developed spontaneous recurrent seizures or their ECG lead became unviable.

Substantially Long RR Intervals are Preceded by Epileptic Discharges

Cardiac arrhythmia manifested in visually distinguishable, substantially long RR interval in the period between implant and the occurrence of the first convulsive seizure. RR interval (RRI) is the interval between successive R waves, where R is marked by the peak of the QRS complex in each heartbeat. Substantially long RRIs were quantitatively identified by a user-defined criteria of any interval longer than 150 ms, which is approximately 150% of the mean RR value. It was found that high-amplitude, high-frequency cortical discharges precede instances of long RRI by at least 500 ms. An example of such precedence is shown in FIG. 8A.

Figure 8:
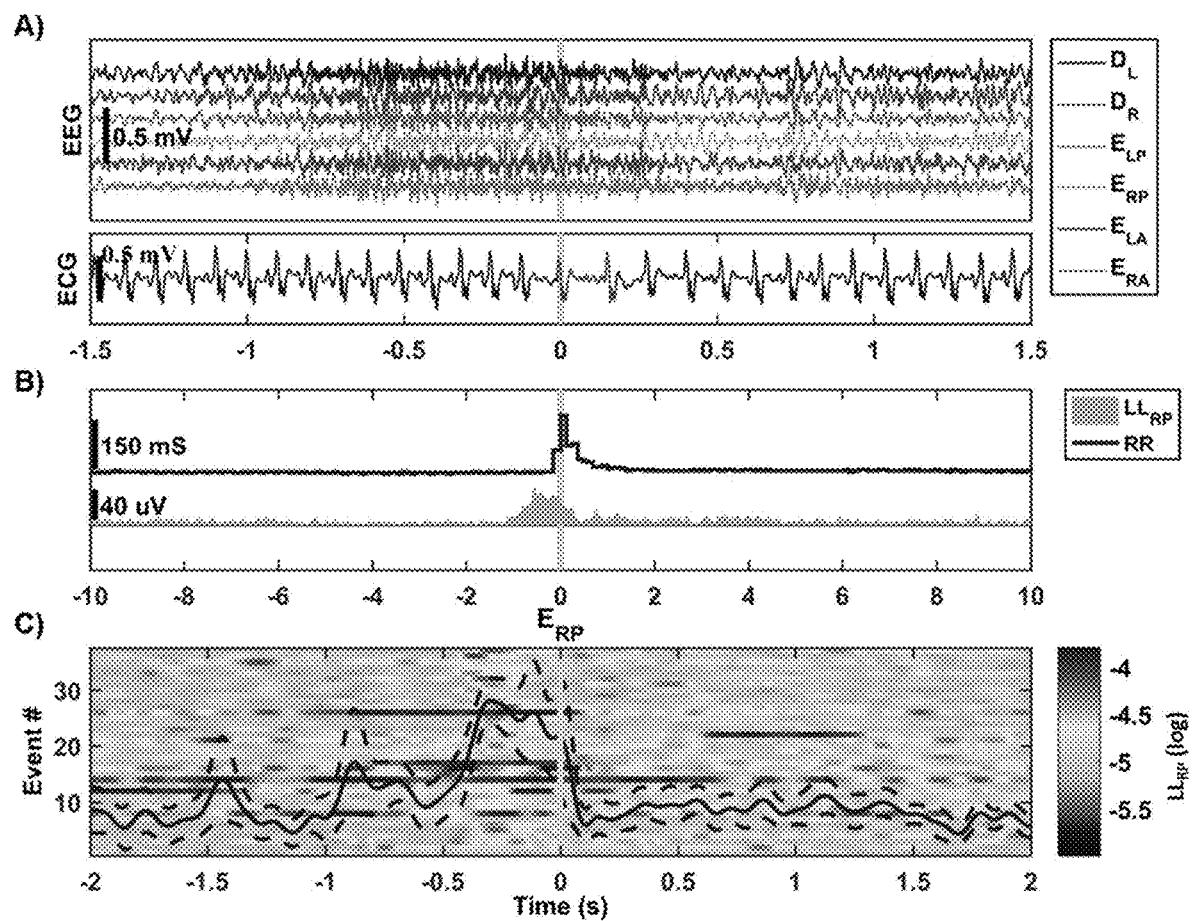
FIG. 8 is a series of charts depicting substantially long RR intervals preceded by epileptiform cortical discharges, according to the Examples described herein. Instances of abnormal cortical discharges preceding abnormally long RR intervals are shown for one animal. Substantially long RR intervals are detected via the user-defined threshold of any interval longer than 150 ms. (A) shows high amplitude, high frequency EEG activity immediately precedes the long-RR interval (Red trace in ECG) onset of which is marked by the gray vertical bar. Time-series traces of hippocampal activity are recorded from left and right dorsal hippocampi ($D_L$, depth hippocampus left and $D_R$, depth hippocampus right), electrocorticogram (ECoG) recorded from frontal and Si cortices ($E_{LA}$, ECoG left anterior, $E_{RA}$, ECoG right anterior and $E_{LP}$, ECoG left posterior, $E_{RP}$, ECoG right posterior). ECG is bandpass-filtered between 15-250 Hz to eliminate DC artifacts and overall trend of the signal. (B) shows that in the same event as in (A), the line length of the brain activity at the right posterior cortical site ($LL_{RP}$)—computed over 300 ms long windows—increases preceding a long RR interval. (C) shows almost all substantially long RR intervals (31 out of 35) are preceded by large increases in the line length of the right posterior ECoG shown in color coded values. Overlaid is the average of the line length of the right posterior ECoG activity (blue solid line) for all detected abnormally long RR intervals along with the 95% confidence bounds (dashed blue lines). The Data extracted from animal #3 (FIG. 7). (A) and (B) are from 50 days post infection, 11 AM.

To highlight cortical discharges the line length of EEG (EEG$_L$a) was calculated using a sliding window of length 300 ms. The window length was selected such that it accommodated a variety of discharges including sharp waves, spikes, and spike and wave complexes.[35] Different instances of cortical discharges and their line length representations are shown in Supp. FIG. 7A. In FIG. 8B, a noticeable increase in EEG$_{LL}$ of the right posterior cortical electrode immediately before the rise in the RRI time-series associated with the event shown in FIG. 8A was demonstrated. Similar increases in the EEG$_{LL}$ were observed in the rest of the cortical and hippocampal channels. Inspection of the associated recording video confirmed that these long events were sub-convulsive. For the animal presented in FIG. 8, this particular temporal pattern was observed for the majority (31 out of 35) of exceedingly long RRIs, as illustrated in FIG. 8C.

A limited number of substantially long RRIs was observed for each animal that became epileptic. This ranged from 10 to 53 instances of long RRIs out of the 7-84 million marked from the recording times prior to the animals' first seizures. Almost all of these cases were preceded by sub-convulsive cortical and hippocampal discharges reflected in increased EEG$_{LL}$. Much more complex cardiac arrhythmias associated with the subsequent seizures in the epileptic animals were observed, including peri-ictal tachycardia, bradycardia, and post-ictal asystole. Therefore, it was hypothesized that abnormal, potentially epileptic-like, brain activity influences cardiac function.

The substantially long RRIs—longer than 150 ms—were observed starting many weeks into the epileptogenesis process (black open circles in FIG. 7). It is therefore possible that earlier in epileptogenesis abnormal brain activity would induce more subtle changes in duration of single RRIs and if the size of such an effect would continuously increase prior to the first seizure. The long latencies to the first convulsive seizure in our epileptic animals provide a platform to study the brain-heart coupling and its evolution during epileptogenesis. Detection of abnormal transmission early in epileptogenesis requires a cardiac measure that identifies small abnormal fluctuations in the RRI, as well as the statistical power to correlate them with small fluctuations in brain activity.

State-Independent Cardiac Representation: dlnRR

Distributions of conventional metrics of cardiac activity such as absolute duration of RRIs or heart rate variability (HRV) measures vary with behavioral states and are highly sensitive to transitions between such states.[3, 7, 27, 51] Detrending methods such as detrended fluctuation analysis (DFA)[48] attempt to eliminate the behavioral state dependency. These methods however fail to quantify non-stationarities at the resolution of single RR intervals.[8, 25] In order to investigate the relationship between cortical activity and cardiac rhythm, a new and more flexible cardiac representation sensitive to small but abnormal fluctuations in the duration of single RRIs was developed.

A representation at time T was defined, proportional to the difference in mean RRI before and after T, computed in windows $\tau$ wide, normalized by the average RR interval over the period $2\tau$. This representation is denoted dlnRR(T) because it is the discrete estimate of the logarithmic derivative of the RR interval.

Figure 9:
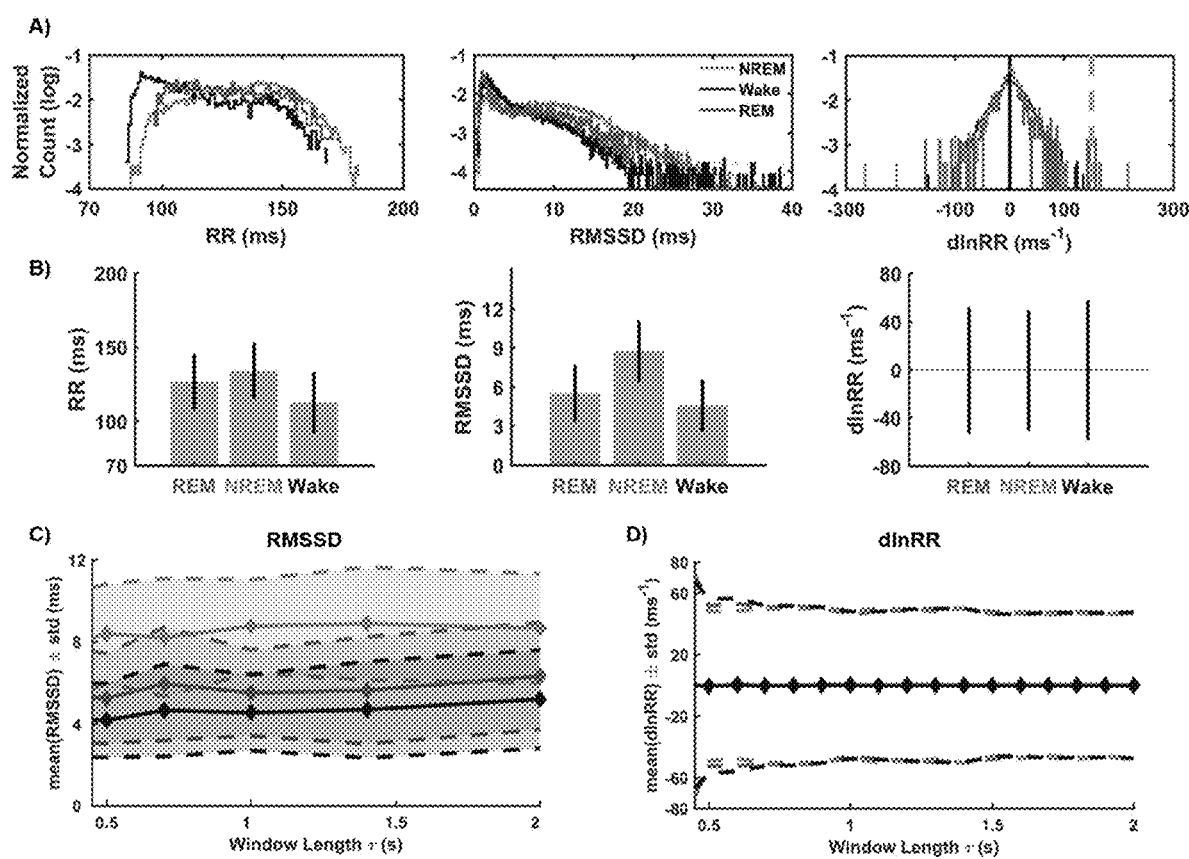
FIG. 9 is a series of charts depicting temporal measures of cardiac rhythm for a control mouse according to the Examples described herein. (A) depicts distributions of dlnRR, RMSSD, and RRI for different states of vigilance (SOV) pooled from 2 weeks of recordings from control mouse #2. Distributions of dlnRR and RMSSD are calculated using identical window lengths ($\tau$) of 0.5 s. RMSSD and RR intervals have varying distributions across different states of vigilance; two-sample Kolmogorov-Smirnov test, REM and NREM ($p_{RR}$=6.41-6, $p_{RMSSD}$=9.1e-4), REM and Wake ($p_{RR}$=5.9e-8, $p_{RMSSD}$=5.95e-4), and NREM and Wake ($p_{RR}$=3.9e-4, $p_{RMSSD}$=1.12e-4). The distribution of dlnRR remains similar and approximately symmetric with near-zero mean for all states of vigilance. By construction, for the $\tau$=0.5 s, single long RR intervals lead to values in the upper tail of the dlnRR distribution. Dashed gray line indicates the boundary for the 99% upper tail of the dlnRR distribution. (B) depicts mean and standard deviation of RR intervals, RMSSD, and dlnRR distributions across different SOVs. (C) depicts mean (solid lines) and standard deviation (dashed lines) of RMSSD calculated over different window lengths ($\tau$). For all r, within the physiologically relevant range of 5-20 RR intervals, mean and standard deviation of RMSSD distributions for different states of vigilance are different. (D) depicts mean (solid lines) and standard deviation (dashed lines) of dlnRR calculated over a sweep of T remain relatively similar for all states of vigilance.

The distribution of dlnRR is approximately symmetric with near-zero mean. Unlike conventional measures of cardiac activity such as heart rate or HRV parameters (i.e. root mean square of the successive differences (RMSSD) of the RRI), distribution of dlnRR is not influenced by changes in behavioral state (FIG. 9A-B).

Sensitivity of dlnRR to choice of $\tau$ is discussed in the supplementary materials and methods section. For these analyses $\tau$ was selected to be 0.5 s long to calculate dlnRR, mean heart rate, and the temporal HRV parameter (RMSSD). For r=0.5 s single longer RRIs that occur within the window after time T result in large positive values of dlnRR in the tail of the distribution.

Epileptiform Discharges Cause Abnormally Long RR Intervals dlnRR was used as a state-independent representation of cardiac activity. First, for each one-hour block of recordings, QRS complexes were detected from the ECG and dlnRR was calculated for each beat time with the $\tau$ of 0.5 s. For EEG, we utilized line length as a representation of brain activity. Line length of intracranial EEG (iEEG) from one hippocampal lead was selected for further brain-heart correlation analyses. In FIG. 8 and FIG. 16A, it is shown that line length of EEG (EEG$_{LL}$ calculated over 300 ms long windows) sufficiently represented high frequency, high amplitude brain events.

In order to identify any transmission along brain-heart axis, the analysis was based on statistical tests of dependence of the EEG$_{LL}$ and dlnRR distributions. It was hypothesized that if abnormal cortical activity is transmitted from brain to heart, then coincidences with positive time-delay between potentially abnormal values of EEG$_{LL}$ and potentially abnormal values of dlnRR would be observed. By construction, it was hypothesized that potentially abnormal events have values in the tails of the distributions of dlnRR for heart and EEG$_{LL}$ for brain. Due to the non-normality of the EEG$_{LL}$ and dlnRR distributions the hour/day long estimates of the distributions were transformed into the rank space and non-parametric tests (Wilcoxon rank-sum and Spearman's rank correlation) were utilized for statistical evaluations.

Figure 10:
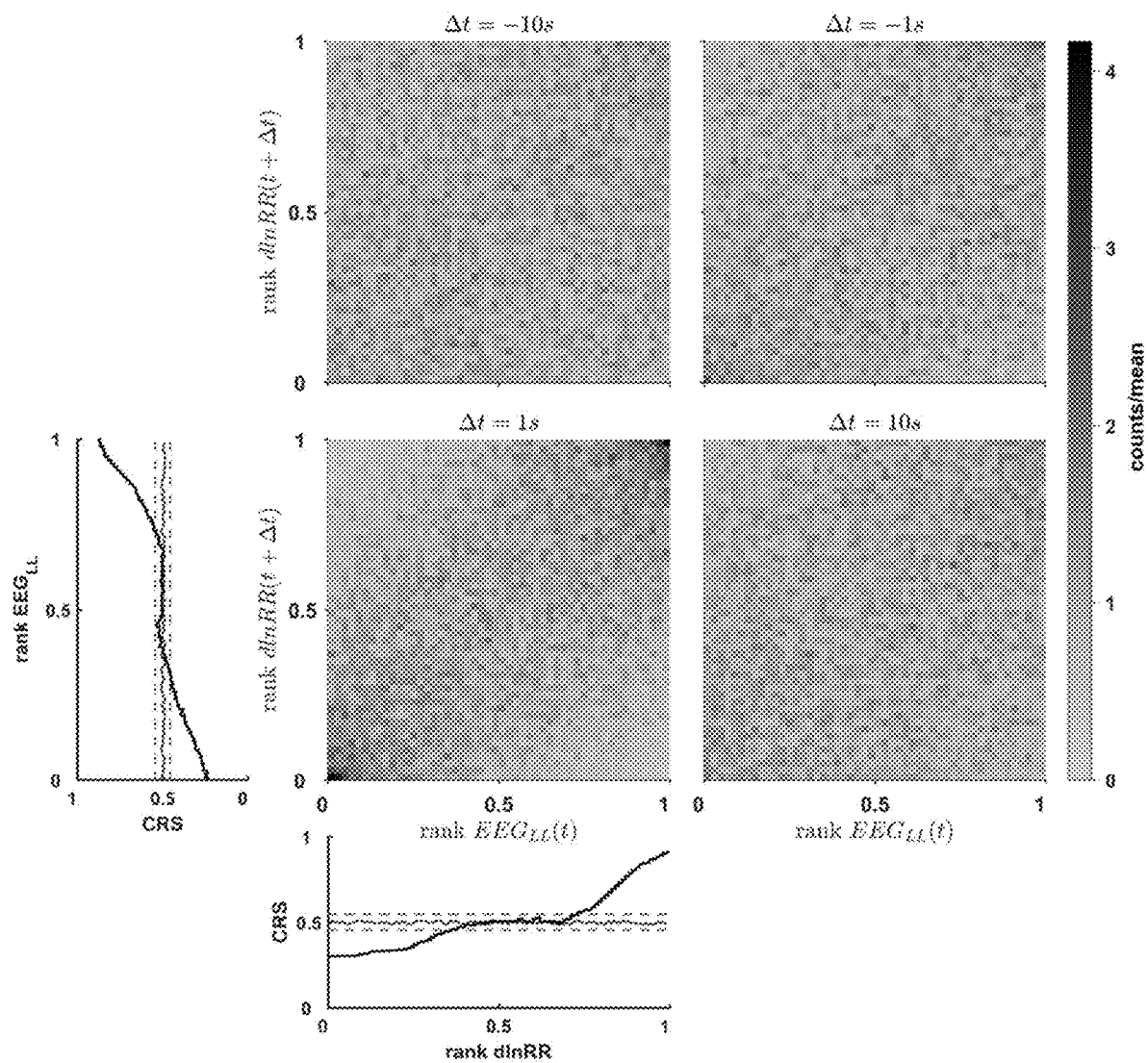
FIG. 10 is a series of charts depicting joint rank distributions of brain ($EEG_{LL}$) and cardiac representations (dlnRR) over different time offsets ($\Delta t$) for an hour-long block of data, according to the Examples described herein. The representations are first transformed into the rank space. The joint rank distributions are then calculated for different time offsets between EEG and dlnRR, P(rank $EEG_{LL}$(t), rank dlnRR(t+$\Delta t$)). When $\Delta t$=1 s, joint rank distribution of $EEG_{LL}$ and dlnRR are no longer uniform such that higher ranks of dlnRR correspond to higher ranks of $EEG_{LL}$. The normalized conditional ranksum (CRS) of $EEG_{LL}$ (bottom panel) and dlnRR (left panel) highlight the non-uniformity of the joint distribution at $\Delta t$=1 s. The CRSs of $EEG_{LL}$ and dlnRR (black line) increase for higher ranks and decrease for lower ones. In contrast, the mean rank-sum for P(rank $EEG_{LL}$(t), rank dlnRR(t+$\Delta t$)|$\Delta t$=10 s) remains at approximately 0.5 (red line) which indicates a uniform distribution. Dashed gray lines indicate P-value=0.1. The joint distribution at $\Delta t$=1 s for the rank values around 0.5 is similar to the uniform joint distribution at $\Delta t$=10 s. dlnRR and $EEG_{LL}$ extracted from epileptic animal #9 (second black asterisk in FIG. 7), 73 days post infection, 12-1 PM.

It is shown in FIG. 10 that the joint distributions of EEG$_{LL}$ and dlnRR ranks, P(EEG$_{LL}$(t), dlnRR(t+$\Delta$t)), over different time-offsets, $\Delta$t, for an hour-long block of data. The ranks are normalized to be between [0,1]. The joint distributions are consistent with independence of the individual representations for three of the four time-offsets presented. Once the dlnRR distribution is shifted by a positive time-offset of one second with respect to the EEG$_{LL}$ ($\Delta$t=1 s), the joint distribution becomes highly non-uniform with high densities in the extrema of the ranks (indicated by darker corners in FIG. 10, $\Delta$t=1 s).

The non-uniformity of these joint distributions was quantified by computing the conditional rank-sum (CRS) of the EEG$_{LL}$ and dlnRR rank distributions. These conditional distributions are normalized to have expected mean rank of 0.5. The CRSs are shown for offset times $\Delta$t=1 s (black) and $\Delta$t=10 s (red), for the rank-sum of dlnRR as a function of EEG$_{LL}$ (left inset), and for the rank-sum of EEG$_{LL}$ as a function of dlnRR (bottom inset). For independence of representations EEG$_{LL}$ and dlnRR should have a uniform distribution and conditional rank-sums of 0.5, as observed for $\Delta$t=10 s. In contrast, the CRSs at $\Delta$t=1 s diverge far from that, consistent with interdependent distributions.

Figure 11:
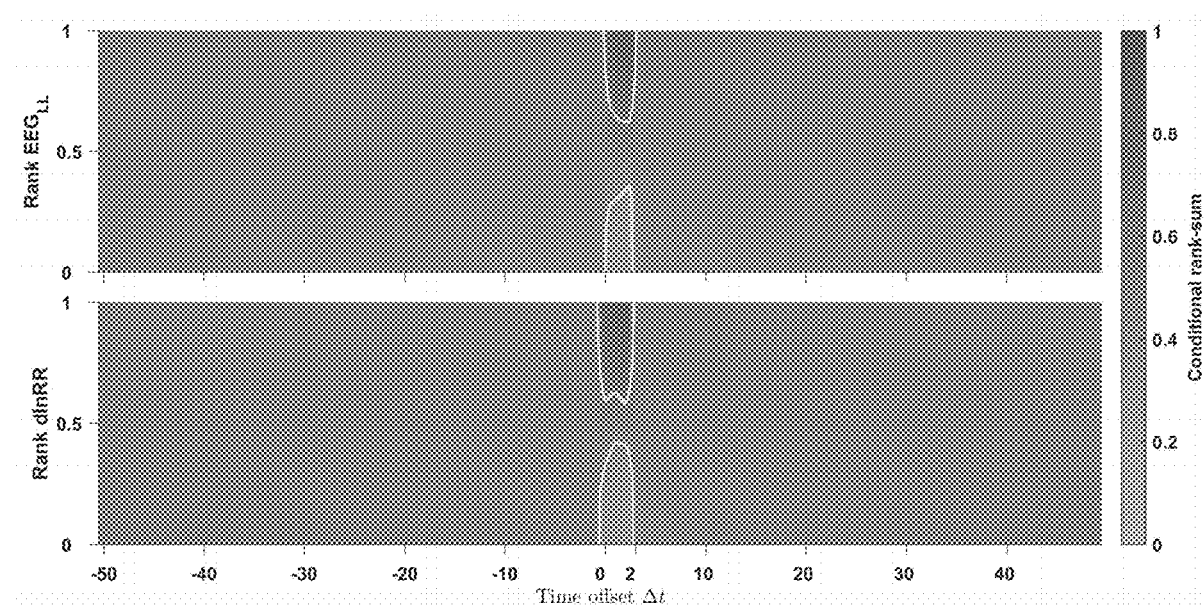
FIG. 11 is a chart depicting fluctuations in the brain ($EEG_{LL}$) and cardiac (dlnRR) representations are correlated only with a 0-2 s delay, according to the Examples described herein. Shown are the normalized conditional rank-sum distribution for $EEG_{LL}$ and dlnRR as a function of time-offset; $\Delta t$. Contour lines mark select iso-probability (Yellow=0.1) of the Wilcoxon rank-sum test with the null hypothesis that the ranks are chosen from independent distributions. Outside the time range 0≤$\Delta t$≤2 s, this test has PWilcoxon>>0.2 which is consistent with independent brain and heart representations. In contrast, within the small range of 0≤$\Delta t$≤2 s the normalized conditional rank-sums for both $EEG_{LL}$ and dlnRR diverge from independence for the extrema of the ranks (as shown in magenta and cyan areas). By construction, higher ranks in the $EEG_{LL}$ correspond to large values of $EEG_{LL}$ (consistent with cortical discharges) and higher ranks in dlnRR correspond to large values of dlnRR (consistent with transient increases in the duration of single RR intervals). That P≤0.1 inside the 0≤$\Delta t$≤2 s interval indicates a dependence between large fluctuations in brain or cardiac activity with a time-delay of 0-2 s. This threshold is marked by the gray dashed lines in the normalized conditional rank-sums in FIG. 10. Analysis from the same hour of data as in FIG. 10.

To illustrate the temporal changes in uniformity of the joint distribution, the conditional rank-sums of the EEG$_{LL}$ and dlnRR rank distributions were calculated, for the same hour-long block of data, over a sweep of time-offsets (−50≤$\Delta$t≤50 s). For almost all $\Delta$t, the CRSs fluctuated slightly around 0.5 as illustrated in FIG. 11. However, for the small range of time offsets, 0≤$\Delta$t≤2 s, the conditional rank-sums for both $EEG_{LL}$ and dlnRR rank distributions diverged significantly from 0.5. Significance here is quantified from the Wilcoxon rank-sum test P-value, which is the probability that the observed rank-sums would have come from independent distributions. Overlaid on FIG. 11 is the iso-contour for P-value of 0.1 (yellow). This probability of independence is observed in the range of $0 \leq \Delta t \leq 2$ s. The P-value of 0.1 for the specific $\Delta t=1$ s is marked by the dashed gray lines in the panels for conditional rank-sums in FIG. 10. Repeated independent excursions through this contour were used to yield highly significant observations (P<0.005).

Figure 18:
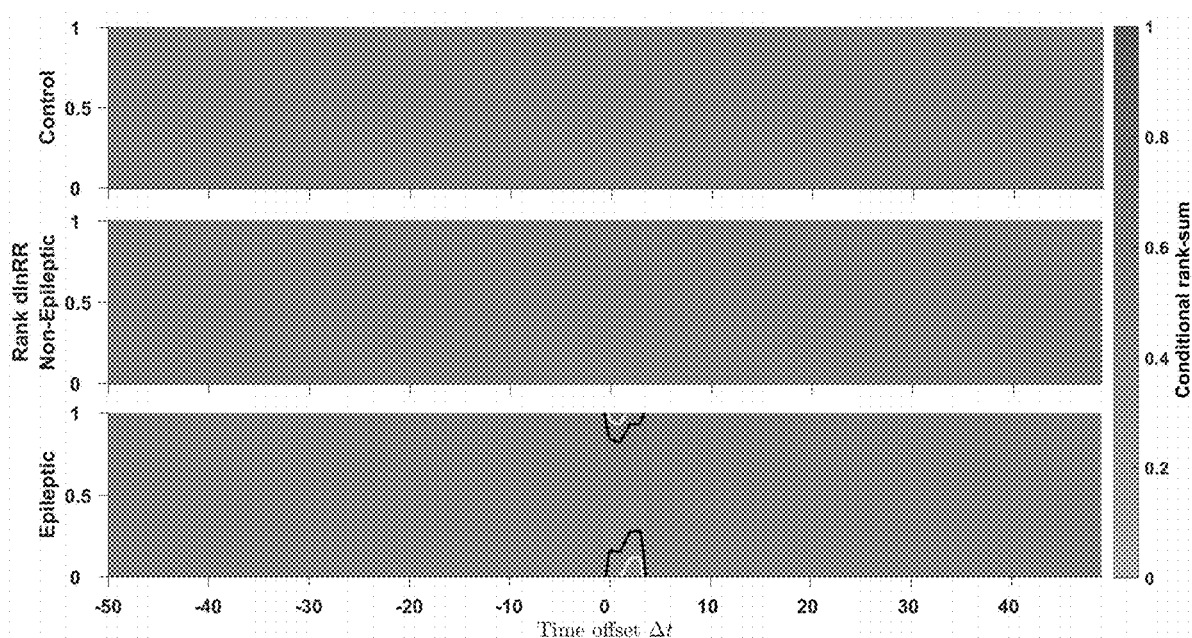
FIG. 18 is a chart showing fluctuations in the brain ($EEG_{LL}$) and cardiac (dlnRR) representations with a 0-2 s delay are only present in epileptic mice, according to the Examples described herein. Distribution of the normalized conditional rank-sum of $EEG_{LL}$ ($EEG_{LL}$|rank (dlnRR)) across different time-offsets ($\Delta t$) in an hour-long block of data for a control and a non-epileptic mouse as well as the epileptic mouse #9. Contour lines mark the iso-probabilities (Yellow=0.1; Black=0.2) of the Wilcoxon rank-sum test with the null hypothesis that the ranks are chosen from independent distributions. The conditional rank-sum (CRS) for the non-epileptic and control mice remain close to 0.5 over all time-offsets which is consistent with independent brain and heart representations. The conditional rank-sum for the epileptic animal outside the time range $0 \leq \Delta t \leq 2$ s is similar to the CRS for non-epileptic and control mice. In contrast, within the small range of $0 \leq \Delta t \leq 2$ s, the CRS diverges from independence for the extrema of the dlnRR ranks (as shown in magenta and cyan areas). This indicates a dependence between large fluctuations in brain or cardiac activity with a time-delay of 0-2 s that is absent in non-epileptic and control mice. Distributions are extracted from data early during the epileptogenesis (Day 30 post infection; first black asterisk in FIG. 7) for the epileptic mouse and are time-matched for the control and non-epileptic mice.

Epileptic mice were the only cohort that presented with high-value conditional rank-sums over time offsets of $0 \leq \Delta t \leq 2$ s. Shown in FIG. 18 are conditional rank-sums of $EEG_{LL}$ as a function of dlnRR, over a sweep of time-offsets ($-50 \leq \Delta t \leq 50$ s), for one epileptic animal 30 days post-infection and time-matched non-epileptic and control mice. The conditional rank-sum for the epileptic animal diverged from 0.5 within the small time range $0 \leq \Delta t \leq 2$ s. However, the control and non-epileptic mice had CRSs with small fluctuations around 0.5 at all times. Overlaid on FIG. 18 are iso-contours for P-values of 0.1 (yellow) and 0.2 (black).

The significant divergence of the joint dlnRR-$EEG_{LL}$ distribution from independence with a peak delay of 1 s implies that fluctuations in brain activity potentially cause or lead to fluctuations in cardiac activity. As illustrated in the joint distribution with $\Delta t=1$ s (FIG. 10) high-ranked values of $EEG_{LL}$ are correlated with high-ranked values of dlnRR 1 s later.

The Spearman's rank-order correlation test was utilized to quantify the correlation between the two distributions of $EEG_{LL}$ and dlnRR. Shown in FIG. 19 are the conditional rank-sums of $EEG_{LL}$ distributions for an hour-long block of data from epileptic, non-epileptic, and control mice. Overlaid on FIG. 19 are the Spearman's correlation coefficient ($\rho$) values (black solid lines) over a sweep of time-offsets, $-40 \leq \Delta t \leq 40$ s. Similar to the conditional rank-sum of $EEG_{LL}$ for the epileptic animal presented here, for almost all $\Delta t$ the Spearman's correlation coefficient fluctuated around zero (with standard deviation of 0.054 for $\Delta t \notin [-10,10]$). However, within the small range of $0 \leq \Delta t \leq 2$ s $\rho$ increased up to 0.8. In contrast, for non-epileptic and control animals the correlation coefficient remained smoothly fluctuating around zero (standard deviation of 0.052 for all $\Delta t$) which indicates no correlation between dlnRR and $EEG_{LL}$ distributions.

Without wishing to be bound by theory, it was hypothesized that this apparent brain to heart coupling is primarily mediated by isolated abnormal events. To demonstrate this, potentially abnormal events were algorithmically defined as those in the upper tails of the distributions. In particular the conditional rank threshold (cRT) was defined and the $EEG_{LL}$ and dlnRR ranks were selected that were above this threshold. cRT=0.99 is marked by the gray dashed line in FIG. 9A for the dlnRR distribution and by the red dashed line in FIG. 16B for $EEG_{LL}$ distribution. The values were extracted of the other representation as a function of time with respect to these high-rank values—brain or heart triggered events—and quantify, as a function of time-offset, whether their distribution is consistent with independence. In FIG. 12, examples of this analysis for the one-hour long data block presented in FIG. 10 are illustrated.

The distribution of dlnRR associated with potentially abnormal cortical events was evaluated, $P(EEG_{LL}(t), dlnRR(t+\Delta t)|rank(EEG_{LL}(t)) \geq cRT=0.99)$. The dlnRR distribution conditioned on cortical event times was calculated and evaluated against the null hypothesis that the dlnRR values are randomly selected, using the Wilcoxon rank-sum test.

Shown in FIG. 12A are the dlnRR distributions as a function of cortical event times. Here, the dlnRR distribution within 2 seconds after potentially abnormal brain events is significantly different from the distribution consistent with random selection (Wilcoxon rank-sum test p=0.0011). Further, many values within 2 seconds after these potentially abnormal brain events ($0 \leq \Delta t \leq 2$ s) belong to the 99% upper ranks of the dlnRR rank distribution (dlnRR$\geq 170$ $m^{-1}s^{-1}$).

We then evaluated the distribution of $EEG_{LL}$ conditioned on potentially abnormal cardiac event times—defined as the 99% upper ranks of the dlnRR rank distribution—was then evaluated, $P(EEG_{LL}(t-\Delta t), dlnRR(t)|rank(dlnRR(t)) \geq cRT=0.99)$, against the null hypothesis that the $EEG_{LL}$ values are randomly selected, using the Wilcoxon rank-sum test. Shown in FIG. 12B are the rank distributions of the $EEG_{LL}$ as a function of cardiac event times. $EEG_{LL}$ values within 2 seconds prior to potentially abnormal cardiac events ($0 \leq \Delta t \leq 2$ s) held significantly higher ranks compared to what was consistent with random distribution of ranks (Wilcoxon rank-sum test, p=1.2e-4).

It was found that distributions of abnormal cortical and cardiac events are not independent. In particular, the correspondence between large variations in brain activity, i.e. abnormal cortical events, and positive variations in the dlnRR occur more frequently than is expected from random co-occurrence. The similarity between the results of the analyses whether triggered by potentially abnormal brain events or by potentially abnormal cardiac events is consistent with the joint distribution in FIG. 10. The correspondence between the extrema of the ranks in the joint distribution is bidirectional such that high ranks in the rank (dlnRR(t+$\Delta t$)) coincide with the high ranks in the rank ($EEG_{LL}$).

Brain-Heart Coincidence as a Biomarker for Epileptogenesis

It was hypothesized that the significant divergence of the joint dlnRR and $EEG_{LL}$ distribution from uniformity within the specific range of $0 \leq \Delta t \leq 2$ s could be used to distinguish animals that would become epileptic from the ones that did not. Further, once quantified such divergences can serve as a biomarker of the epileptogenesis process.

In both analyses, brain- or cardiac-triggered events, for the animal presented in FIG. 12 P-value (Wilcoxon)<0.1 was selected as the criteria to mark an hour-long block of data for the existence of brain-heart coupling. This threshold corresponds to the yellow iso-contours in FIG. 11. As illustrated in the middle panel of FIG. 12, the hour was marked if the P-value of the Wilcoxon rank-sum test was less than 0.1 during the 2 s time-offset (red meshed area). For $0 \leq \Delta t \leq 2$ s the threshold for the potentially abnormal events—cRT=99%—lies at the extremity of the area bounded by the iso-contour of P=0.1. Therefore, the initial cRT=99% for the abnormal events is highly restrictive.

Hour-long blocks of data were marked for the existence of brain-heart coincidences from onset of recording until the first seizure. In this analysis the threshold of P-value <0.1 is applied to every hour within the day, and then averaged over the day. Given a random distribution, the error rate of 0.1 over 24 repeated measures results in the probability of 0.002 for observing a fraction of hours $\geq 0.33$ ($\geq 8$ out of 24) with brain-heart coincidences. The fraction of hours per week where the conditional dlnRR and $EEG_{LL}$ distributions were different than random is shown for one animal in the last panels of FIG. 12. These fractions increased nearly monotonically until the occurrence of the first seizure.

A cross-validation classification method was then adopted to separate epileptic from non-epileptic and control animals.

The conditional rank-sum (CRS) for $EEG_{LL}$ (conditioned on rank (dlnRR)≥0.99) was first computed for every hour-long block of data for all animals. Then every other day of measures from the first 14 days of recordings was selected for all animas as a training set, and the minimum CRS threshold that maximized the classification specificity for identifying epileptic animals was found. The conditional rank-sum threshold was then applied to all remaining data, and hours with CRSs larger than this threshold were marked for existence of brain-heart coincidences.

The fraction of hours per day with marked brain-heart coincidences is shown in FIG. 13A. Under the null hypothesis that ranks are selected randomly, the P-value associated with the rank-sum threshold is 0.0554. This threshold is applied to every hour within the day, and then averaged over the day. Therefore, with a random distribution (the null hypothesis) and 24 repeated measures it results in the probability of ≤0.002 for observing a fraction of hours ≥0.25 (≥6 out of 24) with brain-heart coincidences per day. For the epileptic animals these fractions fluctuate during the first 21 days post-recording onset, but they all generally increase during epileptogenesis. However, for non-epileptic animals they remain low from the onset of recording until time-of-death.

It is noted that the measurements, although continuous and long-term, started weeks after the malarial infection. Therefore, the exact onset of detectable neurophysiological changes during epileptogenesis in this data set remains unclear.

If a classification criteria is defined by maximizing specificity (black line in FIG. 13A and grey dashed line in FIG. 13B), using the fraction of marked hours per day, all 13 mice under analysis can be correctly classified into epileptic (n=9) and non-epileptic (n=4) groups over almost all of the period shown. One epileptic animal is temporarily misclassified within the third week of recording.

The sensitivity of the rank-sum classifier to the criteria of potentially abnormal events was further investigated. For data shown in FIG. 13A, the conditional rank-sum (CRS) of $EEG_{LL}$ was conditioned on rank threshold of 0.99 (rank (dlnRR)≥cRT=0.99). Shown in FIG. 13C are the minimum CRS thresholds selected as the classification boundary to mark hours for brain-heart coincidences over a sweep of rank thresholds (cRT E [85%,99%]). As more ranks are allowed into the potentially abnormal samples the rank-sum threshold increases in order to separate epileptic from non-epileptic and control animals with maximum specificity. Maximum specificity is achieved at the expense of degrading sensitivity. Neither specificity nor sensitivity decreases below 80% for all the rank-thresholds indicating the robustness of the classification over a wide range of conditional rank thresholds (cRT).

By expanding the analysis block size from one-hour blocks to full day intervals, the statistical power of this analysis can be increased. As done previously, CRS of $EEG_{LL}$ conditioned on rank threshold of 0.99 was computed for full day-long blocks of data, then the conditional rank-sum was derived in the window of 0≤Δt≤2 s, and finally the minimum P-value of the Wilcoxon rank-sum test over the range 0≤Δt≤2 s was marked.

The conditional rank-sum of the $EEG_{LL}$ within the range 0≤Δt≤2 s is shown in FIG. 14A for each day for all epileptic, non-epileptic, and control animals. As with the daily fractional detections (FIG. 13A), this representation steadily increases during epileptogenesis (for the epileptic animals) with smaller fluctuations during the first weeks of recordings. With this statistic, the epileptic animals are completely separated from non-epileptic animals from the first day of recording (FIG. 14B). Therefore, the representation provides a classifier with complete sensitivity and specificity.

The potentially abnormal events in FIG. 13A are based on the conditional rank threshold (cRT) of 0.99. In order to evaluate the sensitivity of the classifier presented in FIG. 13B to this threshold the analyses was repeated for a sweep of threshold values from 75-99%. As described previously, the conditional rank-sum (CRS) was calculated for day-long blocks of data for all animals, and the conditional rank-sum of the $EEG_{LL}$ within 0≤Δt≤2 s was found. The animals were then classified with a classification boundary to maximize specificity. As shown in FIG. 14C, the classification sensitivity begins to degrade when the conditional rank threshold (cRT) is below 95%, although specificity decreases only when the cRT is below 88%. Therefore, the analysis is quite robust for a range of statistically relevant thresholds over the rank distributions.

Figure 21:
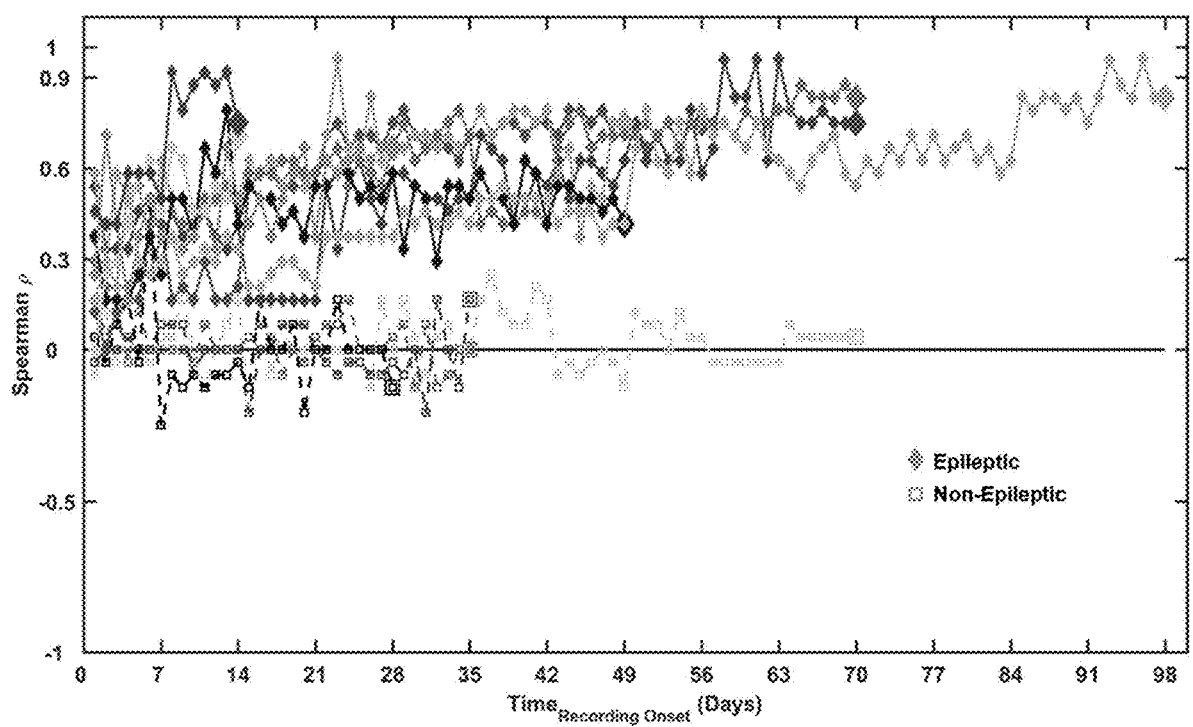
FIG. 21 is a chart depicting evolution of Spearman's correlation coefficient as a marker for Brain-to-Heart coupling in epileptic and non-epileptic mice, according to the Examples described herein. The Spearman's correlation coefficient is calculated for each hour-long block of data and then averaged over 24 hours for each day. The coefficient shows an increasing trend for epileptic animals (colored diamonds). In contrast, it remains low with small fluctuations around zero (marked by the solid black line) for the non-epileptic mice (brown squares). The markers are color-matched with FIG. 13A and FIG. 14A.

Spearman's correlation coefficient was utilized to quantify the evolution of brain-heart coupling during epileptogenesis independent of any thresholds. The Spearman's correlation coefficient (ρ) was computed for each hour-long block of data, the maximum value in the range of 0≤Δt≤2 s was selected, and the averaged value for each day was calculated. The evolution of daily averages of ρ for epileptic and non-epileptic animals is illustrated in FIG. 21. As with the daily fractional detections, for epileptic animals ρ has an overall increasing trend with large fluctuations during the first 21 days of recordings. For non-epileptic mice, ρ remains relatively low with small changes around zero.

Figure 22:
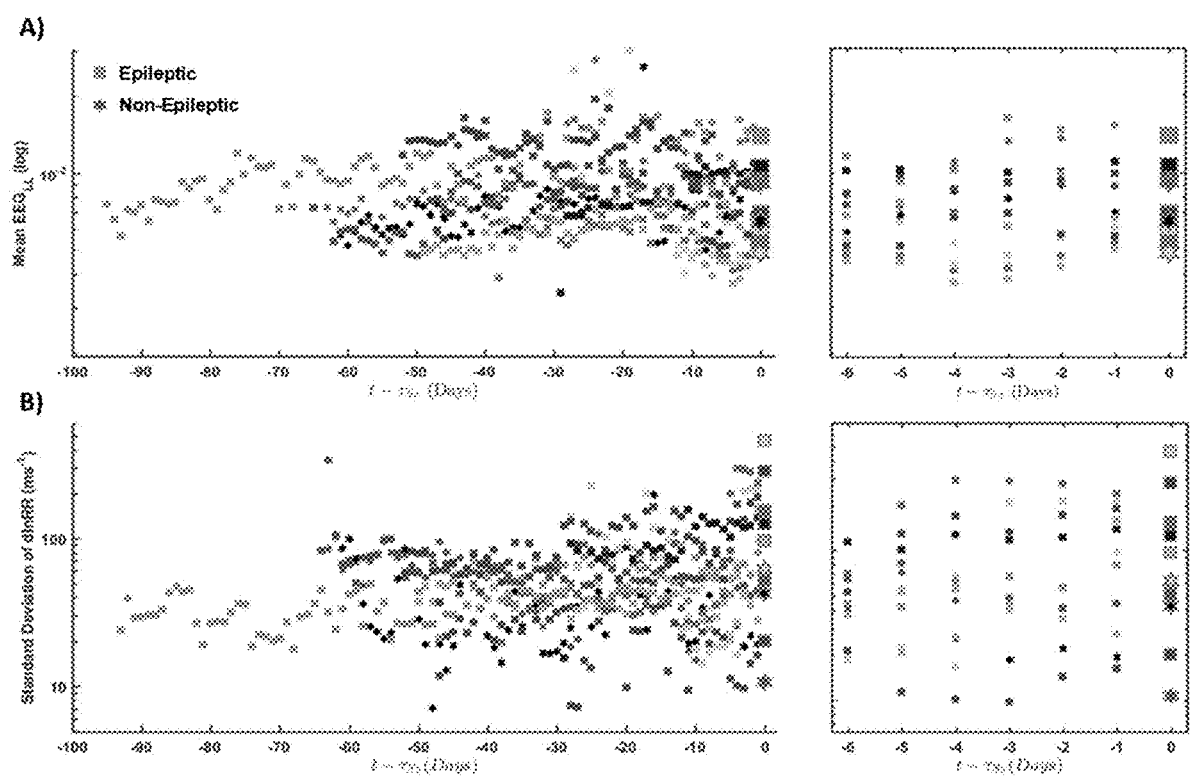
FIG. 22 is a series of charts depicting evolution of dlnRR and $EEG_{LL}$ distributions during epileptogenesis, according to the Examples described herein. Mean and standard deviation of dlnRR and $EEG_{LL}$ distributions for epileptic and non-epileptic mice as a function of time to first seizure for epileptic mice ($t-\tau_{sz}$), and time to death for non-epileptic mice. (A) shows distribution of $EEG_{LL}$ as a function of time is not different for epileptic (colored squares) vs. non-epileptic (brown hexagons) animals. Although for one epileptic animal the mean $EEG_{LL}$ transiently increases, it drops again. Even hours prior to the first seizure (right panel) the mean values are not differentiable between epileptic and non-epileptic mice. (B) shows by construction, dlnRR distribution has near-zero mean. But the standard deviation of the distribution describes local variability in the RR intervals. The standard deviation slowly rises for 4 (out of 9) of the epileptic animals (red, green, blue, and light blue traces) but it does not sufficiently separate them from non-epileptic mice.

It was further investigated if dlnRR and $EEG_{LL}$ on their own provide enough information to identify the progression of epileptogenesis as well as to separate epileptic, non-epileptic, and control groups. The mean $EEG_{LL}$ remained relatively stationary in the duration before the first seizure in epileptic mice and during entire lifetime for non-epileptic mice (FIG. 22A). Only for one epileptic animal did the mean $EEG_{LL}$ increase transiently, but it dropped again weeks before the first seizure. Even hours before the first seizure $EEG_{LL}$ did not vary between epileptic and non-epileptic animals (FIG. 22A-right panel).

The dlnRR distribution is approximately zero-mean. However, the width of the dlnRR distribution is a measure of local variability in RR interval. The standard deviation of dlnRR distribution slowly increased for a portion of epileptic animals (n=4). However, the variations in the standard deviation of dlnRR (presented in FIG. 22B) were not differentiable for epileptic vs. non-epileptic mice.

Figure 23:
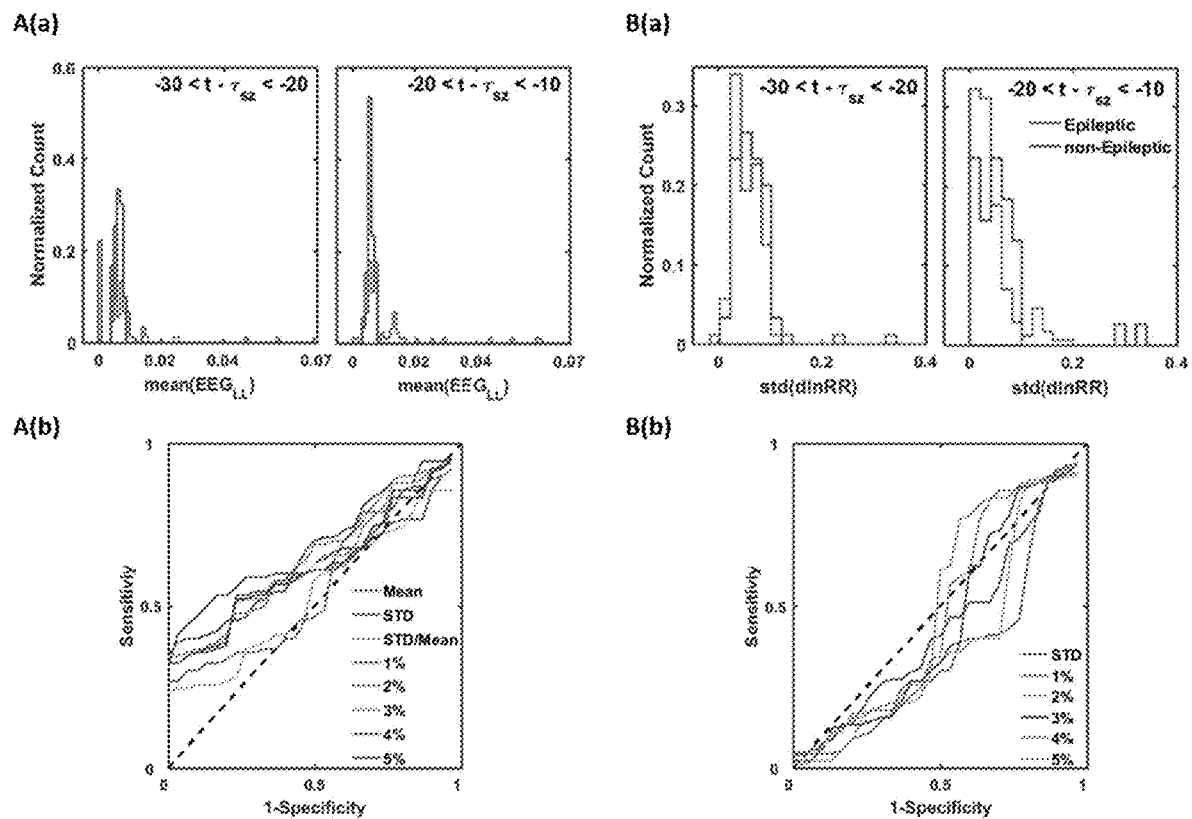
FIG. 23 is a series of charts depicting dlnRR and $EEG_{LL}$ alone cannot separate different cohorts, according to the Examples described herein. The distributions of mean of $EEG_{LL}$ (A.a) and standard deviation of dlnRR (B.a) are pooled from 10-day intervals of recordings from all epileptic (magenta) and non-epileptic mice (green). The two distributions are overlapping which indicates that as a feature for classification neither of them provides sufficient sensitivity or specificity. Receiver Operating Characteristics (ROC) curves are calculated for a variety of statistical measures of the (A.b) $EEG_{LL}$ and (B.b) dlnRR distributions including mean, standard deviation, standard deviation normalized by the mean, and values of the 1-5% upper-bounds. As shown by the ROCs none provide significant sensitivity or specificity to separate the epileptic from non-epileptic animals.

Both $EEG_{LL}$ and dlnRR distributions significantly overlap for epileptic and non-epileptic animals (FIG. 23A.a and FIG. 23B.a). A variety of statistical measures were tested for each of the distributions as features to separate epileptic from non-epileptic mice. None provided significant sensitivity or specificity to separate, as illustrated by the Receiver Operating Characteristics (ROC) curves of mean, standard deviation, standard error of the mean, and values of the 1-5% upper bounds.

Discussion

Continuous long-term recordings in a murine model of post-cerebral malaria epilepsy were used to derive representations of brain-heart interactions. The statistical co-dependence of these representations as a biomarker of the epileptogenesis period was then investigated in 9 epileptic mice. Underlying these representations are delayed coincidences of large fluctuations in brain activity causing—approximately 1 s later—large fluctuations in cardiac rhythmicity. Line length was used as the representation for brain activity to specifically highlight epileptiform events and transient cortical discharges. The representation of cardiac rhythmicity was designed to be independent of state of vigilance (SOV) and to highlight abrupt changes in cardiac rhythm with resolution of single long RR intervals. By construction, abnormal brain and cardiac events result in large positive values of the corresponding representations.

It was demonstrated that abnormal cortical discharges precede abnormally long single RR intervals. These delayed coincidences were only detected from brain-triggered or heart-triggered analyses in animals that later became epileptic. Further, once quantified, it was observed that the strength of the coupling between abnormal brain and heart events increases during epileptogenesis.

The observations that sub-convulsive cortical discharges lead to isolated long RR intervals implicate involvement of the autonomic nervous system impinging on heart. The possible mechanistic bases for this phenomenon might be imbalanced parasympathetic activity transmitted to the heart via the vagal nerve or a decrease in sympathetic activity. The detected positive time-delay of 1 s is consistent with previous reports of an induced reduction in heart rate after electrical stimulation of the vagal nerve branch innervating the heart.[52, 63] In the context of epilepsy, these findings support the body of evidence that epileptic discharges and seizure activity recruit cortical structures as well as autonomic nuclei regulating cardiac rhythmicity.[38, 45, 46, 53]

Impaired cardiac function is considered a contributing clinical manifestation of severe childhood malaria.[32, 42, 64] One might question whether the observations described herein are due to post-malarial cardiac dysfunction. Animals identified as non-epileptic in this study experienced and then were rescued from cerebral malaria and therefore were subject to potential cardiac damage. Compared to animals that later became epileptic we found negligible incidents of abnormally long RR intervals and abnormal brain-to-heart coincidences in non-epileptic mice. Control animals presented with even lower incidence of development of abnormal transmission along brain-heart axis. The findings described herein are thus not attributed to the cardio-pathological effects of malarial infection.

The strength of the brain-to-heart coupling during epileptogenesis shown in FIG. 13 and FIG. 14 exhibited an increasing pattern with day-by-day fluctuations in the first 3-4 weeks of recordings. Compared to the large variations in the daily fractional detections (FIG. 13A), the day long detection representation (FIG. 14A) shows relatively smaller day-by-day variations. Therefore, the day-long detections separate pre-epileptic and non-epileptic animals with complete sensitivity and specificity from the first day of the recordings. The high degree of separability of pre-epileptic from non-epileptic and control mice provided can thus be utilized in phenotyping animals in studies and assessing risk of epilepsy in patients.

The large fluctuations of the daily fractional representation (FIG. 13A) in all pre-epileptic mice reflect the finer temporal variations of the brain-to-heart coupling. These fluctuations were the most severe in the animal that was transiently misclassified (light blue trace in FIG. 13A). These changes may be part of the dynamic nature of epileptogenesis. It was hypothesized that successful treatments to interrupt epileptogenesis will be reflected as decreases in the abnormal brain-to-heart coupling captured via the daily fractional detections.

In future work, the observation of development of abnormal brain-to-heart coupling prior to the first convulsive seizure can be adapted to forecast seizure clusters with long seizure-free intervals between them. These clusters would be reflected in increases of the abnormal brain-to-heart coincidences followed by gradual decreases representative of the seizure-free periods.

The cortically-induced disturbances of cardiac rhythm have the potential to make the network more susceptible to more seizures and vulnerable to their effects.[1, 11, 33, 38, 54] The Lockstep phenomenon (LSP) is evidence that epileptic discharges can interrupt autonomic regulation. Therefore LSP is proposed to share a common underlying mechanism with SUDEP.[1, 15, 39, 40, 53] The observations described herein of abnormal brain-to-heart coupling implies that cortical discharges are involved in induced autonomic disbalance that could create a vicious cycle that leads to catastrophic conditions such as gradual deterioration of physiological signs and increased risk of SUDEP. For these cases, the strength of the brain-to-heart coupling could be investigated to assess the need and efficacy of cardiac pacemakers to reduce risk of SUDEP.

Although there are quite a few animal models of epilepsy, the time-course of disease development and the underlying processes do not necessarily match human epileptogenesis periods. The murine post-cerebral malaria epilepsy studied here models the human conditions of post-infection acquired epilepsy. Both express long and variable epileptogenesis periods prior to observations of spontaneous seizures. The findings described herein of brain-heart coincidences in this model can offer a novel approach to prevent epilepsy in high-risk patients—post traumatic brain injuries, post-infection, post-anoxic/ischemic, post-surgical—through pharmacological trials with biomarker monitoring.

The brain-heart coincidence representation introduced here is based on fast temporal correlations—of the order of 1-2 seconds—between variations in single RR intervals and small fluctuations in brain activity. The temporal resolution needed for detection of such correlation is enabled because mouse heart beats many times per second. The analyses presented here may need to be adjusted for the relatively slower heart rates in human subjects for clinical applications.

A critical need in biomarker research is development of preferably non-invasive and less costly markers that can be applied easily to human population. In the exemplary method disclosed herein, the brain-to-heart coupling during epileptogenesis was detected from coincidences between EEG and ECG. Electrocardiograms are non-invasive. But further investigation of the underlying mechanisms of brain-heart axis may include measurements from the vagal nerve innervating the heart. Direct measurements of the cardiac branch of the vagal nerve can be provided by bipolar electrodes and implanted radio-transmitters.[9, 34, 44, 56, 60]

The work presented here highlights one of the many potential mechanistic coincidences between central nervous system and much more accessible physiological measurements. These physiological measures such as cardiac activity for parasympathetic and skin sympathetic nerve activity for sympathetic nervous system[14, 62] limb motion[31, 29, 30, 36, 65] cerebrovascular function[4], and state of vigilance (SOV)[55] can not only provide more insight into the underlying mechanisms of neurologically-sourced pathologies but can lead to novel diagnostic approaches and identification of new phenotypic features.

REFERENCES

1. Altenmüller, Dirk Matthias, Manfred Zehender, and Andreas Schulze-Bonhage. 2004. "High-Grade Atrioventricular Block Triggered by Spontaneous and Stimulation-Induced Epileptic Activity in the Left Temporal Lobe." Epilepsia 45(12): 1640-44.
2. Ansakorpi, H et al. 2002. "Heart Rate Dynamics in Refractory and Well Controlled Temporal Lobe Epilepsy." Journal of neurology, neurosurgery, and psychiatry 72(1): 26-30.
3. Baharav, A et al. 1995. "Fluctuations in Autonomic Nervous Activity during Sleep Displayed by Power Spectrum Analysis of Heart Rate Variability." Neurology 45(6): 1183-87. http://www.ncbi.nlm.nih.gov/pubmed/7783886.
4. Bar-Klein, Guy et al. 2014. "Losartan Prevents Acquired Epilepsy via TGF-?? Signaling Suppression." Annals of Neurology 75(6): 864-75.
5. _____. 2016. "Isoflurane Prevents Acquired Epilepsy in Rat Models of Temporal Lobe Epilepsy." Annals of Neurology 80(6): 896-908.
6. _____. 2017. "Imaging Blood-Brain Barrier Dysfunction as a Biomarker for Epileptogenesis." Brain 140(6): 1692-1705.
7. Boudreau, Philippe, Wei-Hsien Yeh, Guy A. Dumont, and Diane B. Boivin. 2013. "Circadian Variation of Heart Rate Variability Across Sleep Stages." Sleep 36(12): 1919-28. https://academic.oup.com/sleep/article-lookup/doi/10.5665/sleep.3230.
8. Bryce, R. M., and K. B. Sprague. 2012. "Revisiting Detrended Fluctuation Analysis." Scientific Reports 2.
9. Choi, Eue Keun et al. 2010. "Intrinsic Cardiac Nerve Activity and Paroxysmal Atrial Tachyarrhythmia in Ambulatory Dogs." Circulation 121(24): 2615-23.
10. DeGiorgio, Christopher M. et al. 2010. "RMSSD, a Measure of Vagus-Mediated Heart Rate Variability, Is Associated with Risk Factors for SUDEP: The SUDEP-7 Inventory." Epilepsy and Behavior 19(1): 78-81.
11. Devinsky, O, S Pacia, and G Tatambhotla. 1997. "Bradycardia and Asystole Induced by Partial Seizures: A Case Report and Literature Review." Neurology 48(6): 1712-14.
12. Devinsky, Orrin. 2004. "Effects of Seizures on Autonomic and Cardiovascular Function." Epilepsy Currents 4(2): 43-46.
13. Dichter, M A. 2009. "Emerging Concepts in the Pathogenesis of Epilepsy and Epileptogenesis." Archives of Neurology 66(4): 443-47. http://dx.doi.org/10.1001/archneurol.2009.10.
14. Doytchinova, Anisiia et al. 2017. "Simultaneous Noninvasive Recording of Skin Sympathetic Nerve Activity and Electrocardiogram." Heart Rhythm 14(1): 25-33.
15. Dütsch, Mathias, Max J. Hilz, and Orrin Devinsky. 2006. "Impaired Baroreflex Function in Temporal Lobe Epilepsy." Journal of neurology 253(10): 1300-1308. http://www.ncbi.nlm.nih.gov/pubmed/17041741.
16. van Elmpt, Wouter J. C., Tamara M. E. Nijsen, Paul A. M. Griep, and Johan B. A. M. Arends. 2006. "A Model of Heart Rate Changes to Detect Seizures in Severe Epilepsy." Seizure 15(6): 366-75.
17. Engel, Jerome et al. 2013. "Epilepsy Biomarkers." Epilepsia 54(SUPPL.4): 61-69.
18. Engel, Jerome, Anatol Bragin, Richard Staba, and Istvan Mody. 2009. "High-Frequency Oscillations: What Is Normal and What Is Not?" Epilepsia 50(4): 598-604.
19. Esteller, R. et al. 2001. "Line Length: An Efficient Feature for Seizure Onset Detection." In 2001 Conference Proceedings of the 23rd Annual International Conference of the IEEE Engineering in Medicine and Biology Society, IEEE, 1707-10. http://ieeexplore.ieee.org/lpdocs/epic03/wrapper.htm?arnumber=1020545.
20. Evrengül, Harun et al. 2005. "Time and Frequency Domain Analyses of Heart Rate Variability in Patients with Epilepsy." Epilepsy Research 63(2-3): 131-39.
21. Frysinger, R C, J Engel, and R M Harper. 1993. "Interictal Heart Rate Patterns in Partial Seizure Disorders." Neurology 43(10): 2136-39.
22. Fujiwara, Koichi et al. 2015. "Epileptic Seizure Prediction Based on Multivariate Statistical Process Control of Heart Rate Variability Features." IEEE Transactions on Biomedical Engineering 9294(c): 1-1. http://ieeexplore.ieee.org/lpdocs/epic03/wrapper.htm?arnumber=7365453.
23. Giftakis, J E, and N M Graves. 2006. "System and Method for Monitoring or Treating Nervous System Disorders." https://encrypted.google.com/patents/WO2006066098A1?cl=en.
24. Goodman, J H, M Stewart, and F W Drislane. 2008. "Autonomic Disturbances." In Epilepsy: A Comprehensive Textbook, 1995-2005.
25. Govindan, Rathinaswamy B. et al. 2014. "Detrended Fluctuation Analysis of Non-Stationary Cardiac Beat-to-Beat Interval of Sick Infants." EPL 108(4).
26. Gowers, William Richard. 1881. Epilepsy and Other Chronic Convulsive Diseases: Their Causes, Symptoms, & Treatment. Churchill.
27. Hajek, Michael A., and Gordon F. Buchanan. 2016. "Influence of Vigilance State on Physiological Consequences of Seizures and Seizure-Induced Death in Mice." Journal of Neurophysiology 115(5): 2286-93.
28. Hashimoto, Hirotsugu et al. 2013. "Heart Rate Variability Features for Epilepsy Seizure Prediction." In 2013 Asia-Pacific Signal and Information Processing Association Annual Summit and Conference, APSIPA 2013.
29. Hellwig, B et al. 2001a. "Early Report Tremor-Correlated Cortical Activity in Essential Tremor." Lancet 357: 519-23.
30. _____. 2001b. "Tremor-Correlated Cortical Activity in Essential Tremor." The Lancet 357(9255): 519-23. http://linkinghub.elsevier.com/retrieve/pii/S0140673600040447.
31. Hellwig, B. et al. 2000. "Tremor-Correlated Cortical Activity Detected by Electroencephalography." Clinical Neurophysiology 111(5): 806-9.
32. Herr, Johanna et al. 2011. "Reduced Cardiac Output in Imported *Plasmodium falciparum* Malaria." Malaria Journal 10.
33. Hilz, M. J. et al. 2002. "Decrease of Sympathetic Cardiovascular Modulation after Temporal Lobe Epilepsy Surgery." Brain 125(5): 985-95. https://academic.oup.com/brain/article-lookup/doi/10.1093/brain/awf092.
34. Jung, Byung Chun et al. 2006. "Circadian Variations of Stellate Ganglion Nerve Activity in Ambulatory Dogs." Heart Rhythm 3(1): 78-85.
35. Kane, Nick et al. 2017. "A Revised Glossary of Terms Most Commonly Used by Clinical Electroencephalographers and Updated Proposal for the Report Format of the EEG Findings. Revision 2017." Clinical Neurophysiology Practice 2: 170-85. http://linkinghub.elsevier.com/retrieve/pii/S2467981X17300215 (Sep. 5, 2017).
36. Kanemaru, Nao et al. 2014. "Jerky Spontaneous Movements at Term Age in Preterm Infants Who Later Developed Cerebral Palsy." Early Human Development 90(8): 387-92. http://linkinghub.elsevier.com/retrieve/pii/S0378378214001285.

37. Kheiri, Farshad et al. 2012. "Non-Linear Classification of Heart Rate Parameters as a Biomarker for Epileptogenesis." Epilepsy Research 100(1-2): 59-66.
38. Lathers, Claire M., Paul L. Schraeder, and Francine L. Weiner. 1987. "Synchronization of Cardiac Autonomic Neural Discharge with Epileptogenic Activity: The Lockstep Phenomenon." Electroencephalography and Clinical Neurophysiology 67(3): 247-59.
39. van der Lende, Marije, Rainer Surges, Josemir W Sander, and Roland D Thijs. 2016. "Cardiac Arrhythmias during or after Epileptic Seizures." Journal of neurology, neurosurgery, and psychiatry 87(1): 69-74. http://jnnp.bmj.com/content/early/2015/06/02/jnnp-2015-310559.full?
40. Leutmezer, Fritz et al. 2003. "Electrocardiographic Changes at the Onset of Epileptic Seizures." Epilepsia 44(3): 348-54.
41. Masse, Fabien et al. 2013. "Miniaturized Wireless ECG Monitor for Real-Time Detection of Epileptic Seizures." ACM Transactions on Embedded Computing Systems 12(4): 1. http://dl.acm.org/citation.cfm?doid=2485984.2485990.
42. Mockenhaupt, Frank P et al. 2004. "Manifestation and Outcome of Severe Malaria in Children in Northern Ghana." The American Journal of Tropical Medicine and Hygiene 71(2): 167-72. http://eutils.ncbi.nlm.nih.gov/entrez/eutils/elink.fcgi?dbfrom=pubmed&id=15306705&retmode=ref&cmd=prlinks%5Cnpapers3://publication/uuid/5eb0838a-28b4-4cc4-a5ec-11f949d4ed60.
43. Moridani, M. K., and H. Farhadi. 2017. "Heart Rate Variability as a Biomarker for Epilepsy Seizure Prediction." Bratislava Medical Journal 118(1): 3-8.
44. Ogawa, Masahiro et al. 2007. "Left Stellate Ganglion and Vagal Nerve Activity and Cardiac Arrhythmias in Ambulatory Dogs With Pacing-Induced Congestive Heart Failure." Journal of the American College of Cardiology 50(4): 335-43.
45. Oppenheimer, S M, J X Wilson, C Guiraudon, and D F Cechetto. 1991. "Insular Cortex Stimulation Produces Lethal Cardiac-Arrhythmias—a Mechanism of Sudden-Death." Brain Research 550: 115-21.
46. Oppenheimer, Stephen M., and David F. Cechetto. 1990. "Cardiac Chronotropic Organization of the Rat Insular Cortex." Brain Research 533(1): 66-72.
47. Pavei, Jonatas et al. 2017. "Early Seizure Detection Based on Cardiac Autonomic Regulation Dynamics." Frontiers in Physiology 8. http://journal.frontiersin.org/article/10.3389/fphys.2017.00765/full.
48. Peng, C.-K. et al. 1995. "Fractal Mechanisms and Heart Rate Dynamics." Journal of Electrocardiology 28: 59-65. http://linkinghub.elsevier.com/retrieve/pii/S0022073695800174.
49. Pitkänen, Asla et al. 2016. "Advances in the Development of Biomarkers for Epilepsy." The Lancet Neurology 15(8): 843-56.
50. Pitkänen, Asla, Reina Roivainen, and Katarzyna Lukasiuk. 2016. "Development of Epilepsy after Ischaemic Stroke." The Lancet Neurology 15(2): 185-97.
51. Ronkainen, E et al. 2005. "Suppressed Circadian Heart Rate Dynamics in Temporal Lobe Epilepsy." Journal of neurology, neurosurgery, and psychiatry 76(10): 1382-86. http://www.pubmedcentral.nih.gov/articlerender.fcgi?artid=1739357&tool=pmcentrez&rendertype=abstract.
52. Rosenblueth, A, and F A Simeone. 1934. "The Interrelations of Vagal and Accelerator Effects on the Cardiac Rate." American Journal of Physiology 110(1): 42-55.
53. Schraeder, P. L., and C. M. Lathers. 1983. "Cardiac Neural Discharge and Epileptogenic Activity in the Cat: An Animal Model for Unexplained Death." Life Sciences 32(12): 1371-82.
54. Schuele, S. U. et al. 2007. "Video-Electrographic and Clinical Features in Patients with Ictal Asystole." Neurology 69(5): 434-41.
55. Sedigh-Sarvestani, Madineh et al. 2014. "Rapid Eye Movement Sleep and Hippocampal Theta Oscillations Precede Seizure Onset in the Tetanus Toxin Model of Temporal Lobe Epilepsy." The Journal of neuroscience: the official journal of the Society for Neuroscience 34: 1105-14. http://www.ncbi.nlm.nih.gov/pubmed/24453303.
56. Sevcencu, Cristian, Thomas N. Nielsen, and Johannes J. Struijk. 2016. "Changes in Vagus Nerve Activity Associated with Ictal Tachycardia in Pigs." Epilepsy Research 128: 52-60.
57. Shanmugasundaram, Balaji, and Bruce J. Gluckman. 2017. "Micro-Reaction Chamber Microelectrodes Especially for Neural and Biointerfaces."
58. Ssentongo, Paddy et al. 2017. "AMurine Model to Study Epilepsy and SUDEP Induced by Malaria Infection." Scientific reports 7: 43652. https://www.nature.com/articles/srep43652.pdf (Aug. 17, 2017).
59. Sunderam, Sridhar et al. 2007. "Improved Sleep-Wake and Behavior Discrimination Using MEMS Accelerometers." Journal of Neuroscience Methods 163(2): 373-83.
60. Tan, Alex Y. et al. 2008. "Neural Mechanisms of Paroxysmal Atrial Fibrillation and Paroxysmal Atrial Tachycardia in Ambulatory Canines." Circulation 118(9): 916-25.
61. Tasker, Robert C, and Sally H Vitali. 2014. "Continuous Infusion, General Anesthesia and Other Intensive Care Treatment for Uncontrolled Status Epilepticus." Current Opinion in Pediatrics 26(6): 682-89. http://www.ncbi.nlm.nih.gov/pubmed/253139750%5Cnhttp://content.wkhealth.com/linkback/openurl?sid=WKPTLP:landingpage&an=00008480-201412000-00012.
62. Uradu, Andrea et al. 2017. "Skin Sympathetic Nerve Activity Precedes the Onset and Termination of Paroxysmal Atrial Tachycardia and Fibrillation." Heart Rhythm 14(7): 964-71.
63. Warner, Homer R., and Albert Cox. 1964. "A Mathematical Model of Heart Rate Control by Sympathetic and Vagus Efferent Information." Simulation 3(1): 63-71.
64. Yacoub, Sophie et al. 2010. "Cardiac Function and Hemodynamics in Kenyan Children with Severe Malaria." Critical Care Medicine 38(3): 940-45. http://content.wkhealth.com/linkback/openurl?sid=WKPTLP:landingpage&an=00003246-201003000-00030.
65. Zafeiriou, D I, E E Kontopoulos, and I Tsikoulas. 1999. "Characteristics and Prognosis of Epilepsy in Children with Cerebral Palsy." Journal of child neurology 14(5): 289-94.

What is claimed is:

1. A method of evaluating the effectiveness of an intervention measure, comprising:
estimating the risk of occurrence of a physiological event in a mammal, wherein said estimating comprises:
obtaining brain activity data that describes brain activity of the mammal over a first period of time;

obtaining peripheral activity data that describes peripheral activity of the mammal over a second period of time;

receiving, by at least one device, brain data from a brain activity measurement device that describes brain activity of a mammal over the first period of time;

receiving, by the at least one device, periphery data from a peripheral activity measurement device that describes peripheral activity of a mammal over the second period of time;

generating, by the at least one device, one or more brain feature representations based on the brain data;

generating, by the at least one device, one or more periphery feature representations based on the periphery data;

generating, by the at least one device, one or more brain statistical distributions of the one or more brain feature representations;

generating, by the at least one device, one or more periphery statistical distributions of the one or more periphery feature representations;

identifying, by the at least one device, one or more brain feature representations that fall outside of a predetermined range in the brain statistical distribution to generate a set of one or more target brain feature representations;

identifying, by the at least one device, one or more periphery feature representations that fall outside of a predetermined range in the periphery statistical distribution to generate a set of one or more target periphery feature representations;

determining, by the at least one device, a brain-periphery temporal association between the one or more target brain feature representations and the one or more target periphery feature representations;

determining, by the at least one device, an estimate of risk of a future physiological event based on the brain-periphery temporal association; and providing, by the at least one device, an indication of the estimate of risk of the future physiological event;

applying at least one intervention measure that is commensurate with the prevention of the physiological event; and determining the effectiveness of the intervention measure.

2. The method of claim 1, wherein estimating the risk and applying the intervention measure are performed automatically.

3. The method of claim 1, wherein said mammal is a human.

4. The method of claim 1, wherein said mammal is at risk of developing or has a neurologic disease, and wherein said neurological disease is epilepsy.

5. The method of claim 1, wherein the physiological event is selected from the onset of acquired epilepsy, an epileptic seizure, sudden unexpected death in epilepsy (SUDEP), hydrocephalus, sepsis, and onset of cerebral palsy.

6. The method of claim 1, wherein the intervention measure is an anti-epileptogenic therapy.

7. The method of claim 1, wherein the intervention measure is administration of an anti-epileptic drug (AED).

8. The method of claim 7, wherein said AED is selected from the group consisting of acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, rufinamide, sodium valproate, stiripentol, tiagabine, topiramate, vigabatrin, zonisamide, and combinations thereof.

9. The method of claim 1, further comprising determining, by the system, a quantification of the brain-periphery temporal association; wherein providing the estimate of risk of a future physiological event is based on the quantification of the brain-periphery temporal association.

10. The method of claim 9, further comprising:
determining, by the system, an estimate of the timing of a future physiological event based on the quantification of the brain-periphery temporal association; and
providing an indication of the estimate of the timing of the future physiological event.

11. The method of claim 1, further comprising:
determining, by the system, an estimate of the timing of a future physiological event based on the brain-periphery temporal association; and
providing an indication of the estimate of the timing of the future physiological event.

12. The method of claim 1, wherein the periphery statistical distribution is independent of behavioral state.

13. The method of claim 1, wherein the brain activity data is electroencephalography (EEG) data.

14. The method of claim 1, wherein the periphery data is selected from cardiac data, muscle movement data, nerve activity data, pupil dilation data, and body movement data.

15. The method of claim 1, wherein the periphery data is cardiac data, and wherein the cardiac data is selected from electrocardiogram (ECG) data, blood pressure data, and photoplethysmography (PPG) data.

16. The method of claim 1, wherein the periphery data is ECG data, and wherein the physiological event is selected from the onset of acquired epilepsy, an epileptic seizure, and SUDEP.

17. The method of claim 1, wherein the peripheral activity data was obtained from a peripheral activity measurement device that is integrated with or communicatively coupled to a smartphone, a tablet computer, a watch body, a watch band, or a wearable patch.

18. The method of claim 1, further comprising displaying, on a display device, an output indicative of the estimate of risk of the physiological event.

* * * * *